United States Patent [19]

Bacon et al.

[11] Patent Number: 5,541,187
[45] Date of Patent: Jul. 30, 1996

[54] 6-HETEROCYCYCLYL PYRAZOLO[3,4-D]PYRIMIDIN-4-ONES AND COMPOSITIONS AND METHOD OF USE THEREOF

[75] Inventors: Edward R. Bacon; Baldev Singh, both of East Greenbush, N.Y.; George Y. Lesher, deceased, late of Schodack, N.Y., by Louise E. Lesher, executor

[73] Assignee: Sterling Winthrop Inc., Malvern, Pa.

[21] Appl. No.: 159,158

[22] Filed: Nov. 30, 1993

Related U.S. Application Data

[62] Division of Ser. No. 859,770, Mar. 30, 1992, Pat. No. 5,294,612.

[51] Int. Cl.$^6$ ............... A61K 31/505; A61K 31/535; C07D 413/00; C07D 213/44
[52] U.S. Cl. ............... 514/258; 514/234.2; 514/234.5; 544/118; 544/262
[58] Field of Search ............... 544/118, 262; 514/258, 234.5, 234.2

[56] References Cited

U.S. PATENT DOCUMENTS

| | | | |
|---|---|---|---|
| 3,165,520 | 1/1965 | Schmidt et al. | 544/262 |
| 3,211,731 | 10/1965 | Schmidt et al. | 544/262 |
| 3,350,397 | 10/1967 | Burch | 544/262 |
| 3,732,225 | 5/1973 | Breuer et al. | 544/262 |
| 4,167,568 | 4/1979 | Knowles | 514/258 |
| 4,666,908 | 5/1987 | Hamilton | 514/229 |
| 5,075,310 | 12/1991 | Coates | 514/258 |

FOREIGN PATENT DOCUMENTS

| | | |
|---|---|---|
| 463756 | 1/1992 | European Pat. Off. . |
| 526004 | 2/1993 | European Pat. Off. . |
| 937722 | 9/1963 | United Kingdom . |
| 88/00192 | 1/1988 | WIPO . |
| 93/06104 | 4/1993 | WIPO . |

OTHER PUBLICATIONS

Hamilton et al, Journal Med. Chem. vol. 30, pp. 91–96 (1987).
Burch,—J. Med. Chem. 1968, pp. 79–83.
Miyashita et al, Heterocycles, 1990, p. 1309.

*Primary Examiner*—Cecilia Tsang
*Attorney, Agent, or Firm*—Paul E. DuPont; Richard A. Hake

[57] ABSTRACT

Novel 6-heterocyclyl-pyrazolo[3,4-d]pyrimidin-4-ones, useful in treating cardiovascular disease, are prepared by reacting a 5-amino-1H-pyrazole-4-carboxamide with heterocyclyl-carboxaldehyde or by reacting a 5-amino-1H-pyrazole-4-carbonitrile with a heterocyclylcarboxamidine, followed by diazotization and hydrolysis of the resulting 4-amino-6-heterocyclyl-pyrazolo[3,4-d]pyrimidine.

29 Claims, No Drawings

6-HETEROCYCYCLYL PYRAZOLO[3,4-D]PYRIMIDIN-4-ONES AND COMPOSITIONS AND METHOD OF USE THEREOF

This application is a division of application Ser. No. 07/859,770, filed Mar. 30, 1992, now U.S. Pat. No. 5,294,612, issued Mar. 15, 1994.

BACKGROUND OF THE INVENTION (a) Field of the Invention

The invention relates to novel 6-heterocyclyl-pyrazolo [3,4-d]-pyrimidin-4-ones, which inhibit the enzymatic activity of phosphodiesterase (PDE), and to the preparation thereof and the use thereof in treating cardiovascular disease.

(b) Information Disclosure Statement

U.S. Pat. No. 3,165,520 to Schmidt et al. discloses as coronary dilating agents pyrazolo[3,4-d]pyrimidines of general formula:

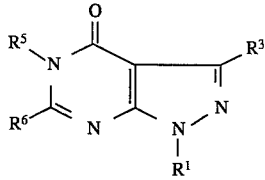

wherein:

$R^1$ represents a hydrogen atom or an alkyl, hydroxyalkyl, halogen-alkyl or oxa-alkyl radical or a cycloalkyl, cycloalkylalkyl, aralkyl or heterocyclylalkyl radical or an at most binuclear aryl or heterocyclic radical;

$R^3$ represents a hydrogen atom or a lower-alkyl radical;

$R^5$ represents an aliphatic, cycloaliphatic, cycloaliphatic-aliphatic, araliphatic or heterocyclic-aliphatic radical; and $R^6$ represents an aliphatic radical or an aralkyl or heterocyclyl-alkyl radical which may be substituted.

The patent more specifically discloses as especially valuable the compounds in which $R^1$ represents a hydrogen atom or a lower-alkyl radical; $R^3$ represents a hydrogen atom or a lower-alkyl radical; $R^5$ represents a lower-alkyl radical and $R^6$ represents a lower-alkyl radical or an aralkyl radical.

U.S. Pat. No. 3,211,731 to Schmidt et al. discloses as coronary dilating agents pyrazolo[3,4-d]pyrimidines of general formula:

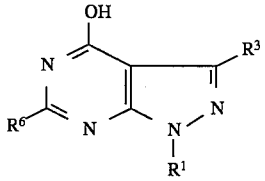

wherein:

$R^1$ represents hydrogen, an alkyl, hydroxy-alkyl, halogen-alkyl or oxa-alkyl radical, a cyclo-alkyl, cycloalkylalkyl, aralkyl, heterocyclyl-alkyl radical or an at most binuclear aryl or heterocyclic radical;

$R^3$ stands for hydrogen, or in the second place, for a lower-alkyl radical; and $R^6$ represents a possibly substituted aralkyl or heterocyclylalkyl radical.

The patent more specifically discloses as especially valuable the compounds in which $R^1$ represents a hydrogen atom or a lower-alkyl group; $R^3$ represents a hydrogen atom or lower-alkyl and $R^6$ an aralkyl.

U.S. Pat. No. 3,211,732 to Schmidt et al. discloses as intermediates 1-$R^1$-3-$R^3$-6-$R^6$-4-hydroxy-pyrazolo [3,4-d] pyrimidines wherein:

$R^1$ represents a hydrogen atom, a lower-alkyl radical which is unsubstituted or substituted by a hydroxy group or a lower-alkoxy group, or a cyclopentyl or cyclohexyl radical or a phenyl or phenyl lower-alkyl radical;

$R^3$ represents a hydrogen atom or a lower-alkyl radical; and $R^6$ stands for a phenyl lower-alkyl radical or a phenyl radical which may be substituted.

U.S. Pat. No. 3,732,225 to Breuer et al. discloses as hypoglycemic agents and anti-inflammatory agents pyrazolo [3,4-d]-pyrimidines of formula:

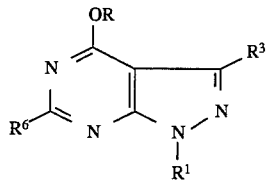

wherein:

R is hydrogen or lower-alkyl; $R^1$ is lower-alkyl, cycloalkyl, phenyl or substituted phenyl; $R^2$ is phenyl, substituted phenyl or cycloalkyl; and $R^3$ is hydrogen, lower-alkyl, cycloalkyl, phenyl or substituted phenyl.

U.S. Pat. No. 3,350,397 to Burch discloses as antibacterial agents pyrazolo[3,4-d]pyrimidines of formula:

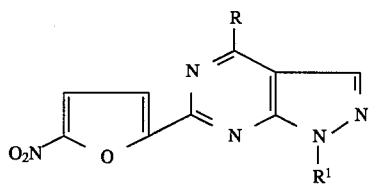

wherein:

R represents a member of the group consisting of hydroxy, chloro and —n(X)(Y) wherein X represents a member of the group consisting of hydrogen, (lower) alkyl, hydroxy (lower) alkyl, (lower)alkoxy(lower)alkyl and amino; Y represents a member of the group consisting of hydrogen, hydroxy (lower) alkyl, (lower) alkoxy(lower)alkyl and morpholinopropyl; X and Y taken together with N represent pyrrolidyl; and $R^1$ represents a member of the group consisting of (lower)alkyl and methoxyethyl.

The patent further discloses, as intermediates, 4-amino and 4-hydroxy-1-$R^1$-6-(2-furyl)-1H-pyrazolo [3,4-d]pyrimidines. The preparation of intermediates and the preparation and biological testing of final products is further exemplified by Burch in J. Med. Chem. 1968, 11, 79.

British Patent 937,722 to CIBA LIMITED discloses as a coronary dilating agent 1-isopropyl-4-hydroxy-6-benzyl-pyrazolo[3,4-d]pyrimidine.

U.S. Pat. No. 4,666,908 to Hamilton discloses pyrazolo [4,3-d]pyrimidine-7-ones of formula:

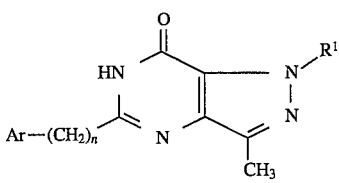

wherein:

R$^1$ is lower-alkyl of from one to six carbons, inclusive, lower-alkylene of from one to six carbon, inclusive, lower-hydroxyalkyl of from one to six carbons, inclusive, lower-hydroxyalkylene of from two to six carbons, inclusive, lower-aminoalkyl of from one to six carbons, inclusive, or lower-aminoalkylene of from two to six carbons, inclusive;

n is 0–4; and

Ar is:

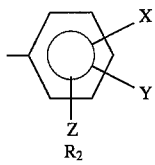

or 2, 3 or 4-pyridyl wherein X, Y and Z are independently (1) hydrogen; (2) lower-alkyl of from one to six carbons, inclusive; (3) halogen; (4) hydroxyl; (5) lower-alkoxy of from one to six carbons, inclusive; (6) nitro; (7) amino; (8) NR'R" wherein R' and R" are each independently (a) hydrogen or (b) lower-alkyl of from one to six carbons, inclusive, optionally substituted by (i) amino, (ii) morpholino, or (iii) cycloalkyl of from five to seven carbons, inclusive, (9) sulfonyl or (10) —SO2 NR'R" wherein R' and R" are as defined above.

The patent more specifically discloses as preferred compounds those wherein Ar is R$_2$. The compounds are stated to be useful in the treatment of cardiovascular disorders.

Miyashita et al. (Heterocycles 1900, 31, 1309.) describes the preparation of a series of pyrazolo[3,4-d]pyrimidines of general formula:

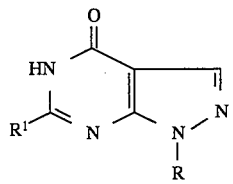

wherein:

R is phenyl or methyl; and R$^1$ is hydrogen, methyl, ethyl, propyl, isopropyl, benzyl, ethyl carboxylate or phenyl. No indication of utility is disclosed.

Hamilton PCT Application WO 88/00192, published Jan. 14, 1988, discloses a series of 5-substituted pyrazolo [4,3-d]pyrimidin-7-one derivatives useful as cardiotonic, CNS stimulative, antiallergy, antiasthma or cognition activating agents.

Bell et al. European Patent Application 0463756, published Jan. 2, 1992, disclose a series of 5-(2,5-disubstituted-phenyl)pyrazolo[4,3-d]pyrimidin-7-ones useful in the treatment of cardiovascular disorders.

SUMMARY OF THE INVENTION

In a composition of matter aspect the invention relates to compounds of the Formula I:

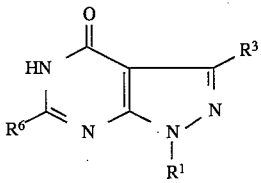

wherein:

R$^1$ is hydrogen, alkyl, cycloalkyl, cycloalkyl substituted by alkyl or hydroxyl; 2- or 3-tetrahydrofuranyl, 3-tetrahydrothienyl 1,1-dioxide, cycloalkyl-alkyl, carboxyalkyl, carbo-lower-alkoxy-alkyl, dialkylaminoalkyl, phenyl-lower-alkyl, phenyl-lower-alkyl in which the phenyl ring is substituted in the 2, 3, or 4-position by one or two substituents, the same or different, selected from the group consisting of amino, halogen, alkyl, carboxyl, carbo-lower-alkoxy, carbamoyl, NHSO$_2$-(quinolinyl), nitro and cyano;

R$^3$ is hydrogen, lower-alkyl, phenyl-lower-alkyl, lower-alkoxyphenyl-lower-alkyl, dilower-alkoxyphenyl-lower-alkyl, pyridyl-lower-alkyl, cycloalkyl-lower-alkyl, phenylamino, dialkylamino, halogen, trifluoromethyl, lower-alkylthio, cyano or nitro; and R$^6$ is a five or six membered heterocyclic ring containing from one to two nitrogen atoms, or a nine or ten membered bicyclic ring containing from one to two nitrogen atoms, or any of these substituted at any available carbon atom by one or two substituents, the same or different, selected from the group consisting of lower-alkyl, halogen, lower-alkoxy, cycloalkyloxy, 4-morpholinyl, lower-alkoxy-lower-alkoxy, hydroxy, imidazolyl, oxo and 4-morpholinyl-lower-alkoxy; or at any available nitrogen atom by lower-alkyl, lower-alkanoyl, or trifluoroacetyl; or a pharmaceutically acceptable acid-addition salt thereof.

The compounds of the present invention possess c-GmP-PDE I inhibitory activity and are thus useful in the treatment of heart failure and hypertension.

Preferred compounds of Formula I above are those wherein:

R$^6$ is pyridyl, or pyridyl substituted by one or two substituents, the same or different, selected from the group consisting of lower-alkyl, halogen, lower-alkoxy, cycloalkyloxy, lower-alkoxy-lower-alkoxy, imidazolyl, and 4-morpholinyl-lower-alkoxy;

R$^1$ is alkyl, cycloalkyl or substituted phenyl-lower-alkyl; and

R$^3$ is lower-alkyl, trifluoromethyl, phenyl-lower-alkyl, dilower-alkoxyphenyl-lower-alkyl, pyridyl-lower-alkyl or cycloalkyl-lower-alkyl.

Particularly preferred compounds of Formula I above are those wherein:

R$^6$ is 4-pyridyl, or 4-pyridyl substituted by one or two substituents, the same or different, selected from the group consisting of lower-alkyl, halogen, lower-alkoxy, cycloalkyloxy, lower-alkoxy-lower-alkoxy, imidazolyl, and 4-morpholinyl-lower-alkoxy;

R$^1$ is tert-butyl or cyclopentyl; and

R$^3$ is lower-alkyl, trifluoromethyl, phenyl-lower-alkyl, dilower-alkoxyphenyl-lower-alkyl, pyridyl-lower-alkyl, or cyclo-alkyl-lower-alkyl.

In a further composition of matter aspect, the invention relates to pharmaceutical compositions comprising a compound of Formula I together with a pharmaceutically acceptable carrier or diluent.

In a process aspect, the invention relates to a method for effecting cGMP-phosphodiesterase inhibition in a mammalian organism which comprises administering to said organism an effective amount of a compound of Formula I.

In a further process aspect, the invention relates to a method for treating heart failure in a mammalian organism which comprises administering to said organism an effective amount of a compound of Formula I.

In a still further process aspect, the invention relates to a method for treating hypertension in a mammalian organism which comprises administering to said organism an effective amount of a compound of Formula I.

In a still further process aspect, the invention relates to a process for preparing a compound of Formula I which comprises reacting a compound of Formula II:

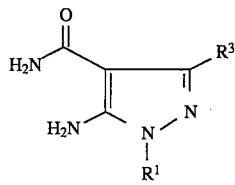

with an aldehyde of the formula $R^6CHO$.

DETAILED DESCRIPTION INCLUSIVE OF PREFERRED EMBODIMENTS

The compounds of Formula I may exist in tautomeric equilibrium with the corresponding enol form:

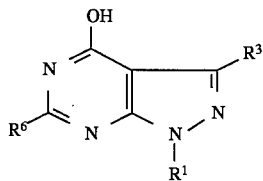

While the compounds are believed to be predominantly in the keto form and will be represented as such throughout this specification, it is to be understood that the invention contemplates both forms and mixtures thereof.

As used herein, unless specifically defined otherwise, the term "alkyl" means linear or branched hydrocarbon chains having from one to ten carbon atoms, for example, methyl, ethyl, propyl, isopropyl, n-butyl, sec-butyl, n-pentyl, 1-methylbutyl, 2-methylbutyl, neopentyl, n-hexyl, 1-methylpentyl, 3-methylpentyl, 1-ethylbutyl, 2-ethylbutyl, 2-hexyl, 3-hexyl, n-heptyl, 2-heptyl, n-octyl, 2,4,4-trimethylpentyl, n-nonyl, 3,5,5-trimethylhexyl, n-decyl, 3,7-dimethyloctyl and the like.

The term "cycloalkyl" means bridged or unbridged hydrocarbon ring systems having from three to seven carbon atoms, for example, cyclopropyl, cyclobutyl, cyclopentyl, cyclohexyl, cycloheptyl, norbornyl, and the like.

The term "cycloalkyloxy" means saturated monocyclic hydrocarbon ring systems having from three to seven carbon atoms, for example, cyclopropyloxy, cyclobutyloxy, cyclopentyloxy, cyclohexyloxy, cycloheptyloxy and the like.

The term "lower-alkoxy" means linear or branched alkyloxy substituents having from one to four carbon atoms, for example, methoxy, ethoxy, propoxy, isopropoxy, butoxy, secbutoxy, and the like.

The term "halogen" means bromine, chlorine, iodine or fluorine.

The term "quinolinyl" means 2-, 3-, 4-, 5-, 6-, 7- or 8-quinolinyl.

The term "lower-alkyl" means linear or branched hydrocarbon chains having one to four carbon atoms, for example, methyl, ethyl, propyl, isopropyl, n-butyl, sec-butyl, and the like.

The term "lower-alkanoyl" means linear or branched hydrocarbon chains having two to four carbon atoms, for example acetyl, propionyl, butyryl, isobutyryl and the like.

The five or six membered monocyclic and nine or ten membered bicylic heterocycle containing from one to two nitrogen atoms ($R^6$), which may be saturated or unsaturated, are attached through any available carbon or nitrogen atom thereof to the 6-position of the pyrazolo[3,4-d]pyrimidine ring.

The synthesis of compounds of the invention may be outlined as shown in Scheme A:

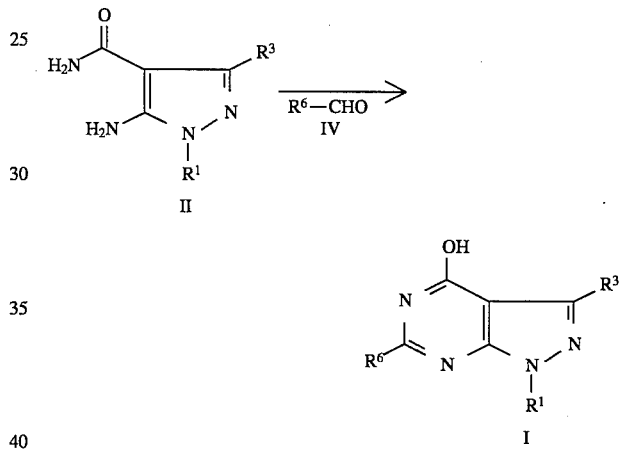

A suitably substituted 5-amino-1H-pyrazole-4-carboxamide (II) is reacted with an excess of an appropriately substituted heterocyclylcarboxaldehyde (IV) in an inert solvent, preferably xylenes or toluene at a temperature in the range from about 70° C. up to the boiling point of the solvent used, with or without the use of an acid catalyst, preferably p-toluenesulfonic acid, methanesulfonic acid or acetic acid.

Alternatively, a suitably substituted 5-amino-1H-pyrazole-4-carboxamide (II) is reacted (a) with an excess of an appropriately substituted heterocyclylcarboxylic acid halide (V, X' is halogen) or acid-addition salt thereof, e.g. the hydrochloride, in the absence of a solvent at a temperature sufficient to form a melt; (b) with an excess of an appropriately substituted heterocyclylcarboxamidine (VI) or acid-addition salt thereof, e.g. the hydrochloride, in the presence of a base, preferably potassium carbonate, in an inert solvent, preferably dimethylformamide at a temperature in the range from about 70° C. up to the boiling point of the solvent used; or (c) with an excess of an appropriately substituted heterocyclylcarboxylic acid ester (VII, R=lower-alkyl), preferably a methyl or ethyl ester, in the presence of a base, preferably sodium ethoxide, in an alcoholic solvent such as ethanol at a temperature in the range from about 60° C. up to the boiling point of the solvent used.

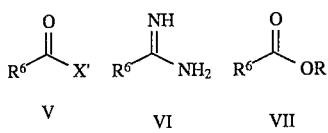

Alternatively, a suitably substituted lower-alkyl 5amino-1H-pyrazole-4-carboxylate (VIII), preferably a methyl ester, is reacted with an excess of a suitably substituted heterocyclylcarboxamidine (VI) or acid-addition salt thereof, e.g. the hydrochloride, in the presence of a base, preferably potassium carbonate, in an inert solvent, preferably dimethylformamide, at a temperature in the range from about 70° C. up to the boiling point of the solvent used.

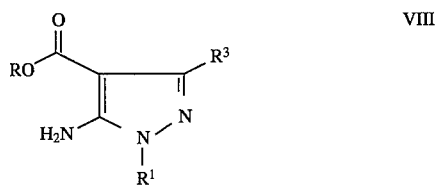

The compounds of the invention may also be synthesized as outlined in Scheme B:

Scheme B

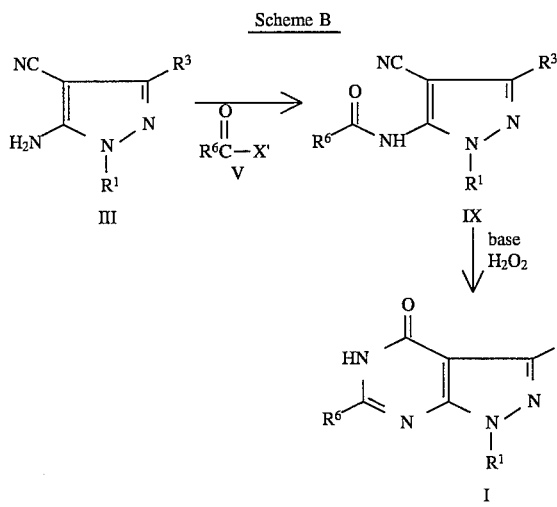

A suitably substituted 5-amino-1H-pyrazole-4-carbonitrile (III) is reacted with an excess of a suitably substituted heterocyclylcarboxylic acid halide (V) or acid-addition salt thereof, e.g. the hydrochloride, in the absence of a solvent at a temperature sufficient to form a melt, followed by treatment of the resulting 4-cyano-1H-pyrazole-5-heterocyclylcarboxamide (IX) with an excess of hydrogen peroxide in the presence of an excess of a base, preferably potassium hydroxide, in a solvent, preferably water, at a temperature in the range of form about 80° C. up to the boiling point of the solvent used. The 4-cyano-1H-pyrazole-5-heterocyclylcarboxamide (IX) can also be prepared by treatment of the 5-amino-1H-pyrazole-4-carbonitrile (III) with an appropriate heterocyclylcarboxylic acid (R⁶COOH) in the presence of an excess of a base, e.g. sodium hydride, and an excess of a suitable condensing reagent, e.g. 1, 1'carbonyldiimidazole or 1,3-dicyclohexylcarbodiimide, using procedures well known in the art.

Alternatively, the compounds of the invention may be synthesized as outlined in Scheme C:

Scheme C

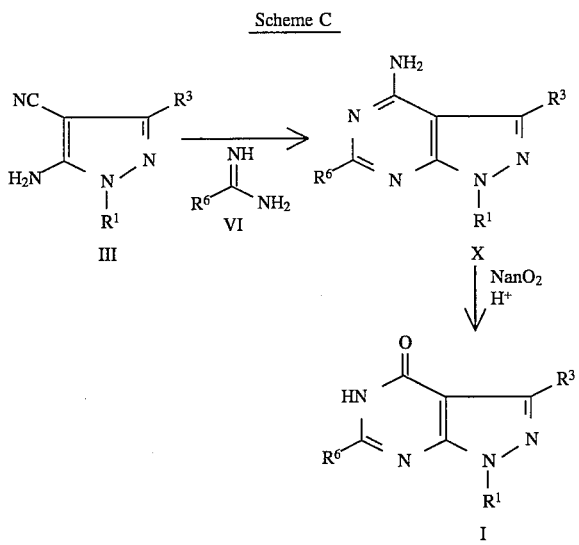

A suitably substituted 5-amino-1H-pyrazole-4-carbonitrile (III) is reacted with an excess of a suitably substituted heterocyclylcarboxamidine (VI) or acid addition salt thereof, e.g. the hydrochloride, in the presence or absence of an excess of a base, preferably potassium carbonate, in an inert solvent such as dowtherm, DMF or N-methyl-2-pyrrolidinone, preferably N-methyl-2-pyrrolidinone, at a temperature in the range from about 100° C. up to the boiling point of the solvent used; followed by treatment of the resulting pyrazolo[3,4-d]pyrimidin-4-amine (X) with an excess of sodium nitrite at a temperature in the range from about −10 to about 100° C., preferably −10 to 25° C., in a 30–70% aqueous acid solvent such as acetic acid, trifluoroacetic acid or sulfuric acid, preferably sulfuric acid. The pyrazolo[3,4-d]pyrimidin-4-amine (X) may also be prepared by (a) treatment of a suitably substituted 5-amino-1H-pyrazole-4-carbonitrile (III) with an excess of an appropriately substituted heterocyclylimidate ester (XI, R=loweralkyl), preferably the methyl ester, in the absence of a solvent at a temperature

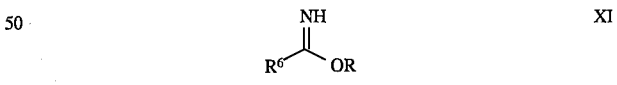

sufficient to form a melt; (b) by treatment of a suitably substituted 5-amino-1H-pyrazole-4-carboxamide (II) with an excess of an appropriately substituted heterocyclylcarbonitrile (R⁶CN) in the presence of a base, such as sodium hydride, in an organic solvent, such as dimethylformamide, at a temperature in the range from ambient up to the boiling point of the solvent used; or (c) by treatment of a suitably substituted pyrazolo[3,4-d]pyrimidin-4-amine (XII) with an appropriately substituted halide (XIII, X is Cl, Br, or I) in the presence of a base, preferably sodium hydride, in an inert solvent, preferably DMF at a temperature in the range from ambient up to the boiling point of the solvent used (Scheme D).

Scheme D

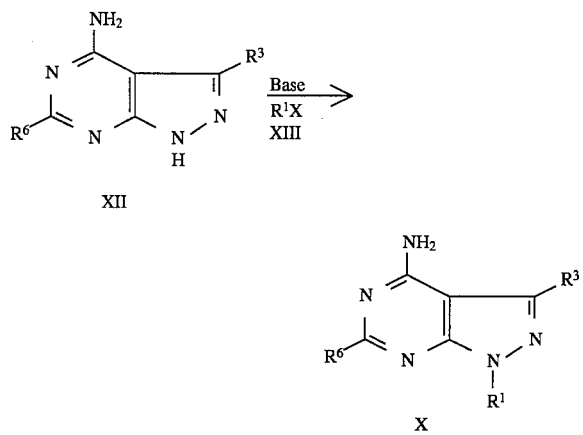

When it is necessary to prepare a compound of the Formula X wherein $R^3$ is halogen, it is desirable to dissolve the corresponding compound of Formula X wherein $R^3$ is hydrogen in water and bubble the appropriate halogen gas into the solution while maintaining the temperature in the range from ambient temperature up to the boiling point of the solvent used. If a compound of the Formula X wherein $R^3$ is nitro is desired it is convenient to treat the corresponding compound of the Formula X wherein $R^3$ is hydrogen with nitric acid in the presence of a strong acid, preferably sulfuric acid, at a temperature in the range from ambient temperature up to the boiling point of the solvent used.

In certain instances when it is desirable to prepare compounds of the Formula I wherein the $R^6$ substituent is attached through a nitrogen atom thereof to the 6-position of the pyrazolo[3,4-d]pyrimidine ring it is convenient to proceed as shown in Scheme E:

Scheme E

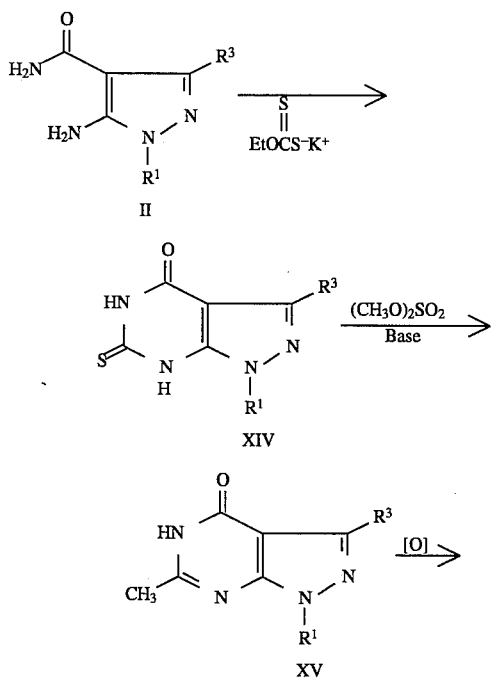

Scheme E -continued

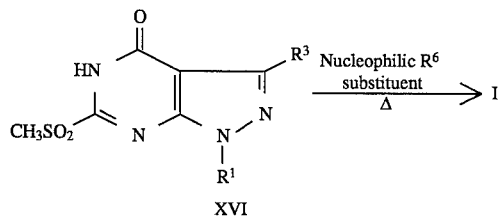

A suitably substituted 5-amino-1H-pyrazole-4-carboxamide (II) is reacted with an excess of an o-ethylxanthic acid salt, e.g. the potassium salt, in a high boiling organic solvent, such as N-methyl-2-pyrrolidinone, at a temperature in the range from about 80° C. up to the boiling point of the solvent used to produce the 6-thioxo-pyrazolo[3,4-d]pyrimidine derivative XIV. This derivative can then be alkylated by an excess of an alkylating agent, such as dimethylsulfate, or methyl iodide, in the presence of an excess of a base, such as potassium carbonate, in an organic solvent such as dimethylformamide, at ambient temperature to produce the 6-(methylthio)pyrazolo[3,4-d]pyrimidine intermediate XV, which can be oxidized in the presence of an excess of a strong oxidizing agent, such as m-chloroperoxybenzoic acid, in a halogenated solvent, such as chloroform, at ambient temperature to provide the 6-methylsulfonylpyrazolo[3,4-d]pyrimidine intermediate XVI. Treatment of the latter derivative with an excess of a nucleophilic $R^6$ substituent, e.g. imidazole, in the absence of a solvent at a temperature sufficient to form a melt affords the desired compounds of Formula I.

In those instances where a partially or completely saturated heterocyclyl substituent $R^6$ is desirable, it is convenient to treat a compound of the Formula I with hydrogen in a Parr hydrogenator at a temperature in the range from about 50° C. to about 70° C., in an alcoholic solvent, such as ethanol, in the presence of a catalyst, preferably platinum oxide. It is convenient to perform the reaction at about 50° C. when a partially saturated derivative is desired, e.g. 1,2,3,4-tetrahydroquinolinyl, or at about 70° C. when a completely saturated derivative, e.g. perhydroquinolinyl or piperidinyl, is desired.

In those cases where it is desired to have a tetrahydrofuranyl substituent at the 1-position ($R^1$=tetrahydrofuranyl) it is convenient to treat a compound of the Formula I, where $R^1$=H, with an excess of a dihydrofuran derivative in an organic solvent, such as dimethylformamide, in the presence of an excess of an acid catalyst, preferably boron trifluoride etherate, at a temperature in the range from about 0° C. to ambient temperature.

The 5-amino-1H-pyrazole-4-carboxamide (II) and the 5-amino-1H-pyrazole-4-carbonitrile (III) may be synthesized as outlined in Scheme F:

Scheme F

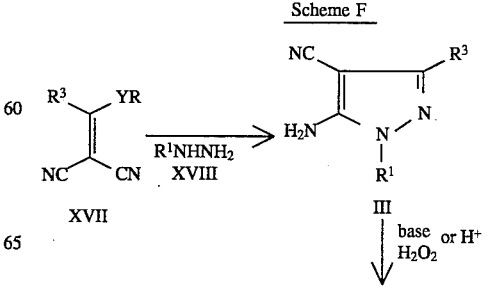

-continued
Scheme F

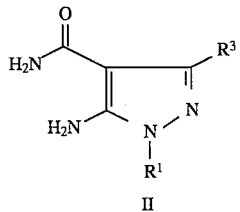

II

-continued
Scheme G

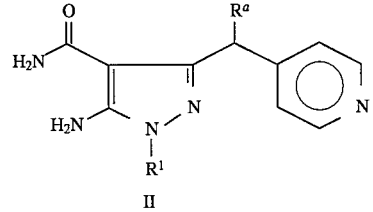

II

A suitably substituted malononitrile derivative (XVII, Y=O or S), wherein RY is preferably methoxy, ethoxy or methylthio is condensed with a suitably substituted hydrazine or hydrate thereof, or acid-addition salt thereof, e.g. the hydrochloride, (XVIII) in the presence or absence of a base such as sodium methoxide, triethylamine or potassium carbonate in a solvent such as ethanol, methoxyethanol or dioxane at a temperature in the range of from about 60° C. up to the boiling point of the solvent used. The resulting 5-amino-1H-pyrazole-4-carbonitrile III is then reacted with an excess of hydrogen peroxide in the presence of an excess of a base, preferably potassium or sodium hydroxide, in a solvent, preferably water, at a temperature from about 0° C. up to ambient temperature; or with an acid, preferably concentrated sulfuric acid, at a temperature from about 0° C. up to ambient temperature to produce carboxamide (II).

In those instances where it is desirable to prepare a compound of the Formula (II) wherein $R^3$ is pyridyl-lower-alkyl it is advantageous to proceed as shown in Scheme G:

Scheme G

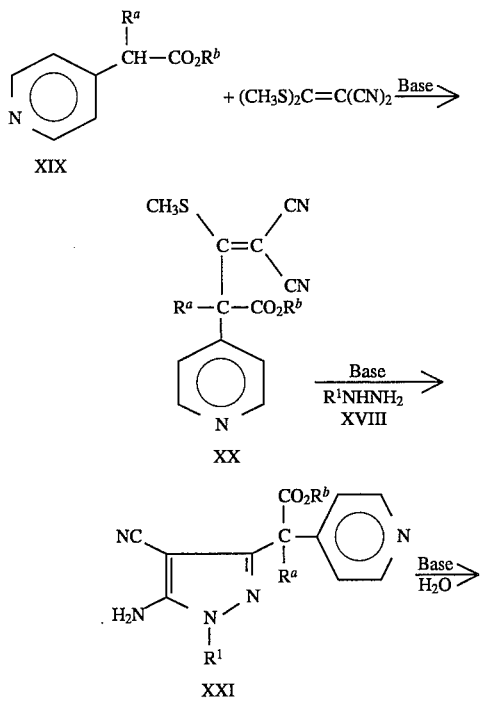

A suitably substituted pyridineacetate XIX ($R^a$=hydrogen or lower-alkyl, $R^b$ lower-alkyl) is treated with 3,3-bis-(methylthio)-2-cyanoacrylonitrile in an organic solvent, such as p-dioxane, in the presence of a base, such as sodium hydride, at a temperature in the range of from about 0° C. up to ambient temperature to produce the acrylonitrile derivative XX; which can be reacted with a suitably substituted hydrazine (XVIII) or hydrate thereof, or acid-addition salt thereof, e.g. the hydrochloride, in the presence of a base, such as sodium methoxide, in an alcoholic solvent, such as ethanol, at a temperature in the range from ambient up to the boiling point of the solvent used to produce the 5-amino-1H-pyrazole-4-carbonitrile derivative XXI. This derivative can in turn be treated with a base, such as sodium hydroxide, in a solvent mixture consisting of an alcoholic solvent, such as ethanol, and water, at the reflux temperature of the solvent used to produce the desired compound of the Formula (II).

The lower-alkyl 5-amino-1H-pyrazole-4-carboxylate (VIII) may be synthesized by condensation of an appropriately substituted cyano-acrylic acid ester (XXII, Y=O or S), wherein YR is preferably methylthio, with a suitably substituted hydrazine (XVIII) or hydrate thereof, or acid-addition salt thereof, e.g. the hydrochloride, in the presence of a base, preferably sodium methoxide, in an alcoholic solvent, such as methanol, at a temperature in the range from about 50° C. up to the boiling point of the solvent used.

The appropriately substituted heterocyclylcarboxaldehyde (IV), heterocyclylcarboxylic acid halide (V), heterocyclylcarboxylic acid ($R^6$COOH), heterocyclylcarboxamidine (VI), heterocyclylcarboxylic acid ester (VII), heterocyclylcarbonitrile ($R^6$CN), heterocyclylimidate ester (XI), halide (XIII), malononitrile derivative (XVII), hydrazine (XVIII) pyridineacetate (XIX), and cyanoacrylic acid ester (XXII) are either commercially available or can be prepared by procedures well known in the art.

Simple chemical transformations which are conventional and well known to those skilled in the art of chemistry can be used for effecting changes in functional groups in the compounds of the invention. For example, partial hydrolysis of nitriles to produce the corresponding amides, complete hydrolysis of nitriles to produce the corresponding carboxylic acids, nitration of aromatic rings to produce the corresponding nitro species, catalytic reduction of nitro groups to produce the corresponding amino substituted compounds, sulfonylation or acylation of amino-substituted species to prepare the corresponding sulfonamides or amides, esterification of a carboxylic acid or acid halide to produce the corresponding ester, alkylation of heterocyclic nitrogen atoms to produce the corresponding N-alkylheterocycles, oxidation of heterocyclic nitrogen atoms to produce the corresponding N-oxides, reductive dehalogenation of heterocyclic halides, and displacement of heterocyclic halides with nucleophilic nitrogen containing heterocycles.

The compounds of Formula I are useful both in the free base form and in the form of acid-addition salts, and, both forms are within the purview of the invention. The acid-addition salts are often a more convenient form for use; and in practice, use of the salt form inherently amounts to use of the base form. The acids which can be used to prepare the acid-addition salts include preferably those which produce, when combined with the free base, pharmaceutically-acceptable salts, that is, salts whose anions are relatively innocuous to the animal organism in pharmaceutical doses of the salts, so that the beneficial properties inherent in the free base are not vitiated by side effects ascribable to the anions. In practicing the present invention it is convenient to use the free base form or the hydrochloride, fumarate, toluenesulfonate, methansulfonate or maleate salts. However, other appropriate pharmaceutically acceptable salts within the scope of the invention are those derived from other mineral acids and organic acids. The acid-addition salts of the basic compounds are prepared either by dissolving the free base in an aqueous alcohol solution containing the appropriate acid and isolating the salt by evaporating the solution, or by reacting the free base and an acid in an organic solvent, in which case the salt separates directly, is precipitated with a second organic solvent or can be obtained by concentration of the solution. Although medicinally acceptable salts of the basic compounds are preferred, all acid-addition salts are within the scope of the present invention. All acid-addition salts are useful as sources of the free base form even if the particular salt per se is desired only as an intermediate product, as, for example, when the salt is formed for purposes of purification or identification, or when it is used as an intermediate in preparing a medicinally acceptable salt by ion exchange procedures.

The structures of the compounds of the invention were established by the mode of synthesis, by elemental analysis, and by infrared, ultraviolet, nuclear magnetic resonance and mass spectroscopy. The course of the reactions and the identity and homogeneity of the products were assessed by thin layer chromatography (TLC) or gas-liquid chromatography (GLC).

The following examples will further illustrate the invention without, however, limiting it thereto. All melting points are given in degrees C and are uncorrected. The abbreviation THF stands for tetrahydrofuran, HCl stands for hydrochloric acid and DMF stands for N,N-dimethylformamide.

EXAMPLE 1

(a)

tert-Butyl 2-methylcyclopentylidinecarbazate

To a solution of 2-methylcyclopentanone (5.8 g, 59.5 mmol) in 85% n-hexanes (50 ml) was added tert-butyl carbazate (7.9 g, 59.5 mmol). The reaction mixture was heated to reflux for 24 hours, and was subsequently cooled to room temperature. The solution was filtered through filter paper and the product crystallized immediately from the filtrate. The crystalline residue was dissolved in chloroform and the solvents were removed in vacuo to afford 11 g (87%) of tert-butyl 2-methylcyclopentylidinecarbazate as a white powder.

(b)

2-Methylcyclopentylhydrazine hydrochloride

To a solution of tert-butyl 2-methylcyclopentylidinecarbazate (3.0 g, 14.1 mmol) in THF (15 ml) at room temperature was added sodium cyanoborohydride (1.4 g, 21.1 mmol) in THF (5 ml). The reaction mixture was stirred for 2 hours at room temperature, then 6N HCl (8 ml) was added dropwise. Upon complete addition of the 6N HCl, the reaction mixture was stirred at room temperature for 10 minutes and was then heated on a steam bath for 45 minutes. The reaction mixture was filtered through filter paper and the THF was removed in vacuo to afford a white slurry. This slurry was treated with methanol and ether to afford a white powder which was collected by filtration through a glass frit. The powder was washed with ether and the filtrate was concentrated in vacuo to afford 2.1 g (100%) of 2-methylcyclopentylhydrazine hydrochloride as a clear oil.

(c)

1-(2-Methylcyclopentyl)-3-methyl-5-amino-1H-pyrazole-4-carbonitrile

To a solution of 2-methylcyclopentylhydrazine hydrochloride (7.4 g, 48.8 mmol) in ethanol (100 ml) was added sodium methoxide (2.6 g, 48.8 mmol). The resulting white suspension was stirred for 10 minutes at room temperature and then (1-ethoxyethylidene)malononitrile (6.7 g, 48.8 mmol) was added. The reaction mixture was heated to reflux and was stirred for 5 hours. The solvent was removed in vacuo and the residue was partitioned between chloroform and water. The organic layer was separated and the aqueous layer was extracted with chloroform three times. The combined organic layers were washed with brine, then dried over anhydrous MgSO4. The solution was passed through a plug of silica gel and the solvent was removed in vacuo. The residue was washed with ether to afford 5.6 g (56%) of 1-(2-methylcyclopentyl)-3-methyl-5-amino-1H-pyrazole-4-carbonitrile as a white powder, m.p. 158°–159° C.

(d)

1-(2-Methylcyclopentyl)-3-methyl-5-amino-1H-pyrazole-4-carboxamide

85% Potassium hydroxide (5.8 g, 88.5 mmol) was dissolved in water (50 ml) and the solution was cooled in an ice bath for 1 hour. The 1-(2-methylcyclopentyl)-3-methyl-5-amino-1H-pyrazole-4-carbonitrile (2.6 g, 12.7 mmol) in methanol (5.0 ml)/water (25 ml) was then added, followed by 30% hydrogen peroxide (6.5 ml, 63.2 mmol). The reaction mixture was stirred with ice-bath cooling for 4 hours, then was warmed slowly to room temperature. Ethanol was added to the reaction mixture to completely dissolve the starting material and the mixture was stirred at room temperature for 60 hours. The ethanol was removed in vacuo and the oily residue was extracted with ethyl acetate (3×100 ml). The combined organic layers were dried over anhydrous MgSO4 and the solvents were removed in vacuo to afford an amber solid. Recrystallization from acetonitrile and air drying then afforded 2.4 g (84%) of 1-(2-methylcyclopentyl) -3-methyl-5-amino-1H-pyrazole-4-carboxamide as an off-white solid, m.p. 124°–126° C.

(e)

1-(2-Methylcyclopentyl)-3-methyl-6-(4-pyridyl) pyrazolo [3,4-d]pyrimidin-4-one To a solution of 1-(2-methylcyclopentyl)-3-methyl-5-amino-1H-pyrazole-4-carboxamide (2.3 g, 10.4 mmol) in xylenes (8.0 ml) under argon was added 4-pyridinecarboxaldehyde (1.5 ml, 15.5 mmol). The reaction mixture was warmed to 120° C. and stirred for 1 hour at which time the mixture became homogeneous. The reaction mixture was then heated to 160° C. for 24 hours and then cooled to room temperature. A solid precipitated which was collected by filtration through a glass frit. The solid was washed with ether, saturated $NaHCO_3$ then water and was recrystallized from DMF. The solid was collected on a glass frit and was washed with methanol, then ether and dried at 110° C. for 72 hours in high vacuum to afford 1.05 g (33%) of 1-(2-methylcyclopentyl)-3-methyl-6-(4-pyridyl)-pyrazolo [3,4-d]pyrimidin-4-one as white crystals, m.p. 290°–291° C.

EXAMPLE 2

(a)

tert-Butyl cyclopentylidinecarbazate

To a solution of cyclopentanone (42.1 g, 0.5 moles) in hexanes (1000 ml) at room temperature was added tert-butyl carbazate (66.1 g, 0.5 moles). The reaction mixture was stirred at room temperature for 30 minutes, then refluxed on a steam bath for 30 minutes. The solution was cooled in an ice bath and the product was isolated by filtration and air dried to afford 93.3 g (94%) of tert-butyl cyclopentylidinecarbazate as white crystals, m.p. 119°–121° C.

(b)

Cyclopentylhydrazine hydrochloride tert-Butyl cyclopentylidinecarbazate (93.3 g, 0.47 mol), THF (370 ml), methanol (500 ml) and sodium cyanoborohydride (34.3 g, 0.55 mole) were combined and the resulting yellow solution was stirred at room temperature for 1 hour. 6N HCl (330 ml) was added dropwise to the reaction mixture over 55 minutes. The reaction mixture was then refluxed for 1 hour and subsequently cooled to room temperature. The solution was filtered through filter paper and the filtrate was concentrated in vacuo. Toluene and ethanol were added to the residue and the solvents were removed in vacuo to afford an oily residue. The residue was crystallized from isopropanol and ether to afford 93.1 g (94%) of cyclopentylhydrazine hydrochloride, m.p. 90°–92° C.

(c)

(1-Ethoxypropylidene)malononitrile

Triethyl orthopropionate (1000 g, 5.5 mole) and malononitrile (363 g, 5.5 mole) were combined and refluxed for 5 hours. The reaction mixture was cooled to room temperature and the residue was distilled at 125°–143° C. (3–7 mm Hg) to afford 768.1 g (93%) of (1-ethoxypropylidene)malononitrile as an orange liquid.

(d)

1-Cyclopentyl-3-ethyl-5-amino-1H-pyrazole-4-carbonitrile

Cyclopentylhydrazine hydrochloride (20.9 g, 0.1 moles), 97% sodium methoxide (5.6 g, 0.1 moles) and ethanol (100 ml) were combined and stirred at room temperature under argon for 2.5 hours. (1-Ethoxypropylidene)malononitrile was added to the reaction mixture and the mixture was refluxed for 21 hours. The reaction mixture was cooled and the solvent was removed in vacuo. The residue was treated with water (150 ml) and the obtained precipitate was collected by filtration, washed with water and dried in a vacuum oven for 24 hours to afford 14.2 g (70%) of 1-cyclopentyl-3-ethyl-5-amino-1H-pyrazole-4-carbonitrile as a brown powder, m.p. 171°–173° C.

(e)

1-Cyclopentyl-3-ethyl-5-amino-1H-pyrazole-4-carboxamide

To concentrated sulfuric acid (50 ml) cooled in an ice/sodium chloride bath was added in small portions 1-cyclopentyl-3-ethyl-4-cyano-5-amino-1H-pyrazole. The reaction mixture was warmed to room temperature and stirred for 24 hours. The reaction mixture was slowly added to a solution of concentrated ammonium hydroxide (150 ml) in ice-water (500 ml). A yellow precipitate formed which was collected by filtration, washed with water and dried at 90° C. for 60 hours in high vacuum to afford 3.47 g (85%) of 1-cyclopentyl-3-ethyl-5-amino-1H-pyrazole-4-carboxamide, m.p. 167°–168° C.

(f)

1-Cyclopentyl-3-ethyl-6-(3-methyl-2-pyridyl)pyrazolo [3,4-d]pyrimidin-4-one

1-Cyclopentyl-3-ethyl-5-amino-1H-pyrazole-4-carboxamide (2.0 g, 9.0 mmol), 6-methyl-2-pyridinecarboxaldehyde (2.2 g, 18.0 mmol), methanesulfonic acid (0.5 ml) and xylenes (80 ml) were combined and heated to reflux for 24 hours. The solvents were removed in vacuo, ethanol was added and the solvents were removed in vacuo. The residue was partitioned between 10% $K_2CO_3$ and chloroform, the organic layer was separated and the aqueous layer was extracted with chloroform (3×200 ml). The combined organic layers were concentrated in vacuo, redissolved in dichloromethane and combined with silica gel (40 g). The slurry was air dried for 3 hours, and placed on a silica gel column (150 g). Elution with ether and concentration of the solvent in vacuo and drying the residue at 40° C. in high vacuum for 6 hours afforded 1.55 g (53%) of 1-cyclopentyl-3-ethyl-6-(6-methyl-2-pyridyl)-pyrazolo-[3,4-d]pyrimidin-4-one.

It is contemplated that following the procedures of Example 2 but starting with 2-quinoxalinecarboxaldehyde, 2-pyrrolecarboxaldehyde, or 3-indolecarboxaldehyde in place of 6methyl-2-pyridinecarboxaldehyde there can be prepared 1-cyclopentyl-3-ethyl-6-(2-quinoxalyl)-pyrazolo [3,4-d]pyrimidin-4-one, 1-cyclopentyl-3-ethyl-6-(2-pyrrolyl)pyrazolo[3,4-d]-pyrimidin-4-one, and 1-cyclopentyl-3-ethyl-6-(3-indolyl) pyrazolo[3,4-d]pyrimidin-4-one.

EXAMPLE 3

Following the procedures of Example 1, parts (a), (b) and (c), but substituting cyclohexanone for the 2-methyl cyclopentanone of Example 1, part (a) and borane-tetrahydrofuran complex for the sodium cyanoborohydride of Example 1, part (b), there were obtained the following:

(a)

tert-Butyl cyclohexylidinecarbazate, 100% yield, white solid.

(b)

Cyclohexylhydrazine hydrochloride, 72% yield, white crystals.

(c)

1-Cyclohexyl-3-methyl-4-cyano-5-amino-1H-pyrazole, 33% yield, tan crystals, m.p. 159°–160° C.

(d)

1-Cyclohexyl-3-methyl-5-amino-1H-pyrazole-4-carboxamide.

To concentrated sulfuric acid (50 ml) at 0° C. was added 1-cyclohexyl-3-methyl-4-cyano-5-amino-1H-pyrazole (2.2 g, 10.8 mmol). The reaction mixture was warmed to room temperature and stirred for 24 hours. The solution was poured into ice/concentrated ammonium hydroxide, the solution was then neutralized with acetic acid and extracted with dichloromethane (2×400 ml). The solvent was removed in vacuo, the residue was extracted with ethyl acetate (75 ml) and treated with DARCO. The solution was filtered, the solvent was removed in vacuo and the residue was dissolved in ether and cooled. A precipitate was obtained which was collected by filtration, washed with ether and dried at 50° C. in high vacuum for 60 hours to afford 1.83 g (76%) of 1-cyclohexyl-3-methyl-5-amino-1H-pyrazole-4-carboxamide as yellow needles, m.p. 181°–182° C.

(e)

1-Cyclohexyl-3-methyl-6-(4-pyridyl)-pyrazolo[3,4-d]pyimidin-4-one

1-Cyclohexyl-3-methyl-5-amino-1H-pyrazole-4-carboxamide (1.2 g, 5.4 mmol), 4-pyridinecarboxaldehyde (0.87 g, 8.1 mmol), toluene (125 ml) and p-toluenesulfonic acid monohydrate were combined and heated to reflux for 24 hours. The solvent was removed in vacuo and the residue was poured into water (450 ml). The obtained precipitate was collected by filtration, recrystallized from isopropanol (200 ml) and dried for 24 hours in high vacuum to afford 0.53 g (32%) of 1-cyclohexyl-3-methyl-6-(4-pyridyl)-pyrazolo[3,4-d]pyrimidin-4-one as a cream colored solid, m.p. 292°–293° C.

EXAMPLE 4

(a)

(1-Hydroxy-(3,4-dimethoxyphenylethylidene))malononitrile

To a 60% NaH/mineral oil dispersion (6.0 g, 0.15 moles) in THF (230 ml) in an ice-bath was added dropwise malononitrile (9.9 g, 0.15 mol). The reaction mixture was stirred for 2 hours at 0° C. and 3,4-dimethoxyphenyl acetylchloride (32.2 g, 0.15 mol) in THF (50 ml) was added dropwise over 2 hours. The reaction mixture was warmed to room temperature and stirred for 24 hours. The solvent was removed in vacuo, and the residue was partitioned between chloroform and 2N $H_2SO_4$. The organic layer was separated and the aqueous layer was extracted with chloroform (2×150 ml). The organic layers were combined and the solvent was removed in vacuo to afford 40.4 g (crude) of (1-hydroxy-(3,4-dimethoxyphenylethylidene))malononitrile as a brown oil, which was used directly in the following reaction without purification.

(b)

(1-Methoxy-(3,4-dimethoxyphenylethylidene))malononitrile

To 60% NaH (5.7 g, 0.14 mol) in THF (150 ml) at −78° C. under argon was added dropwise (1-hydroxy-(3,4-dimethoxyphenylethylidene), malononitrile (34.6 g, 0.14 mol) in THF (100 ml) over 1.25 hours. The reaction mixture was stirred for 2 hours and dimethyl sulfate (26.9 g, 0.21 mol) in THF (50 ml) was added over 30 minutes. The reaction mixture was warmed to room temperature and stirred for 24 hours. The solvents were removed in vacuo and the residue was partitioned between ether and water. The organic layer was separated and the aqueous layer was extracted with ether (3×150 ml). The ether layers were combined and the solvent was removed in vacuo. The residue was purified by column chromatography on silica gel eluting with hexane/ether (6/4) to afford crude (1-methoxy-(3,4-dimethoxyphenylethylidene))malononitrile as a gold oil.

Following the procedure of Example 1, part C, but substituting tert-butylhydrazine hydrochloride for 2-methylcyclopentylhydrazine hydrochloride and (1-methoxy-(3,4-dimethoxyphenylethylidene), malononitrile for (1-ethoxyethylidene)malononitrile there was obtained:

(c)

1-tert-Butyl-3-(3, 4-dimethoxybenzyl)-5-amino-1H-pyrazole-4-carbonitrile, 57% yield, clear crystals, m.p. 138°–139° C.

Following the procedure of Example 1, part d, but substituting 1-tert-butyl-3-(3,4-dimethoxybenzyl)-5-amino-1H-pyrazole-4-carbonitrile for 1-(2-methyl-cyclopentyl)-3-methyl-5-amino-1H-pyrazole-4-carbonitrile and ethanol for methanol there was obtained, after column chromatography on silica gel eluting with hexane/ether (1/1):

(d)

1-tert-Butyl-3-(3,4-dimethoxybenzyl )-5-amino-1H-pyrazole-4-carboxamide, 32% yield, red crystals, m.p. 53°–56° C.

Following the procedure of Example 3, part e, but substituting 1-tert-butyl-3-(3,4-dimethoxybenzyl)-5-amino-1H-pyrazole-4-carboxamide for 1-cyclohexyl-3-methyl-5-amino-1H-pyrazole-4-carboxamide, and xylenes for toluene and ethanol for water there was obtained:

(e)

1-tert-Butyl-3-(3,4-dimethoxybenzyl )-6-(4-pyridyl )pyrazolo[3,4-d]pyrimidin-4-one, 83% yield, white crystals, m.p. 202°–203° C., when recrystallized from ethyl acetate.

EXAMPLE 5

Following the procedure of Example 4, parts a, b and c, but substituting cyclohexylacetyl chloride for 3,4-dimethoxyphenylacetyl chloride, 97% NaH/mineral oil dispersion for 60% NaH/mineral oil dispersion and 2N HCl for 2N $H_2SO_4$ in Example 4, part a; 97% NaH/mineral oil dispersion for 60% NaH/mineral oil dispersion in Example 4, part b and refluxing for 24 hours; and ethyl acetate for chloroform in Example 4, part C, there were obtained the following:

(a)

(1-Hydroxy-cyclohexylethylidene) malononitrile, 93% yield, amber oil.

(b)

(1-Methoxy-cyclohexylethylidene) malononitrile, 94% yield, dark oil, after column chromatography on silica eluting with hexane/ethyl acetate (75/25).

(c)

1-tert-Butyl-3-(cyclohexylmethyl)-5-amino-1H-pyrazole-4-carbonitrile, 27% yield, clear crystals, m.p. 106°–107° C. when recrystallized from hexane.

(d)

1-tert-Butyl-3-(cyclohexylmethyl)-5-amino-1H-pyrazole-4-carboxamide.

To potassium hydroxide (4.95 g, 0.09 mol) in 50% water/ethanol (83 ml) was added 30% hydrogen peroxide (6.7 ml, 0.06 mol) followed by 1-tert-butyl-3-(cyclohexylmethyl)-5-amino-1H-pyrazole-4-carbonitrile (2.8 g, 0.01 mol). The reaction mixture was stirred at room temperature for 24 hours, then was heated on a steam bath for 4 hours. More 30% hydrogen peroxide was added (6.5 ml, 0.057 mol) and the reaction mixture was heated for an additional 2 hours. The solvent was removed in vacuo, water was added and the residue was extracted with ethyl acetate (2×). The organic layer was washed with brine, dried over anhydrous $MgSO_4$ and the solvent was removed in vacuo. The residue was purified by preparative thin layer chromatography on silica eluting with ethyl acetate (100%) to afford 0.34 g (11%) of 1-tert-butyl-3-(cyclohexylmethyl)-5-amino-1H-pyrazole-4-carboxamide as an amber oil.

Following the procedures of Example 1, part e, but substituting 1-tert-butyl-3-(cyclohexylmethyl)-5-amino-1H-pyrazole-4-carboxamide for 1-(2-methyl-cyclopentyl)-3-methyl-5-amino-1H-pyrazole-4-carboxamide, and working up the reaction by cooling the reaction mixture, adding ethyl acetate, and collecting the obtained solid by filtration there was obtained:

(e)

1-tert-Butyl-3-( cyclohexylmethyl )-6-(4-pyridyl)-pyrazolo[3,4-d]pyrimidin-4-one, 34% yield, tan solid, m.p. 260°–262° C. when recrystallized from ethyl acetate.

EXAMPLE 6

(a)

3,3-Bis(methylthio)-2-cyanoacrylonitrile

To sodium methoxide (95 g, 1.8 mol) in methanol (1300 ml) at 5° C. was added malononitrile (66 g, 1.0 mol) followed by dropwise addition of carbon disulfide (76.8 g, 1.0 mol). The reaction mixture was stirred at 5° C. for 20 minutes then dimethylsulfate (225 g, 2 mol) was added dropwise. The reaction mixture was stirred at 5° C. for 24 hours, then was heated on a steam both for 45 minutes. The reaction mixture was cooled, poured into ice-water (3000 ml) and the obtained precipitate was collected by filtration and air dried to afford 18.6 g (11%) of 3,3-bis(methylthio)-2-cyanoacrylonitrile as an orange powder.

(b)

(1-Thiomethyl-phenylaminomethylidene) malononitrile 3,3-bis(methylthio)-2-cyanoacrylonitrile (9.9 g, 0.06 mol) and aniline (5.8 ml, 0.06 mol) in ethanol (37 ml) were heated to reflux for 2 hours. The reaction mixture was cooled and the obtained precipitate was isolated by filtration and washed with ethanol to afford 11.7 g (94%) of (1-Thiomethylphenylaminomethylidene)malononitrile as orange crystals.

(c)

1-tert-Butyl-3-phenylamino-5-amino-1H-pyrazole-4-carbonitrile

To tert-butyl hydrazine hydrochloride (6.9 g, 0.056 mol) in methoxyethanol (85 ml) was added sodium methoxide (3.0 g, 0.056 mol). The reaction mixture was stirred for 15 minutes, cooled in an ice bath and the precipitate obtained was collected by filtration. This precipitate was then added to (1-thiomethylphenylaminomethylidene)malononitrile (12.0 g, 0.056 mol) in methoxyethanol (85 ml). The reaction mixture was heated to reflux and was stirred for 24 hours. The solvent was removed in vacuo and the residue was purified by column chromatography on silica eluting with hexanes/ethyl acetate (1/1) to afford 2.2 g (16%) of 1-tert-butyl-3-phenylamino-5-amino-1H-pyrazole-4-carbonitrile, m.p. 123°–125° C. when recrystallized from ether/hexanes.

(d)

1-tert-Butyl-3-phenylamino-5-amino-1H-pyrazole-4-carboxamide 1-tert-Butyl-3-phenylamino-5-amino-1H-pyrazole-4-carbonitrile (1.0 g, 0.004 mol), 50% aqueous ethanol (30 ml), potassium hydroxide (1.8 g, 0.03 mol) and 30% hydrogen peroxide (2.5 ml, 0.02 mol) were combined and stirred at room temperature for 24 hours, then refluxed on a steam bath for 1 hour. The reaction mixture was added to water, and the obtained solid was filtered and washed with water to afford 0.68 g (64%) of 1-tert-butyl-3-phenylamino-5-amino-1H-pyrazole-4-carboxamide as a gray solid, m.p. 225°–227° C.

Following the procedure of Example 5, part e, but substituting 1-tert-butyl-3-phenylamino-5-amino-1H-pyrazole-4-carboxamide for 1-tert-butyl-3-(cyclohexylmethyl)-5-amino-1H-pyrazole-4-carboxamide there was obtained:

(e)

1-tert-Butyl-3-phenylamino-6-(4-pyridyl )-pyrazolo[3,4-d]-pyrimidin-4-one, 37% yield, yellow powder, m.p. >300° C. when recrystallized from ethyl acetate and dried in high vacuum at 110° C. for 72 hours.

EXAMPLE 7

(a)

4-Quinolinecarboxylic acid chloride hydrochloride

To 4-quinolinecarboxylic acid (5.0 g, 29.1 mmol) at 0° C. under argon was added thionyl chloride (20.0 ml, 0.27 mol). The reaction mixture was slowly warmed to room temperature and stirred for 1 hour. Dichloromethane (100 ml) was added and the reaction mixture was refluxed for 3 hours. The solvents were removed by distillation and the residue was dried at 130° C. in high vacuum to afford 5.8 g (87%) of 4-quinolinecarboxylic acid chloride hydrochloride as green crystals, m.p. 249°–251° C.

(b)

1-Cyclopentyl-3-ethyl-4-cyano-5-(4-quinolinecarboxamido)-1H-pyrazole

4-Quinolinecarboxylic acid chloride hydrochloride (3.8 g, 16.5 mmol) and 1-cyclopentyl-3-ethyl-5-amino-1H-pyrazole-4-carbonitrile (2.8 g, 13.7 mmol) were combined and heated in an oil bath at 250° C. for 7 minutes. The reaction mixture was cooled to room temperature and the obtained solid was collected by filtration on a glass frit and was washed with chloroform. The residue was recrystallized from ethyl acetate to afford 5.0 g (100%) of 1-cyclopentyl-3-ethyl-4-cyano-5-(4-quinoline-carboxamido)-1H-pyrazole as a white solid, m.p. 156°–161° C., after drying at 110° C. for 7 hours in high vacuum.

(c)

1-Cyclopentyl-3-ethyl-6-(4-quinolinyl)-pyrazolo[3,4-d]pyrimidin-4-one

To a mixture of 1-cyclopentyl-3-ethyl-4-cyano-5-(4-quinolinecarboxamido)-1H-pyrazole (4.6 g, 12.7 mmol), potassium hydroxide (1.7 g, 25.4 mmol) and water (250 ml) at room temperature was added 30% hydrogen peroxide (7.8 ml, 76.0 mmol). The reaction mixture was heated to reflux and stirred for 24 hours. One equivalent of potassium hydroxide and 2 equivalents of 30% hydrogen peroxide were added and the mixture was refluxed for another 24 hours. One equivalent of potassium hydroxide and 2 equivalents of 30% hydrogen peroxide were again added and the mixture was heated at reflux for 3 days. The reaction mixture was cooled to room temperature, treated with acetic acid until a pH of 6.5 was obtained and the resulting precipitate was collected by filtration. The product was purified by column chromatography on silica eluting with ethyl acetate to afford 1.3 g (34%) of 1-cyclopentyl-3-ethyl-6-(4-quinolinyl)-pyrazolo[3,4-d]pyrimidin-4-one as a white solid, m.p. 205°–206° C., when recrystallized from ethyl acetate and dried at 110° C. for 16 hours in high vacuum.

It is contemplated that following a procedure substantially similar to that described in Example 7 but starting with 2-pyrazine carboxylic acid chloride or 5-benzimidazole carboxylic acid chloride in place of 4-quinoline carboxylic acid chloride there can be prepared 1-cyclopentyl-3-ethyl-6-(2-pyrazinyl)-pyrazolo[3,4-d]pyrimidin-4-one and 1-cyclopentyl-3-ethyl-6-(5-benzimidazolyl)-pyrazolo [3,4-d]pyrimidin-4-one.

EXAMPLE 8

1-Cyclopentyl-3-ethyl-6-(perhydro-4-quinolinyl)-pyrazolo[3,4-d]pyrimidin-4-one 1-Cyclopentyl-3-ethyl-6-(4-quinolinyl)-pyrazolo[3,4-d]-pyrimidin-4-one (1.0 g, 2.7 mmol), platinum oxide (0.15 g) and acetic acid (50 ml) were combined and placed in a parr hydrogenator at 42 psi. The reaction mixture was heated at about 70° C. by an external heating jacket for 6 hours. The reaction mixture was cooled to room temperature, the catalyst was removed by filtration through a celite pad and the pad was washed with ethanol. Concentrated HCl (3 ml) was added to the filtrate and the solvents were removed in vacuo. The residue was dissolved in isopropanol (10 ml) and was heated on a steam bath for 10 minutes. A solid was collected by filtration, washed with isopropanol and dried at 90° C. in high vacuum to afford 0.83 g (84%) of 1-cyclopentyl-3-ethyl-6-(perhydro-4-quinolinyl)pyrazolo[3,4-d]pyrimidin-4-one as a white powder, m.p. >300° C.

Following the procedure of Example 8 but heating the reaction mixture at about 50° C. there was obtained:

EXAMPLE 9

1-Cyclopentyl-3-ethyl-6-(1,2,3,4-tetrahydro-4-quinolinyl)-pyrazolo[3,4-d]pyrimidin-4-one, 53% yield, white powder, m.p. 159° 161° C. when recrystallized from cyclohexane and dried at 85° C. in high vacuum.

EXAMPLE 10

1-Cyclopentyl-3-ethyl-6-(1,2,3,4-tetrahydro- 4-n-methyl-quinolinyl)-pyrazolo[3,4-d]pyrimidin-4-one and 1-Cyclopentyl-3-ethyl-6-(perhydro-4-n-methylquinolinyl)pyrazolo [3,4-d]pyrimidin-4-one.

(a)

To a solution of 1-cyclopentyl-3-ethyl-6-(4-quinolinyl)pyrazolo[3,4-d]pyrimidin-4-one (1.4 g, 3.8 mmol) in toluene (50 ml) was added dimethylsulfate (1.0 ml, 11.0 mmol). The reaction mixture was heated on a steam bath for 4.5 hours and the solvent was removed in vacuo. The residue was dissolved in ethanol (100 ml), platinum oxide (0.10 g) was added and the mixture was placed on a parr hydrogenator with external heating at about 50° C. via a heating jacket at 45 psi for 6 hours. The catalyst was removed by filtration through celite and the filtrate was concentrated in vacuo. The residue was partitioned between chloroform (100 ml) and 10% aqueous $K_2CO_3$ (50 ml) and the organic layer was separated. Removal of the solvent in vacuo and crystallization of the residue from hexanes/ether afforded 0.62 g (42%) of 1-cyclopentyl-3-ethyl-6-(perhydro-4-N-methyl-quinolinyl)-pyrazolo-[3,4-d]pyrimidin-4-one as a white solid, m.p. 206°–210° C. after drying at 85° C. in high vacuum.

(b)

The mother liquor from the above recrystallization was chromatographed on silica eluting with ether to afford 0.13 g (9%) of 1-cyclopentyl-3-ethyl-6-(1,2,3,4-tetrahydro-4-N-methyl-quinolinyl)-pyrazolo-[3,4-d]pyrimidin-4-one as a white solid, m.p. 156°–158° C. when recrystallized from hexanes and dried at 85° C. in high vacuum. Alternatively, this product can be prepared directly by following the above procedure and substituting ethanol/acetic acid (9/1) for ethanol and maintaining the reaction mixture at room temperature during the hydrogenation step. In this manner one obtains the product in 17% yield.

Following the procedure of Example 2, parts a, b and d, but substituting (1-ethoxyethylidene)malononitrile for (1-ethoxypropylidene)malononitrile in part d there was obtained:

EXAMPLE 11

1-Cyclopentyl-3-methyl-5-amino-1H-pyrazole-4-carbonitrile, 54% yield, off-white powder, m.p. 141°–142 ° C. when recrystallized from cyclohexane

EXAMPLE 12

(a)

8-Quinolinecarboxylic acid chloride hydrochloride

To 8-quinolinecarboxylic acid (10.0 g, 57.8 mmol) in an ice/methanol bath was added thionyl chloride (90.0 ml, 123.4 mmol) in one portion. The reaction mixture was slowly warmed to room temperature and was stirred for 24 hours. Dichloromethane (100 ml) was added and the reaction mixture was refluxed for 1 hour. The solvents were removed by distillation under reduced pressure and the residue was dried for 24 hours at 80° C. in high vacuum to afford 12.6 g (96%) of 8-quinolinecarboxylic acid chloride hydrochloride as a tan powder, m.p. 232°–237° C.

Following the procedure of Example 7, part b, but substituting 8-quinolinecarboxylic acid chloride hydrochloride for 4-quinolinecarboxylic acid chloride hydrochloride and 1-cyclopentyl-3-methyl-5-amino-1H-pyrazole-4-carbonitrile for 1-cyclopentyl-3-ethyl-5-amino-1H-pyrazole-4-carbonitrile there was obtained:

(b)

1-Cyclopentyl-3-methyl-4-cyano-5-(8-quinoline-carboxamide)-1H-pyrazole, 63% yield, pale-yellow crystals, m.p. 143°–144° C. when purified by column chromatography on silica eluting with ethanol and recrystallized from ethyl acetate.

(c)

1-Cyclopentyl-3-methyl-6-(8-quinolinyl)-pyrazolo-[3,4-d]pyrimidin-4-one

To potassium hydroxide (0.2 g, 3.0 mmol) in water (75 ml) cooled in an ice bath was added 1-cyclopentyl-3-methyl-4-cyano-5-(8-quinolinecarboxamido)-1H-pyrazole (2.05 g, 5.9 mmol) in methanol (30 ml) followed by 30% hydrogen peroxide (3.0 ml, 30 mmol). The reaction mixture was slowly warmed to room temperature and then refluxed for 24 hours. Additional potassium hydroxide (3.0 mmol) and 30% hydrogen peroxide (30 mmol) were added and the reaction mixture was refluxed for 1.5 hours. The reaction mixture was cooled in an ice-bath, the precipitated product was collected by filtration through a glass frit and was washed with water, then ether. Recrystallization from ethyl acetate afforded 0.2 g (10%) of 1-cyclopentyl-3-methyl-6-(8-quinolinyl)-pyrazolo[3,4-d]pyrimidin-4-one as yellow crystals, m.p.242°–244° C. when dried for 24 hours at 120° C. in high vacuum.

Following the procedure of Example 12, part b, but substituting 4-quinolinecarboxylic acid chloride hydrochloride for 8-quinolinecarboxylic acid chloride hydrochloride, heating to 220° C. rather than 250° C. and washing with chloroform/ethanol rather than chloroform there was obtained:

EXAMPLE 13

(a)

1-Cyclopentyl-3-methyl-4-cyano-5-(4-quinolinecarboxamido)-1H-pyrazole, 69% yield, white crystals, m.p. 175°–176° C. when recrystallized from ethyl acetate and dried for 24 hours at 100° C. in high vacuum.

Following the procedure of Example 7, part c, but substituting 1-cyclopentyl-3-methyl-4-cyano-5-(4-quinolinecarboxamido)-1H-pyrazole for 1-cyclopentyl-3-ethyl-4-cyano-5-(4quinolinecarboxamido)-1H-pyrazole and making no subsequent additions of potassium hydroxide or 30% hydrogen peroxide there was obtained:

(b)

1-Cyclopentyl-3-methyl-6-(4-quinolinyl)-pyrazolo [3,4-d]-pyrimidin-4-one, 55%, white powder, m.p. 253°–254° C. when recrystallized from methanol and dried for 24 hours in high vacuum.

Following the procedure of Example 7, parts a, b and c, but substituting 6-quinolinecarboxylic acid for 4-quinolinecarboxylic acid in part a; substituting 6-quinolinecarboxylic acid chloride hydrochloride for 4-quinolinecarboxylic acid chloride hydrochloride, working up the reaction by partitioning the mixture between chloroform and water, separating out the organic layer, extracting the aqueous layer with chloroform (3×150 ml), combining the organic layers, washing with sat. NaHCO$_3$, then brine, drying the organic layer over anhydrous MgSO$_4$ and removing the solvent in vacuo in part b; and substituting 1-cyclopentyl- 3-methyl-4-cyano-5-(6-quinolinecarboxamido)-1H-pyrazole for 1-cyclopentyl-3-ethyl-4-cyano-5-(4-quinoline-carboxamido)-1H-pyrazole and making no subsequent additions of potassium hydroxide or 30% hydrogen peroxide, in part c, there was obtained:

EXAMPLE 14

(a)

6-Quinolinecarboxylic acid chloride hydrochloride, 100% yield, creamy white powder.

(b)

1-Cyclopentyl-3-methyl-4-cyano-5-(6-quinolinecarboxamido)-1H-pyrazole, 49% yield, white solid, m.p. 205°–207° C. when recrystallized from acetonitrile, then ethyl acetate and dried for 8 hours at 120° C. in high vacuum.

(c)

1-Cyclopentyl-3-methyl-6-(6-quinolinyl)-pyrazolo [3,4-d]-pyrimidin-4-one, 86% yield, white crystals, m.p. 261°–262° C. when dried for 16 hours at 125° C. in high vacuum.

EXAMPLE 15

(a)

(1-Hydroxy-2-phenylethylidene)malononitrile

To 60% NaH/mineral oil dispersion (3.2 g, 79.5 mmol) in THF (100 ml) at room temperature under argon was added dropwise malononitrile (5.0 ml, 79.5 mmol) in THF (20 ml) over 30 minutes. The reaction mixture was stirred at room temperature for 30 minutes, then phenylacetyl chloride (10.5 ml, 79.5 mmol) in THF (10 ml) was added dropwise over 10 minutes. The reaction mixture was stirred at room temperature for 1.5 hours, the solvent was removed in vacuo, and the residue was partitioned between ether and 2N $H_2SO_4$. The ether layer was separated, washed with water, dried over anhydrous $MgSO_4$, filtered through a silica gel plug and the solvent was removed in vacuo to afford 13.8 g (94%) of (1-hydroxy-2-phenylethylidene)malononitrile as an amber oil.

(b)

(1-Methoxyphenylethylidene)malononitrile

To a suspension of 60% NaH/mineral oil dispersion (2.9 g, 74.7 mmol) in THF (50 ml) was added dropwise (1-hydroxyphenylethylidene)malononitrile (13.8 g, 74.7 mmol) in THF (75 ml) over 25 minutes, followed by dimethylsulfate (7.1 ml, 74.7 mmol) in THF (50 ml) over 20 minutes. The reaction mixture was stirred at room temperature for 30 minutes, then at reflux for 4 hours. 0.5 equivalents of 60% sodium hydride and dimethylsulfate were added and the reaction mixture was stirred at room temperature for 24 hours. The solvent was removed in vacuo, the residue was partitioned between ether and water, the organic layer was separated and the aqueous layer was extracted with ether (3×150 ml). The combined organic layers were dried over anhydrous $MgSO_4$ and solvent was removed in vacuo. The residue was purified by column chromatography on silica eluting with ethyl acetate/hexanes (1/1) to afford 8.4 g (56%) of (1-methoxyphenylethylidene)malononitrile as an amber liquid.

(c)

1-Cyclopentyl-3-phenylmethyl-5-amino-1H-pyrazole-4-carbonitrile

A mixture of cyclopentyl hydrazine hydrochloride (1.4 g, 10.2 mmol), sodium methoxide (0.55 g, 10.2 mmol) and ethanol (30 ml) was heated to reflux and then (1-methoxyphenylethylidene)malononitrile (2.0 g, 10.2 mmol) in ethanol (15 ml) was added dropwise over 1 hour. The reaction mixture was refluxed for 6.5 hours and the solvent was removed in vacuo. The residue was partitioned between chloroform and water, the organic layer was separated and the aqueous layer was extracted with chloroform (3×75 ml). The combined organic layers were washed with brine, dried over anhydrous $MgSO_4$ and concentrated in vacuo to afford 0.7 g (26%) of 1-cyclopentyl-3-phenylmethyl-5-amino-1H-pyrazole-4-carbonitrile as white flakes, m.p. 180°–182° C. when recrystallized from ethyl acetate and dried for 18 hours at 90° C. in high vacuum.

(d)

1-Cyclopentyl-3-phenylmethyl-4-cyano-5-(4-pyridinecarboxamido)-1H-pyrazole

4-Pyridinecarboxylic acid chloride hydrochloride (4.3 g, 24 mmol), and 1-cyclopentyl-3-phenylmethyl-4-cyano-5-amino-1H-pyrazole (3.2 g, 12.0 mmol) were combined and heated to 200° C. under argon for 5 minutes. The reaction mixture was cooled to room temperature and the residue was partitioned between chloroform and sat. $NaHCO_3$. The organic layer was separated, washed with additional sat. $NaHCO_3$, dried over anhydrous $MgSO_4$ passed through a plug of silica and the solvent was removed in vacuo to afford 3.8 g (84%) of 1-cyclopentyl-3-phenylmethyl-4-cyano-5-(4-pyridinecarboxamido)-1H-pyrazole as white crystals, m.p. 189°–191° C. when recrystallized from ethyl acetate and dried at 80° C. for 8 hours in high vacuum.

Following the procedure of Example 7, part c, but substituting 1-cyclopentyl-3-phenylmethyl-4-cyano-5-(4-pyridinecarboxamido)-1H-pyrazole for 1-cyclopentyl-3-ethyl-4-cyano-5-(4-cyano-(4-quinolinecarboxamido)-1H-pyrazole and using ethanol/water (10/1) rather than ethanol, there was obtained:

(e)

1-Cyclopentyl-3-phenylmethyl-6-(4-pyridyl)-pyrazolo[3,4-d]pyrimidin-4-one, 9% yield, white crystals, m.p. 292°–293° C. when recrystallized from ethanol and dried at 120° C. for 16 hours in high vacuum.

EXAMPLE 16

(a)

2-Amino-5-pyridinecarboxylic acid ethyl ester

To 2-amino-5-pyridine carboxylic acid (10.1 g, 73.0 mmol) in DMF (100 ml) at room temperature under argon was added potassium carbonate (10.1 g, 73.0 mmol) followed by ethyl iodide (8.8 ml, 110.0 mmol) 15 minutes later. The reaction mixture was heated on a steam bath for 2 hours, then additional potassium carbonate (2.0 g) and ethyl iodide (4.4 ml) were added. The reaction mixture was heated on a steam bath for 60 hours, cooled to room temperature and stirred for 24 hours. The reaction mixture was warmed on a steam bath for 20 minutes, the solution was filtered and the filtrate was concentrated in vacuo. The residue was taken up in water (350 ml), the solution was chilled and the precipitate that was obtained was collected by filtration and air dried. The filtrate was extracted with chloroform (3×200 ml), the organic layers were combined, dried over anhydrous $MgSO_4$ and the solvents were removed in vacuo. Ether was added to the residue and the solution was chilled for 24 hours. The resulting white precipitate was collected by filtration, air-dried dried and combined with the previously collected precipitate to afford 6.2 g (51%) of 2-amino-5-pyridinecarboxylic acid ethyl ester as a white solid.

(b)

6-Carboethoxyimidazo[1,2-a]pyridine

A mixture of 2-amino-5-pyridine carboxylic acid ethyl ester (4.5 g, 27.1 mmol), chloroacetaldehyde (5.7 ml, 40.6 mmol, 45% w/w in water) and toluene (125 ml) was heated to reflux and water was collected in a Dean Stark trap. After 3 hours at reflux the reaction mixture was cooled to room temperature and the resulting precipitate was collected by filtration and washed with ether. The solid was dissolved in water and the solution was neutralized by the addition of concentrated aqueous ammonium hydroxide. The aqueous layer was extracted with chloroform, the organic layer was washed with brine and the solvent was removed in vacuo. The residue was dissolved in ethyl acetate, treated with charcoal and passed through a plug of silica. Removal of the solvent in vacuo afforded 3.1 g (60%) of 6-carboethoxy imidazo[1,2-a]-pyridine as an off-white solid, m.p. 93°–94° C. when recrystallized from tert-butylmethyl ether and dried for 16 hours at 50° C. in high vacuum.

(c)

1-Cyclopentyl-3-ethyl-6-(6-imidazo[1,2-a]pyridinyl) pyrazolo[3,4-d]pyrimidin-4-one Sodium metal (0.21 g, 9.2 mmol) was dissolved in ethanol (25 ml) and 6-carboethoxyimidazo[1,2-a]pyridine (1.75 g, 9.2 mmol) and 1-cyclopentyl-3-ethyl-5-amino-1H-pyrazole-4-carboxamide (1.02 g, 4.6 mmol) were added. The reaction mixture was heated to reflux for 24 hours, cooled to room temperature and stirred for 60 hours. The solvent was removed in vacuo, the residue was dissolved in water (100 ml) and the solution was neutralized by the addition of concentrated HCl. A precipitate was obtained which was collected by filtration through a glass frit. The solid was recrystallized from ethanol and washed with ether to afford 0.98 g (62%) of 1-cyclopentyl-3-ethyl-6-(6-imidazo[1,2-a]-pyridinyl)-pyrazolo[3,4-d]pyrimidin-4-one as white crystals, m.p. >300° C. when dried for 18 hours at 120° C. in high vacuum.

EXAMPLE 17

(a)

2-(Hydroxycyclopentyl) hydrazine

Cyclopentene oxide (50.0 g, 0.6 mol) and hydrazine hydrate (5.0 g, 0.1 mol) were combined and heated to reflux for 72 hours. The reaction mixture was cooled to room temperature and excess cyclopentene oxide was removed in vacuo to afford 11.6 g (100%) of 2-(hydroxycyclopentyl)hydrazine as a colorless, viscous oil.

(b)

1-(2-Hydroxycyclopentyl)-3-methyl-4-cyano-5-amino-1H-pyrazole

To a stirred solution of 2-(hydroxycyclopentyl)hydrazine (11.6 g, 0.1 mol) in ethanol (75 ml) was added ethoxyethylidene malononitrile (13.6 g, 0.1 mol). The reaction mixture was heated to reflux for 32 hours, cooled to room temperature and the solvent was removed in vacuo. The residue was dissolved in boiling isopropanol (100 ml), treated with charcoal and the filtrate was concentrated to approximately 40 ml. The solution was diluted with ether (20 ml), allowed to stand for 1 hour at room temperature and the resulting precipitate was collected by filtration to afford 8.7 g (42%) of 1-(2-hydroxycyclopentyl)-3-methyl-5-amino-1H-pyrazole-4-carbonitrile as light orange crystals, m.p. 157°–159° C. when dried at 75° C. in high vacuum.

(c)

1-(2-Hydroxycyclopentyl)-3-methyl-5-amino-1H-pyrazole-4-carboxamide

To a solution of sodium hydroxide (1.2 g, 30 mmol) in water (50 ml) in an ice-bath was added 30% hydrogen peroxide (3.3 ml, 29 mmol). The reaction mixture was stirred for 5 minutes then 1-(2-hydroxycyclopentyl)-3-methyl-5-amino-1H-pyrazole-4-carbonitrile (2.5 g, 12 mmol) was added. The reaction mixture was stirred in an ice-bath for 5 hours, additional 30% hydrogen peroxide (1.5 ml) was added and stirring was continued for 2 hours. Acetic acid (2 ml) was added to the reaction mixture, all but approximately 25 ml of the solvent was removed in vacuo and the resulting solid was collected by filtration and washed with water. The solid was air dried to afford 2.4 g (90%) of 1-(2-hydroxycyclopentyl)-3-methyl-5-amino-1H-pyrazole-4-carboxamide as a white solid, m.p. 120°–124° C. (dec.).

(d)

4-Pyridinecarboxamidine hydrochloride

A solution of 4-pyridinecarbonitrile (370 g, 3.55 mol) and sodium methoxide (20.0 g, 0.37 mol) in methanol (1.7 l) was stirred at room temperature for 1.5 hours, then ammonium chloride (200 g, 3.7 mol) was added. The reaction mixture was stirred for 24 hours, the resulting solid was collected by filtration and the filtrate was evaporated to dryness. The two crops were combined and recrystallized from water to afford 394 g (70%) of 4-pyridinecarboxamidine hydrochloride, m.p. 250°–252° C. (dec.).

(e)

1-(2-Hydroxycyclopentyl)-3-methyl-6-(4-pyridyl)pyrazolo[[3,4-d]pyrimidin-4-one

A mixture of 1-(2-hydroxycyclopentyl)-3-methyl-1H-pyrazolo-4-carboxamide (2.4 g, 10 mmol), 4-pyridinecarboxamidine hydrochloride (3.2 g, 20 mmol), potassium carbonate (2.8 g, 20 mmol) and DMF (50 ml) were heated under reflux for 28 hours. The solvent was removed in vacuo, the residue was dissolved in hot water (25 ml) and was filtered. The filtrate was acidified with acetic acid and the resulting white precipitate was collected by filtration and recrystallized from DMF to afford 0.73 g (21%) of 1-(2-hydroxycyclopentyl)-3-methyl-6-(4-pyridyl)-pyrazolo [3,4-d]-pyrimidin-4-one as white needles, m.p. 281°–283° C.

EXAMPLE 18

(a)

1-(3-Tetrahydrothienyl 1,1-dioxide)-3-methyl-5-amino-1H-pyrazole-4-carbonitrile

To a mixture of 3-sulfolanylhydrazine hydrochloride (18.6 g, 0.1 mol) and ethoxyethylidene malononitrile (14.4 g, 0.11 mol) in ethanol (250 ml) was added triethylamine (13.9 ml, 0.1 mol). The reaction mixture was heated to reflux under argon for 2 hours. The solvent was removed in vacuo and the residue was recrystallized from water after treatment with charcoal to afford 16.4 g (68% of 1-(3-tetrahydrothienyl-1,1-dioxide)-3-methyl-5-amino-1H-pyrazole-4-carbonitrile as an off-white solid.

(b)

1-(3-Tetrahydrothienyl-1,1-dioxide)-3-methyl-5-amino-1H-pyrazole-4-carboxamide

A mixture of potassium hydroxide (2.3 g, 41.6 mmol) in water (50 ml) was stirred in an ice-bath for 10 minutes, then 30% hydrogen peroxide (2.6 ml, 84.7 mmol) and 1-(3-tetrahydrothienyl-1,1-dioxide)-3-methyl-5-amino-1H-pyrazole-4-carbonitrile (1.2 g, 5.1 mmol) were added sequentially. The reaction mixture was slowly warmed to room temperature and was stirred for 4 hours. Additional 30% hydrogen peroxide (0.5 ml) was added and the reaction mixture was stirred at room temperature for 24 hours. The product was collected by filtration through a glass frit and washed with water, then ether to afford 0.88 g (68%) of 1-(3-tetrahydrothienyl-1,1-dioxide )-3-methyl-5-amino-1H-pyrazole-4-carboxamide as white crystals, m.p. 243°–244° C. when recrystallized from methanol and dried for 18 hours at 85° C. in high vacuum.

(c)

1-(3-Tetrahydrothienyl-1,1-dioxide)-3-methyl-6-(4-pyridyl)pyrazolo[3,4-d]pyrimidin-4-one methanesulfonate 1-(3-Tetrahydrothienyl-1,1-dioxide)-3-methyl-5-amino-1H-pyrazole-4-carboxamide (3.6 g, 14.1 mmol) and isonicotinyl chloride hydrochloride (3.8 g, 21.2 mmol) were combined and heated to 255° C. for 10 minutes under argon. The reaction mixture was cooled to room temperature, chloroform (20 ml) and saturated NaHCO$_3$ were added and the solid was collected by filtration. The solid was digested in ethanol/ethyl acetate to afford, after filtration through a glass frit, 0.92 g (19%) of the free-base of the desired product as a creamy white solid which was recrystallized from DMF. This solid was then treated with concentrated methanesulfonic acid, diluted with methanol, filtered and chilled on ice. The resulting precipitate was collected by filtration through a glass frit and washed with methanol then ether to afford 0.46 g of 1-(3-tetrahydrothienyl-1,1-dioxide)-3-methyl-6-(4-pyridyl)-pyrazolo[3,4-d]pyrimidin-4-one methanesulfonate as pale yellow crystals, m.p. 293°–29° C. when dried at 120° C. for 18 hours in high vacuum.

EXAMPLE 19

(a)

3,3-(Bis-methylthio)-2-cyanoacrylic acid methyl ester

Methylcyanoacetate (100 g, 1.01 mol) was added to a solution of sodium methoxide (95 g, 1.8 mol) in methanol (1.3 l) under nitrogen. The solution was cooled to 5°–10° C., stirred for 15 minutes then carbon disulfide (60.3 ml, 1.01 mol) was added dropwise. The reaction mixture was stirred for 20 minutes then dimethylsulfate (191 ml, 2.0 mol) was added dropwise while maintaining the temperature at 5°–10° C. The reaction mixture was warmed to room temperature and was stirred for 60 hours. The reaction mixture was poured into ice-water (5 l) with vigorous stirring and the obtained precipitate was collected by filtration and washed with water to afford 62.1 g (30%) of 3,3-(bismethylthio)-2-cyanoacrylic acid methyl ester, m.p. 82°–83° C. when dried at 25° C. in high vacuum.

(b)

Methyl 1-cyclopentyl-3-methylthio-5-amino-1H-pyrazole-4-carboxylate

To a mixture of cyclopentyl hydrazine hydrochloride (7.0 g, 0.05 mol) in methanol (60 ml) was added sodium methoxide (2.8 g, 0.05 mol). The reaction mixture was stirred at room temperature for 15 minutes, the solution was filtered and the filtrate was added to a solution of 3,3-(bis-methylthio)-2-cyanoacrylic acid methyl ester (10.5 g, 0.05 mol) in methanol (40 ml). The reaction mixture was heated to reflux for 5 hours, then stirred at room temperature for 24 hours. The reaction mixture was filtered, the solvent was removed in vacuo and the residue was purified by column chromatography on silica eluting with ethyl acetate/hexanes (25/75), followed by recrystallization from ether/hexanes to afford 5.2 g (39%) of methyl 1-cyclopentyl-3-methylthio-5-amino-1H-pyrazole-4-carboxylate, m.p. 88°–89° C. when dried at 50° C. for 5 hours in high vacuum.

(c)

1-Cyclopentyl-3-methylthio-6-(4-pyridyl)pyrazolo[3,4-d]pyrimidin-4-one

A mixture of methyl 1-cyclopentyl-3-methylthio-5-amino-1H-pyrazole-4-carboxylate (3.0 g, 0.012 mol), 4-pyridine carboxamidine hydrochloride (1.9 g, 0.012 mol), potassium carbonate (1.6 g, 0.012 mol) and DMF (25 ml) were refluxed for 4 hours. Additional 4-pyridinecarboxamidine hydrochloride (1.9 g) and potassium carbonate (1.6 g) were added and the reaction mixture was refluxed for 24 hours. The solution was poured into ice-water, neutralized with acetic acid and the resulting precipitate was collected by filtration and washed with water. Recrystallization of the solid from DMF afforded 0.48 g (12%) of 1-cyclopentyl-3-methylthio-6-(4-pyridyl )-pyrazolo [3,4-d]-pyrimidin-4-one as a white powder, m.p. 272°–274° C. when dried at 110° C. for 16 hours in high vacuum.

EXAMPLE 20

(a)

2-Methylthio-2-dimethylamino-1-cyanoacrylic acid methyl ester

A mixture of sodium methoxide (5.4 g, 0.1 mol) in methanol (40 ml) was treated with dimethylamine hydrochloride (8.2 g, 0.1 mol) and 3,3-(bis-methylthio)-2-cyanoacrylic acid methyl ester (10.2 g, 0.05 mol). The reaction mixture was refluxed for 15 minutes, then stirred at room temperature for 3 hours. The solution was filtered to remove salts and the filtrate was concentrated in vacuo. The residue was recrystallized from methanol to afford 8.2 g (82%) of 2-methylthio-2-dimethylamino-1-cyanoacrylic acid methyl ester, m.p. 94°–96 ° C.

Following the procedure of Example 19, parts b and c, but substituting 2-methylthio-2-dimethylamino-1-cyanoacrylic acid methyl ester for 3,3-(bis-methylthio)-2-cyanoacrylic acid methyl ester in part b, and substituting methyl 1-cyclopentyl-3-dimethylamino-5-amino-1H-pyrazole-4-carboxylate for methyl 1-cyclopentyl-3-methylthio-5-amino-1H-pyrazole-4-carboxylate in part c, there was obtained:

(b)

Methyl 1-cyclopentyl-3-dimethylamino-5-amino-1H-pyrazole-4-carboxylate, 25%, m.p. 94°–97° C. when purified by column chromatography eluting with ethyl acetate/hexanes (20/80).

(c)

1-Cyclopentyl-3-dimethylamino-6-(4-pyridyl) pyrazolo[3,4-d]pyrimidin-4-one, 54%, yellow solid, m.p. 278°–280° C. when recrystallized from DMF and dried at 110° C. for 20 hours in high vacuum.

EXAMPLE 21

(a)

1-Hydroxy-tert-butylmethylidene malononitrile

To a mixture of malononitrile (33 g, 0.5 mole), triethylamine (101.2 g, 1.0 mole) and THF (600 ml) at 0° C. under argon was added dropwise trimethylacetyl chloride (60.3 g, 0.5 mole) in THF (50 ml) over 30 minutes. The reaction mixture was stirred at 0° C. for 1 hour, triethylamine hydrochloride was removed by filtration and was washed with THF. The filtrate was poured into ice-water (1000 ml), treated with concentrated sulfuric acid (33 ml) in water (160 ml) until obtained pH=3 and was extracted with chloroform (4×250 ml). The organic layers were combined, dried over anhydrous $MgSO_4$ and concentrated in vacuo. The residue was titurated with ether and filtered cold to afford 16 g (21%) of 1-hydroxy-tert-butyl-methylidene malononitrile as cream colored flakes, m.p. 153°–154° C. when dried at 50° C. for 24 hours in high vacuum. Concentration of the filtrate afforded an additional 26.5 g (34%) of the product for a total yield of 56%.

(b)

1-Methoxy-tert-butylmethylidene malononitrile

To a mixture of 1-hydroxy-tert-butylmethylidene malononitrile (42.5 g, 0.28 mol), water (75 ml) and p-dioxane (453 ml) was added dimethyl sulfate (249.6 g, 2.0 mol) followed by the slow addition of sodium bicarbonate. The pink reaction mixture was heated on a steam bath for 2 hours, cooled to room temperature and poured into water (2 l). The mixture was extracted with ether (5×500 ml) and the organic layer was concentrated in vacuo. The residue was azeotroped with toluene, then ethanol and was finally treated with ether and a small amount of isopropanol. The obtained oil was combined with 5% $K_2CO_3$ (200 ml) and the dark oil (more dense layer) was separated. The aqueous layer was extracted with chloroform (3×100 ml) and the combined organic layers were dried over anhydrous $MgSO_4$ and the solvent was removed in vacuo to afford 16.9 g (36%) of 1-methoxy-tertbutylmethylidene malononitrile as a brown oil.

(c)

1-Cyclopentyl-3-tert-butyl-5-amino-1H-pyrazole-4-carbonitrile hydrochloride

A mixture of cyclopentylhydrazine hydrochloride (6.7 g, 0.049 mol), xylenes (125 ml) and sodium methoxide (3.2 g, 0.06 mol) under argon was stirred for 30 minutes, then 1-methoxytertbutylmethylidene malononitrile (8.0 g, 0.049 mol) was added. The reaction mixture was refluxed for 5 days, cooled to room temperature and the solvent was removed in vacuo. The residue was extracted with chloroform and washed with water. The aqueous layer was extracted with chloroform (2×200 ml) and the combined organic layers were dried over $MgSO_4$ and concentrated in vacuo. The residue was purified by column chromatography on silica eluting with hexanes/ether (70/30) to ether. The product was dissolved in ether (10 ml) and treated with ethereal.HCl to afford, after collection of the product by filtration, 2.9 g (22%) of 1-cyclopentyl-3-tert-butyl-5-amino-1H-pyrazole-4-carbonitrile hydrochloride, m.p. 134° C. (dec.).

EXAMPLE 22

(a)

1-Chloro-trifluoromethylmethylidene malononitrile

To a solution of sodium methoxide in methanol, prepared from sodium metal (3.8 g) and methanol (100 ml), was added malononitrile (11.0 g, 0.17 mol) followed by methyl trifluoroacetate (43 g, 0.21 mol). The reaction mixture was heated to reflux for 4 hours and the solvent was removed in vacuo. The residue was dissolved in dichloromethane (100 ml) and phosphorous pentachloride (32.5 g, 0.16 mol) was added. The reaction mixture was heated to reflux for 4 hours, cooled to room temperature and filtered. The filtrate was distilled under house vacuum to afford 19.4 g (64%) of 1-chloro-trifluoromethylmethylidene malononitrile, B.P. 50°–62° C., $n^{25}d$ 1.4180.

(b)

1-Ethoxy-trifluoromethylmethylidene malononitrile

1-Chloro-trifluoromethylmethylidene malononitrile (12.0 g, 0.067 mol) in ethanol (60 ml) was stirred for 30 minutes. The ethanol was removed at 40° C. in vacuo, more ethanol was added and this was removed at 40° C. in vacuo to afford 1-ethoxytrifluoromethylmethylidene malononitrile which was used directly in subsequent reactions without characterization.

(c)

1-Cyclopentyl-3-trifluoromethyl-5-amino-1H-pyrazole-4-carbonitrile

A mixture of cyclopentylhydrazine hydrochloride (9.1 g, 0.067 mol), ethanol (60 ml) and sodium methoxide (3.6 g, 0.067 mol) was stirred at room temperature for 15 minutes. The inorganic salts were removed by filtration and the filtrate was added to 1-ethoxy-trifluoromethylmethylidene malononitrile (12.7 g, 0.067 mol) in ethanol (10 ml). The reaction mixture was refluxed for 1 hour cooled to room temperature and the solvent was removed in vacuo. The residue was taken up in ethyl acetate, washed with water, dried over $MgSO_4$ and concentrated in vacuo. The residue was purified by column chromatography on silica eluting with hexanes/ethyl acetate (70/30) to afford 9.9 g (61%) of 1-cyclopentyl-3-trifluoromethyl-5-amino-1H-Pyrazole-4-carbonitrile as a yellow solid.

EXAMPLE 23

(a)

1-Hydroxy-2-phenylethylidene malononitrile

To a suspension of 97% NaH (24.7 g, 1.0 mol) in THF (760 ml) under nitrogen was added dropwise malononitrile (33.4 g, 0.5 mol) in THF (150 ml) over 70 minutes. The reaction mixture was stirred at room temperature for 1 hour, then phenylacetyl chloride (78.9 g, 0.5 mol) in THF (80 ml) was added dropwise over 1.5 hours. The reaction mixture was stirred at room temperature for 24 hours and the solvent was removed in vacuo. The residue was cooled and taken up in 2N aqueous $H_2SO_4$ (1060 ml). The two-phase mixture was extracted with ether (3×700 ml), the organic layers were combined, washed with water (2×1000 ml) and dried over $MgSO_4$. The solvent was removed in vacuo to afford 96.4 g (95%) of 1-hydroxy-2-phenylethylidene malononitrile as a dark amber liquid.

(b)

1-Methoxy-2-phenylethylidene malononitrile

To a suspension of 97% NaH (11.5 g, 0.47 mol) in THF (250 ml) under nitrogen was added 1-hydroxyphenylethylidene malononitrile (94.0 g, 0.47 mol) in THF (500 l) dropwise over 75 minutes. The reaction mixture was stirred at room temperature for 15 minutes then dimethylsulfate (58.7 g, 0.47 mol) in THF (280 ml) was added dropwise over 35 minutes. The reaction mixture was then refluxed on a steam bath for 3.5 hours, cooled to room temperature and stirred for 24 hours. The solvent was removed in vacuo and the residue was dissolved in ether (900 ml)/water (750 ml). The organic layer was separated, washed with saturated $NaHCO_3$ (2×400 ml), dried over $MgSO_4$ and concentrated in vacuo to afford 79.9 g (87%) of 1-methoxy-2-phenylethylidene malononitrile as a brown viscous residue.

(c)

1-tert-Butyl-3-phenylmethyl-5-amino-1H-pyrazole-4-carbonitrile

To a suspension of potassium carbonate (48.8 g, 0.35 mol) in ethanol (350 ml) under nitrogen was added tert-butyl hydrazine hydrochloride. The reaction mixture was stirred at room temperature for 5 minutes, then 1-methoxyphenylethylidene malononitrile (70.0 g, 0.35 mol) was added in one portion. The reaction mixture was heated to reflux on a steam bath for 4.5 hours, cooled to room temperature and allowed to stand for 24 hours. The inorganic salts were removed by filtration and washed with ethanol. The filtrate was concentrated in vacuo, triturated with ether (350 ml) and filtered. The filtrate was concentrated in vacuo and the residue was purified by column chromatography on silica eluting with ethyl acetate/hexanes/chloroform (35/60/5). The product was triturated with pentane and collected by filtration to afford 18.2 g (20%) of 1-tert-butyl-3-phenylmethyl-5-amino-1H-pyrazole-4-carbonitrile as white crystals, m.p. 106°–110° C. when dried at 55° C. in high vacuum.

(d)

1-tert-Butyl-3-phenylmethyl-6-(4-pyridyl)pyrazolo[3,4-d]pyrimidin-4-amine

To a suspension of 4-pyridinecarboxamidine hydrochloride (12.5 g, 0.10 mol) in Dowtherm (125 ml) was added 1-tert-butyl-3-phenylmethyl-5-amino-1H-pyrazole-4-carbonitrile (13.1 g, 0.052 mol). The reaction mixture was heated to 225° C., stirred for 1 hour, cooled to room temperature and allowed to stand for 24 hours. The reaction mixture was diluted with pentane (800 ml) to afford a pale yellow solid which was collected by filtration. The solid was recrystallized from ethanol to afford 9.8 g of product. The filtrate was concentrated, triturated with ether and an additional 1.6 g of product was collected by filtration. A total of 11.4 g (62%) of 1-tert-butyl-3-phenylmethyl-6-(4-pyridyl)-pyrazolo[3,4-d]pyrimidin-4-amine was obtained as an off-white solid, m.p. 188°–189° C. when dried in high vacuum.

EXAMPLE 24

(a)

tert-Butyl cyclobutylidinecarbazate

Cyclobutanone (20.0 g, 0.29 mol), tert-butyl carbazate (37.7 g, 0.29 mol) and hexanes (300 ml) were combined and heated on a steam bath for 1 hour. The solvent was removed in vacuo, the residue was slurried with isopropanol and diluted with ether. The mixture was cooled and the obtained solid was collected by filtration. The mother liquor was concentrated, treated with hexanes and the resulting solid was collected by filtration. The two solids were combined to afford 43.1 g (82%) of tert-butylcyclobutyl-idinecarbazate, m.p. 108°–109° C. when dried in high vacuum.

(b)

Cyclobutylhydrazine hydrochloride

To a mixture of tert-butyl cyclobutylidinecarbazate (37.3 g, 0.20 mol), methanol (240 ml) and THF (180 ml) was added sodium cyanoborohydride (15.3 g, 0.24 mol). The reaction mixture was heated on a steam bath until reflux then was cooled to room temperature and stirred for 20 minutes. 6N HCl (85 ml) was added dropwise over 10 minutes, then the mixture was refluxed on a steam bath for 20 minutes. The mixture was cooled, the salts were removed by filtration and the filtrate was concentrated in vacuo. The residue was slurried with isopropanol, chilled, diluted with ethereal-HCl and filtered. The solid was rinsed with ether and dried in high vacuum to afford 23.8 g (96%) of cyclobutylhydrazine hydrochloride as a white solid, m.p. 128°–130° C.

Following the procedure of Example 24, part a, but slurrying the residue with ether/hexanes (1/40) rather than isopropanol/ether there was obtained:

EXAMPLE 25

(a)

tert-Butyl-norbornylidinecarbazate, 57%, m.p. 139°–140° C. when air dried for 24 hours.

(b)

Norbornylhydrazine hydrochloride

To a solution of tert-butylnorbornylidinecarbazate (17.0 g, 0.076 mol), methanol (115 ml), THF (85 ml) and bromocresol green (3 crystals) under argon was added sodium cyanoborohydride (5.3 g, 0.084 mol). The blue solution was stirred for 1 hour then 6N HCl (60 ml) was added dropwise until the reaction mixture turned yellow. The reaction mixture was refluxed for 1.25 hours, cooled and the salts were removed by filtration. The filtrate was concentrated in vacuo, azeotroped with isopropanol and the residue was treated with isopropanol. Cooling the mixture afforded a solid which was collected by filtration and washed with ether to afford 9.5 g (77%) of norbornylhydrazine hydrochloride as a white solid, m.p. 124°–126° C. when dried at 40° C. in high vacuum.

EXAMPLE 26

(a)

Methyl 3-oxo-tetrahydrofuranyl-4-carboxylate

To a cooled mixture of methyl glycolate (9.0 g, 0.1 mol) in DMSO (100 ml) was added sodium methoxide (5.4 g, 0.1 mol). The reaction mixture was stirred for 0.5 hours, then methyl acrylate (8.6 g, 0.1 mol) was added in one portion. The reaction mixture was stirred in an ice-bath for 15 minutes, at room temperature for 4 hours and finally allowed to stand at room temperature for 60 hours. The reaction mixture was poured into 20% $H_2SO_4$ (600 ml) and extracted with ether (3×250 ml). The combined organic layers were washed with brine, dried over $MgSO_4$ and concentrated in vacuo. The yellow oil was fractionally distilled to afford 5.0 g (34%) of methyl tetrahydrofuranyl-3-oxo-4-carboxylate, B.P. 51°–52° C. at 0.15 mm Hg.

(b)

Tetrahydrofuran-3-one

A solution of methyl 3-oxo-tetrahydrofuranyl-4-carboxylate (14.5 g, 0.1 mol) in 10% $H_2SO_4$ (50 ml) was refluxed for 1 hour. The reaction mixture was cooled and extracted with ether (3×100 ml). The organic layers were combined, dried over $MgSO_4$ and concentrated in vacuo. The pale gold residue was distilled to afford 6.8 g (79%) of tetrahydrofuran-3-one, B.P. 74°–75° C. at 100 mm Hg.

(c)

tert-Butyltetrahydrofuranylidinecarbazate

A mixture of tetrahydrofuran-3-one (4.65 g, 54.0 mmol), tert-butyl carbazate (7.1 g, 54.0 mmol) and hexanes (100 ml) was heated on a steam bath for 0.5 hour. The reaction mixture was cooled in an ice-bath and the product was collected by filtration to afford 9.6 g (89%) of tert-butyl tetrahydrofuranylidinecarbazate as white needles, m.p. 82°–83° C. when dried in high vacuum.

(d)

3-Tetrahydrofuranylhydrazine hydrochloride

To a mixture of tert-butyl tetrahydrofuranylidinecarbazate (9.0 g, 45.0 mmol), methanol (60 ml), THF (45 ml) and bromocresol green (3 crystals) was added sodium cyanoborohydride (3.4 g, 54.0 mmol). The reaction mixture was stirred at room temperature for 30 minutes, then 6N HCl (30 ml) was added to afford a yellow solution. The mixture was heated on a steam bath for 30 minutes, inorganic salts were removed by filtration and the filtrate was concentrated in vacuo. The oily residue was digested in isopropanol (100 ml), insoluble material was filtered and the filtrate was diluted with ether. The mixture was cooled for 60 hours, filtered and the filtrate was concentrated in vacuo to afford a viscous yellow oil which was used directly in subsequent transformations without further purification.

(e)

1-(3-Tetrahydrofuranyl)-3-methyl-5-amino-1H-pyrazole-4-carbonitrile

A mixture of 3-tetrahydrofuranylhydrazine hydrochloride (6.2 g, 0.045 mol), sodium methoxide (2.4 g, 0.045 mol) and ethanol (70 ml) was refluxed under argon for 10 minutes. The reaction mixture was cooled to room temperature and 1-ethoxyethylidene malononitrile (6.1 g, 0.045 mol) was added. The reaction mixture was heated to reflux and stirred for 21 hours. The reaction was cooled and the solvent was removed in vacuo. The residue was recrystallized from water to afford 4.7 g (54%) of 1-(3-tetrahydrofuranyl)-3-methyl-5-amino-1H-pyrazole-4-carbonitrile as yellow crystals, m.p. 134°–135° C. when dried at 90° C. in high vacuum.

EXAMPLE 27

2-Pyridinecarboxamidine hydrochloride

To a solution of 2-cyanopyridine (20.0 g, 0.19 mol) in methanol (300 ml) under argon was added sodium methoxide (0.5 g). The reaction mixture was stirred at room temperature for 24 hours, then ammonium chloride (10.7 g, 0.2 mol) was added. The mixture was stirred at room temperature for 3,5 hours and the solvent was removed in vacuo. The residue was diluted with isopropanol (20 ml) and ether (400 ml) and a solid was collected by filtration to afford 28.2 g (87%) of 2-pyridinecarboxamidine hydrochloride as a white solid, m.p. 141°–142° C. when dried at 40° C. in high vacuum.

EXAMPLE 28

3-Pyridinecarboxamidine hydrochloride

To a solution of 3-cyanopyridine (208 g, 2.0 mol) in methanol (100 ml) in an ice-bath was added sodium methoxide (11.2 g, 0.2 mol). The reaction mixture was stirred until all of the sodium methoxide had dissolved and was subsequently stoppered and placed in the refrigerator for 96 hours. Ammonium chloride (118 g, 2.2 mol) was then added and the reaction mixture was stirred in an ice-bath for 8 hours, followed by room temperature for 24 hours. The reaction mixture was filtered and the filtrate was concentrated in vacuo. The residue was taken up in boiling ethanol (2 l), the solution was filtered and cooled to cause precipitation. The solid was collected by filtration and recrystallized in boiling n-propanol (1.4 l) to afford 153 g of a white solid. The filtrates were combined, concentrated in vacuo and the residue was recrystallized from n-propanol to afford 17.5 g of a white solid. The filtrate was once again concentrated in vacuo and the residue was recrystallized from n-propanol (500 ml) to afford 73 g of a white solid. The three crops were combined to afford 243.5 g (78%) of 3-pyridinecarboxamidine hydrochloride, m.p. 185°–190° C. when dried at 60° C. in high vacuum.

EXAMPLE 29

(a)

3-cyano-4-cyano-5-amino-1H-pyrazole-1-carboxamide

To a mixture of semicarbazide hydrochloride (11.2 g, 0.1 mol), water (200 ml) and sodium hydroxide (4.0 g, 0.1 mol) cooled in an ice-bath was added dropwise tetracyanoethylene (12.8 g, 0.1 mol). The reaction mixture was warmed to room temperature, stirred for 1.5 hours and then allowed to stand for 24 hours. The white precipitate which formed during the course of the reaction was collected by filtration and washed with water to afford 15.6 g (89%) of 3-cyano-4-cyano-5-amino-1H-pyrazole-1carboxamide as a white solid, m.p. 225° C. (dec.) when dried at 85° C. in high vacuum.

(b)

3-cyano-5-amino-1H-pyrazole-4-carbonitrile 3-cyano-4-cyano-5-amino-1H-pyrazole-1-carboxamide (15.6 g, 0.089 mol) was added in small protions to boiling water (150 ml). Upon completion of the addition, the reaction mixture was stirred at reflux for 5 minutes, cooled and a solid was collected by filtration. The solid was washed with water and air dried to afford 10.4 g (88%) of 3-cyano-5-amino-1H-pyrazole-4-carbonitrile, m.p. 260° C. (dec.).

General Method A

To a slurry of the appropriate malononitrile in 250–700 ml of ethanol per mole of the malononitrile at room temperature was added dropwise one to two equivalents of hydrazine monohydrate while maintaining the temperature at approximately 25° C. The reaction mixture was stirred at room temperature for 24 hours, cooled in an ice-bath and the resulting solid was collected by filtration, washed with ether and dried in high vacuum. The results are summarized in Table A.

General Method B

To a solution of one equivalent of the appropriate hydrazine hydrochloride in 1–2.5 l of ethanol per mole of the malononitrile was added 1–1.2 equivalents of sodium methoxide per mole of the malononitrile. The reaction mixture was stirred at room temperature for 15–30 minutes then the appropriate malononitrile was added. The reaction mixture was heated to reflux and stirred for 1–36 hours. The inorganic salts were removed by filtration and the filtrate was concentrated in vacuo. The residue was purified by column chromatography on silica. The results are summarized in Table A.

$$\underset{NC}{\overset{R^3}{\underset{CN}{\bigg|\bigg|}}}\overset{OEt}{} \; + \; \begin{array}{c} R^1NHNH_2.HCl \\ \text{or} \\ R^1NHNH_2.H_2O \end{array} \longrightarrow \underset{H_2N}{\overset{NC}{\underset{N}{\bigg|\bigg|}}}\overset{R^3}{\underset{\underset{R^1}{|}}{N}}$$

| Example No. | $R^1$ | $R^3$ | Method | Yield % | Melting Range °C. | Chromatography Solvent | Recrystallized From |
|---|---|---|---|---|---|---|---|
| 30 | H | Me | A | 56 | 161–163 | — | Et$_2$O/EtOH |
| 31 | H | Et | A | 84 | — | — | — |
| 32 | H | H | A | 82 | 168–170 | — | EtOH |
| 33 | cyclobutyl | Me | B | 42 | 134–135 | Et$_2$O/cyclohexane 35/65 → 50/50 | — |
| 34 | norbornyl | Me | B | 60 | 168–169 | hexanes → Et$_2$O/ hexanes → Et$_2$O 100 → 60/40 → 100 | — |

EXAMPLE 35

1-tert-Butyl-3-methyl-5-amino-1H-pyrazole-4-carbonitrile

To a slurry of 1-ethoxyethylidene malononitrile (68.0 g, 0.5 mol), tert-butylhydrazine hydrochloride (62.3 g, 0.5 mol) in ethanol (500 ml) was added triethylamine (70 ml, 0.5 mol). The reaction mixture was stirred at room temperature for 2 hours, cooled in an ice-bath and a solid was collected by filtration and was washed with ether. The mother liquor was concentrated and the solid residue was recrystallized from ethanol. The two solid fractions were combined and dried at 65° C. in high vacuum for 24 hours to afford 132 g of 1-tert-butyl-3-methyl-5-amino-1H-pyrazole-4-carbonitrile as a white solid which is contaminated with triethylamine hydrochloride (approximately ⅔mol).

EXAMPLE 36

(a)

1-tert-Butyl-3-ethyl-5-amino-1H-pyrazole-4-carbonitrile

A mixture of 1-ethoxyethylidene malononitrile (60.0 g, 0.4 mol), tert-butylhydrazine hydrochloride (50.0 g, 0.4 mol) and ethanol (500 ml) was heated to reflux. The heat was removed and triethylamine (55.8 ml, 0.4 mol) was added dropwise at such a rate as to maintain a gentle reflux. The reaction mixture was refluxed for an additional 1 hour, cooled to room temperature and the solvent was removed in vacuo. The residue was taken up in ethyl acetate (300 ml) and washed with water (200 ml). The organic layer was separated, washed with brine and dried over sodium sulfate. The solvent was removed in vacuo to afford 75.6 g (67%) of 1-tert-butyl-3-ethyl-5-amino-1H-pyrazole-4-carbonitrile.

Following a procedure substantially similar to that described in Example 5, part d, but substituting the product of Example 36a for 1-tert-butyl-3-(cyclohexylmethyl)-5-amino-1H-pyrazole-4-carbonitrile there was obtained:

(b)

1-tert-Butyl-3-ethyl-5-amino-1H-pyrazole-4-carboxamide as a yellow solid in a 68% yield, m.p. 148°–150° C.

EXAMPLE 37

(a)

1-tert-Butyl-5-amino-1H-pyrazole-4-carbonitrile

To a mixture of tert-butylhydrazine (40 g, 0.32 mol), sodium methoxide (18 g, 0.32 mol) and ethanol 150 ml) was added ethoxymethylene malononitrile (42 g, 0.32 mol). The reaction mixture was heated to reflux for 2 hours and the solvent was removed in vacuo. The residue was extracted with chloroform, washed with water and the organic layer was concentrated in vacuo to afford 46 g (87%) of 1-tert-butyl-5-amino-1H-pyrazole-4-carbonitrile as a semi-solid.

(b)

1-tert-Butyl-6-(4-pyridyl)-pyrazolo[3,4-d] pyrimidin-4-amine

A mixture of 4-cyanopyridine (25.0 g, 0.24 mol) sodium methoxide (0.5 g, 0.009 mol) and methanol (150 ml) was stirred at room temperature for 4 hours. The solvent was removed in vacuo and 1-tert-butyl-5-amino-1H-pyrazole-4-carbonitrile (45.0 g, 0.27 mol) was added. The reaction mixture was heated at 130°–150° C. for 3 hours and cooled to room temperature. The residue was dissolved in ethanol, chilled, and the resulting precipitate was collected by filtration and dried in high vacuum to afford 12 g of product. The mother liquor was concentrated to afford 26 g of additional product. Total of 38 g (59%) of 1-tert-butyl-6-(4pyridyl)-pyrazolo[3,4-d]pyrimindin-4-amine as pale crystals, m.p. 250°–252 ° C.

EXAMPLE 37-AB (a)

1,3-dimethyl-5-amino-1H-pyrazole-4-carbonitrile

To a solution of 1-ethoxyethylidene malononitrile (27.2 g, 0.2 mol) in ethanol (50 ml) was added methyl hydrazine (9.4 g, 0.2 mol). The reaction mixture was stirred at room temperature for 3 hours and the product was collected by filtration to afford 23.6 g (87%) of 1,3-dimethyl-5-amino-1H-pyrazole-4-carbonitrile as white crystals, m.p. 193°–195° C. when dried in high vacuum.

(b)

1,3-dimethyl-6-(4-pyridyl)-pyrazolo-[3,4-d] pyrimidin-4-amine

A solution of 4-cyanopyridine (16.0 g, 0.15 mol), sodium methoxide (0.5 g, 0.009 mol) and methanol (150 ml) were stirred at room temperature for 4 hours, then the solvent was removed in vacuo. 1,3-dimethyl-5-amino-1H-pyrazole-4-carbonitrile (22.0 g, 0.16 mol) was added to the residue and the mixture was heated to 130°–140° C. for 30 minutes. The reaction mixture was cooled and the resdue recrystallized from ethanol to afford 25.4 g (71%) of 1,3-dimethyl-6-(4-pyridyl)-pyrazolo[3,4-d]pyrimidin-4-amine as a tan powder, m.p. 235°–236° C.

General Method C

A mixture of the appropriate 1H-pyrazole, 1–1.5 equivalents of the appropriate amidine hydrochloride, 1–2 equivalents of potassium carbonate and 300–2000 ml of DMF per mole of pyrazole were refluxed under argon for 2–24 hours. The reaction mixture was cooled to room temperature and poured into 500–5000 ml of water. A solid was formed which was collected by filtration, washed with water and dried in high vacuum. The product was used as such or was recrystallized as shown in Table B.

General Method D

A mixture of the appropriate 1H-pyrazole, one equivalent of the appropriate amidine hydrochloride, 1–2 equivalents of potassium carbonate and 800–500 ml of N-methyl-2-pyrrolidinone per mole of pyrazole were combined and heated to 120°–160° C. for 32–60 hours. The reaction mixture was cooled to room temperature, poured into 100–800 ml of cold water and stirred for 0.5–1 hour. A precipitate forms which was collected by filtration and washed with water. The product was used as such directly in subsequent reactions or it was purified by column chromatography on silica or by recrystallization. The results are summarized in Table B.

TABLE B

[Reaction scheme: pyrazole-4-carbonitrile with R³ at 3-position, H₂N at 5-position, R¹ on N1 + R⁶-C(=NH)-NH₂·HCl → pyrazolo[3,4-d]pyrimidine with 4-NH₂, R³, R⁶, R¹ substituents]

| Example No. | R¹ | R³ | R⁶ | Method | Yield % | Melting Range °C. | Chromatography Solvent | Recrystallized From |
|---|---|---|---|---|---|---|---|---|
| 38 | H | H | 4-pyridyl | C | 50 | >340 | — | EtOH |
| 39 | H | Me | 4-pyridyl | C | 62 | — | — | — |
| 40 | H | Et | 4-pyridyl | C | 30 | >300 | — | DMF |
| 41 | cyclobutyl | Me | 4-pyridyl | D | 43 | 199–200 | Et₂O/hexanes → Et₂O 50/50 → 100 | iPrOH |
| 42 | tetrahydrofuran-3-yl | Me | 4-pyridyl | D | 28 | 179–180 | — | — |
| 43 | norbornyl | Me | 4-pyridyl | D | 13 | 211–212 | hexanes/Et₂O 50/50 | — |
| 44 | $(CH_3)_3C$ | Me | 4-pyridyl | C | 30 | 216–218 | — | EtOH |
| 45 | $(CH_3)_3C$ | Et | 4-pyridyl | C | 15 | 181–184 | — | cyclohexane |
| 46 | cyclopentyl | $(CH_3)_3C$ | 4-pyridyl | D | 34 | 199–200 | Et₂O/cyclohexane 50/50 | — |
| 47 | cyclopentyl | CF₃ | 4-pyridyl | C | 37 | — | — | — |

TABLE B-continued

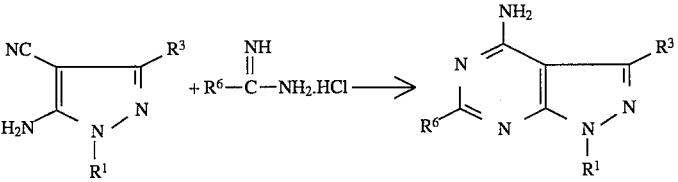

| Example No. | R¹ | R³ | R⁶ | Method | Yield % | Melting Range °C. | Chromatography Solvent | Recrystallized From |
|---|---|---|---|---|---|---|---|---|
| 48 | H | CN | 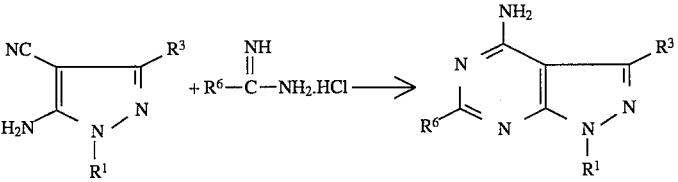 | C | 37 | — | — | — |
| 49 | 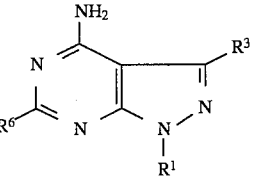 | Me |  | D | 14 | 265–266 | Et₂O → Et₂O/Acetone 100 → 50/50 | CH₃CN |
| 50 | 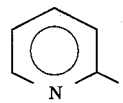 | Me | 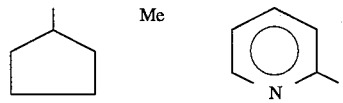 | C | 47 | 191–192 | Et₂O/cyclohexane 50/50 | — |

General Method E

To a mixture of one equivalent of a 60% to 97% NaH/mineral oil dispersion in 2 l of DMF per mole of pyrimidine under nitrogen at 10° to 25° C. was added in portions the appropriate pyrazolo[3,4-d]pyrimidine. The reaction mixture was heated to 50–85° C. and one equivalent of the appropriate halide was added dropwise. The reaction mixture was heated to reflux and stirred for 5–24 hours. The reaction mixture was cooled and poured into 1–2.5 l of water. At this stage either 1) the mixture was extracted with ether or ethyl acetate, the organic layers were combined and concentrated in vacuo or 2) the desired product precipitated out of solution and could be collected by filtration. The residue was purified by column chromatography on silica and/or by recrystallization. The results are summarized in Table C.

General Method F

To a mixture of the appropriate pyrazolo[3,4-d]pyrimidine in 2–3 l of DMF per mole of pyrimidine at 0°–25° C. under argon was added one equivalent of 60% NaH. The reaction mixture was stirred for 1–2 hours then one equivalent of the appropriate halide was added. The reaction mixture was stirred at room temperature for 24–80 hours. The reaction mixture was added slowly to 200–700 ml of water and was stirred for 30–90 minutes. The resulting precipitate was collected by filtration and the solid was purified by column chromatography on silica and/or by recrystallization. The results are summarized in Table C.

General Method G

One equivalent of 60% NaH/mineral oil dispersion was washed with hexanes and the residual solvent removed to afford mineral oil free sodium hydride. 200–600 ml of DMF per mole of hydride was added to the sodium hydride under argon, followed by addition of the appropriate pyrazolo[3,4-d]pyrimidine in DMF or as a solid. The reaction mixture was stirred at room temperature for 10–60 minutes and one equivalent of the appropriate halide in 60–500 ml of DMF per mole of pyrimidine was added. The reaction mixture was stirred at room temperature for 3–60 hours and poured into 1–2 L of cold water. The resulting precipitate was collected by filtration and washed with water, then ether. The product was purified by column chromatography on silica and/or by recrystallization. The results are summarized in Table C.

TABLE C

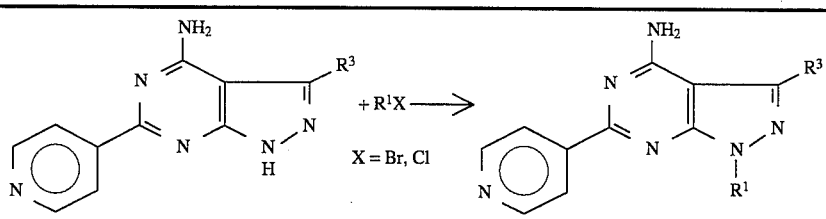

| Example No. | R³ | R¹ | X | Method | Yield % | Melting Range °C. | Chromatography Solvent | Recrystallized From |
|---|---|---|---|---|---|---|---|---|
| 51 | H | cyclopentyl | Br | E | 25 | 215–217 | EtOAc/hexanes → EtOAc | CH₃CN |
| 52 | Et | cyclopentyl | Br | E | 58 | 158–160 | Et₂O | — |
| 53 | Me | PhCH₂ | Br | E | 68 | 250–255 | — | DMF |
| 54 | Me | EtO₂C—(CH₂)₈— | Br | F | 66 | 62–63 | Et₂O → Et₂O/Acetone 100 → 50/50 | — |
| 55 | Me | EtO₂C—(CH₂)₆— | Br | F | 55 | 73–74 | Et₂O → EtOAc → Acetone | — |
| 56 | Me | EtO₂C—(CH₂)₅— | Br | F | 68 | 95–96 | Et₂O → Acetone | cyclohexane |
| 57 | Me | 3-Cl-C₆H₄-CH₂ | Cl | E | 52 | 217–219 | — | EtOH⁽ᵃ⁾ |
| 58 | Me | 2-Cl-C₆H₄-CH₂ | Cl | E | 56 | 216–219 | — | EtOH⁽ᵃ⁾ |
| 59 | Me | cyclopentyl | Br | E | 51 | — | — | EtOAc⁽ᵇ⁾ |
| 60 | Me | EtO₂C—(CH₂)₇— | Br | F | 67 | 49–50 | Et₂O → EtOAc → Acetone | — |
| 61 | Me | 4-CN-2-CH₃-C₆H₃-CH₂ | Br | G | 64 | — | — | CH₃CN |
| 62 | Me | 3-CN-C₆H₄-CH₂ | Br | G | 72 | — | — | CH₃CN |
| 63 | Me | 2-CH₃-C₆H₄-CH₂ | Br | G | 45 | — | — | CH₃CN |
| 64 | Me | n-octyl | Br | G | 77 | — | EtOAc/hexanes 50/50 | — |

⁽ᵃ⁾Upon addition of the crude reaction mixture to boiling ethanol an insoluble solid was isolated which was characterized as the N(2) alkylated isomer. The desired product was isolated from the ethanol filtrate upon cooling.
⁽ᵇ⁾Insoluble solid characterized as N(2) alkylated isomer was isolated from the boiling ethyl acetate. The desired product was isolated from the filtrate upon cooling.

EXAMPLE 65

1-Cyclopentylmethyl-3-methyl-6-(4-pyridyl)pyrazolo [3,4-d]pyrimidin-4-amine

To a solution of 3-methyl-6-(4-pyridyl)-pyrazolo[3,4-d] pyrimidin-4-amine (6.0 g, 0.027 mol) in DMF (50 ml) at 0° C. was added 60% NaH/mineral oil dispersion (1.06 g, 0.027 mol) in one portion. The reaction mixture was warmed to room temperature and stirred for 1 hour. The reaction mixture was cooled to 0° C. and cyclopentylmethyl bromide (4.3 g, 0.027 mol) was added dropwise over 5 minutes. The reaction mixture was warmed to room temperature and stirred for 50 hours. The solvent was removed in vacuo, the yellow slurry was added to water (100 ml) and acidified with acetic acid. The resulting paste was stripped to dryness and the residue was slurried with ethanol. A tan solid was collected by filtration and purified by column chromatography on silica eluting with ether/ethanol/water (97.5/2/0.5) followed by recrystallization from cyclohexane to afford 2.2 g (26%) of 1-cyclopentylmethyl-3-methyl-6-(4-pyridyl)-pyrazolo[3,4-d]-pyrimidin-4-amine, m.p. 177°–178° C.

EXAMPLE 66

1-(3-Diethylaminopropyl)-3-methyl-6-(4-pyridyl) pyrazolo(3,4-d)pyrimidin-4-amine To a suspension of 3-methyl-6-(4-pyridyl)-pyrazolo-[3,4-d]pyrimidin-4-amine (4.09 g, 18.1 mmol) in DMF (35 ml) under argon was added 60% NaH/mineral oil dispersion (1.5 g, 38.0 mmol). The reaction mixture was stirred at room temperature for 45 minutes, heated to 60° C. and 3-diethylaminopropyl chloride hydrochloride (3.0 g, 19.9 mmol) in DMF (15 ml) was added. The reaction mixture was heated at 60°–70° C. for 3 hours, cooled to room temperature and the solvent was removed in vacuo. The residue was partitioned between aqueous HCl (pH=4) and chloroform and the aqueous layer was separated and neutralized with ammonium hydroxide. The aqueous layer was extracted with ether (3×100 ml) and the organic layer was dried over $MgSO_4$ and concentrated in vacuo. The residue was purified by column chromatography on silica eluting with chloroform/methanol/i-$PrNH_2$ (92.5/2.5/5) to afford 1.7 g (27%) of 1-(3-diethylaminopropyl)-3-methyl-6-(4pyridyl)-pyrazole[3,4-d]pyrimidin-4-amine.

Example 67

1-Cyclopentyl-3-cyano-6-(4-pyridyl)pyrazolo [3,4-d]pyrimidin-4-amine

To a suspension of 97% NaH (0.64 g, 0.026 mol) in DMF (75 ml) was added 3-cyano-6-(4-pyridyl)-pyrazolo [3,4-d] pyrimidin-4amine (4.7 g, 0.02 mol). The reaction mixture was stirred at room temperature for 30 minutes then cyclopentyl bromide (3.1 g, 0.021 mol) in DMF (25 ml) was added dropwise. The reaction mixture was heated on a steam bath for 3 hours, cooled to room temperature and stirred for 24 hours. Inorganic salts were removed by filtration and the filtrate was concentrated in vacuo. The residue was purified by column chromatography on silica eluting with ethyl acetate (100%) followed by preparative thin layer chromatography on silica eluting with ethyl acetate/hexanes (75/25) to afford 0.45 g (7%) of 1-cyclopentyl-3-cyano-6-(4-pyridyl)-pyrazolo[3,4-d]pyrimidin-4-amine, m.p. 219°–221° C. when recrystallized from ether and dried for 16 hours at 90° C. in high vacuum.

EXAMPLE 68

1-Cyclopentyl-3-chloro-6-(4-pyridyl)pyrazolo[3,4-d] pyrimidin-4-amine

Into a solution of 1-cyclopentyl-6-(4-pyridyl)pyrazolo(3,4-d)pyrimidin-4-amine (3.0 g, 0.011 mol) in water (60 ml) heated on a steam bath was bubbled chlorine gas for ¾ hour. The reaction mixture was cooled to room temperature and the solvent was removed in vacuo. Water, ammonium hydroxide and acetic acid were added to the residue, the residue was filtered and the filtrate was taken up in ethyl acetate. The organic layer was concentrated in vacuo and the residue was purified by column chromatography on silica eluting with hexanes/ethyl acetate (1/1) to afford, after recrystallization from ether, 0.54 g (16%) of 1-cyclopentyl-3-chloro-6-(4-pyridyl)-pyrazolo[3,4-d]pyrimidin-4-amine, m.p. 132°–134° C. when dried for 16 hours at 85° C. in high vacuum.

EXAMPLE 69

1-Cyclopentyl-3-bromo-6-(4-pyridyl)pyrazolo[3,4-d] pyrimidin-4-amine

To a solution of 1-cyclopentyl-6-(4-pyridyl)-pyrazolo-(3, 4-d) pyrimidin-4-amine (3.0 g, 0.011 mole) in water 60 ml) at room temperature was added bromine (1.8 g, 0 011 mol). The reaction mixture was stirred at room temperature for 1 hour, then was heated on a steam bath for 2 hours. The solvent was removed in vacuo and the residue was suspended in water. Ammonium hydroxide was added followed by acetic acid until a pH of 4–5 was obtained. A solid was collected by filtration and washed with water. Water (60 ml) and bromine (0.3 ml, 0.006 mol) were added to the solid residue and the mixture was heated on a steam bath for 1 hour. The mixture was poured into ice-water and ammonium hydroxide, then acetic acid was added. A solid was collected by filtration, dissolved in ethyl acetate, dried over $MgSO_4$ and concentrated in vacuo to afford 2.2 g (56%) of 1-cyclopentyl-3-bromo-6-(4-pyridyl)-pyrazolo [3,4-d]pyrimidin-4-amine, m.p. 189°–191° C.

EXAMPLE 70

1-Cyclopentyl-3-nitro-6-(4-pyridyl)pyrazolo[3,4-d] pyrimidin-4-amine

To a solution of 1-cyclopentyl-6-(4-pyridyl)pyrazolo[3,4-d]pyrimidin-4-amine (4.6 g, 0.016 mol) in sulfuric acid (60 ml) in an ice-bath was added dropwise 70% nitric acid (36.8 ml). The reaction mixture was warmed to room temperature, stirred for 30 minutes then heated on a steam bath for ¾ hour. The reaction mixture was added to ice-water/50% sodium hydroxide and the pH was adjusted to 4–5 with acetic acid. The product was collected by filtration and washed with water. The solid residue was purified by preparative thin layer chromatography on silica eluting with ethyl acetate (100%) to afford, after recrystallization from ethyl acetate, 0.81 g (16%) of 1-cyclopentyl-3-nitro-6-(4-pyridyl)-pyrazolo[3,4-d]pyrimidin-4-amine, m.p. 239°–241° C. when dried for 16 hours at 110° C. in high vacuum.

General Method H

To a solution of the appropriate pyrazolo [3,4-d]-pyrimidin-4-amine in 2–10 l of 1/1 mixture of sulfuric acid/water per mole of pyrimidin-4-amine at −10°–5° C. was added dropwise 2–10 equivalents of sodium nitrite in 0.5–5 l of water per mole of pyrimidin-4-amine. The reaction mixture was warmed to room temperature and stirred for 24 hours. Concentrated ammonium hydroxide was added to the reaction mixture until the solution was slightly basic and the product was collected by filtration and washed with water, then ether. The product was purified by recrystallization. The results are summarized in Table D.

General Method I

To a solution of the appropriate pyrazolo[3,4-d]pyrimidin-4-amine in 5–13 l of a 1/1 mixture of sulfuric acid/water per mole of pyridine-4-amine at 0°–5° C. was added dropwise over 30–45 minutes, 10–21 equivalents of sodium nitrite in 1–4.5 l of water per mole of pyrimidin-4-amine. The reaction mixture was warmed to room temperature and stirred for 2–24 hours. The mixture was poured into ice-water, ammonium hydroxide was added until pH of 9, followed by acetic acid until a pH of 4–5 was obtained. The product was collected by filtration and washed with water. The product was purified by recrystallization. The results are summarized in Table D.

General Method J

A solution of the appropriate pyrazolo[3,4-d]pyrimidin-4-amine in 1–10 l of 50–75% sulfuric acid per mole of pyrimidin-4-amine was stirred at room temperature for 0–1.5 hours, then cooled to −15°–0° C. 7–23 equivalents of sodium nitrite in 0.5–2 l of water per mole of pyrimidin-4-amine was then added and the reaction mixture was warmed to room temperature and stirred for 18–60 hours. The mixture was poured onto ice-water, neutralized with $K_2CO_3$, the salts were filtered and the pH of the filtrate was adjusted to 4–5 with acetic acid. The product was collected by filtration and dried. The product was purified by recrystallization. The results are summarized in Table D.

General Method K

A solution of the appropriate pyrazolo[3,4-d]pyrimidin-4-amine in 1.5–7 l of 32% sulfuric acid per mole of pyrimidin-4-amine was cooled to 0°–5° C. and 2–3 equivalents of sodium nitrite in 200–2000 ml of water per mole of pyrimidin-4-amine was added dropwise over 20 minutes to 3 hours. The reaction mixture was stirred at 5° C. for 25–30 minutes then was heated to reflux for 0.5–1.5 hours. The reaction mixture was cooled in an ice-bath and the product was collected by filtration. The solid residue was suspended in water and the solution was basified with concentrated ammonium hydroxide. The product was collected by filtration and washed with water. The product was purified by recrystallization. The results are summarized in Table D.

General Method L

The reaction was run as described in General Method J except the reaction was worked up as follows: the reaction mixture was poured into ice-water, neutralized with $K_2CO_3$ and the product was collected by filtration and washed with water. The product was purified by recrystallization. The results are summarized in Table D.

General Method M

A solution of the appropriate pyrazolo[3,4-d]pyrimidin-4-amine in 3–4 l of 50% sulfuric acid per mole of pyrimidin-4-amine was cooled to −10°–0° C. and 5 equivalents of sodium nitrite in 300–650 ml of water per mole of pyrimidin-4-amine was added dropwise over 1 hour. The reaction mixture was stirred at −10°–0° C. for 4 hours, then at room temperature for 24 hours. The reaction mixture was poured onto ice-water and the product was collected by filtration and washed with water, ethanol, then ether. The product was purified by recrystallization. The results are summarized in Table D.

General Method N

The reaction was run as described in General Method K except that the reaction mixture was stirred at room temperature for 24 hours rather than at reflux for 0.5–1.5 hours. The results are summarized in Table D.

TABLE D

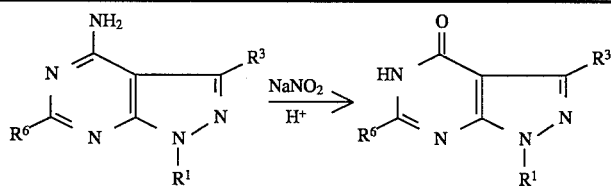

| Example No. | R¹ | R³ | R⁶ | Method | Yield % | Melting Range °C. | Recrystallized From |
|---|---|---|---|---|---|---|---|
| 71 |  | H |  | H | 49 | 262.5–264 | $CH_3OH$ |
| 72 |  | Cl |  | I | 45 | >300 | DMF |

TABLE D-continued

| Example No. | R¹ | R³ | R⁶ | Method | Yield % | Melting Range °C. | Recrystallized From |
|---|---|---|---|---|---|---|---|
| 73 | cyclopentyl | Br | 4-pyridyl | I | 74 | >300 | DMF |
| 74 | cyclopentyl | NO₂ | 4-pyridyl | I | 50 | >300 | DMF |
| 75[a] | cyclopentyl | Et | 4-pyridyl | H | 65 | 269–270 | DMF |
| 76 | H | Me | 4-pyridyl | L | 71 | >365 | DMF |
| 77 | CH₂-phenyl | Me | 4-pyridyl | K | 47 | >300 | DMF |
| 78[b] | EtO₂C—(CH₂)₈— | Me | 4-pyridyl | J | 86 | 211–212 | isopropanol |
| 79[c] | EtO₂C—(CH₂)₆— | Me | 4-pyridyl | J | 82 | 196–197 | isopropanol |
| 80[d] | EtO₂C—(CH₂)₅— | Me | 4-pyridyl | J | 11 | 276–277 | isopropanol then methanol |
| 81[e] | CH₂-(3-chlorophenyl) | Me | 4-pyridyl | L | 17 | 289–290 | EtOH |
| 82 | CH₂-(2-chlorophenyl) | Me | 4-pyridyl | K | 60 | 293–294 | DMF |

TABLE D-continued

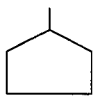

| Example No. | R¹ | R³ | R⁶ | Method | Yield % | Melting Range °C. | Recrystallized From |
|---|---|---|---|---|---|---|---|
| 83 | cyclopentyl | Me | 4-pyridyl | K | 65 | >300 | DMF |
| 84[f] | EtO$_2$C—(CH$_2$)$_7$— | Me | 4-pyridyl | J | 96 | 204–205 | isopropanol |
| 85 | 4-CN-C$_6$H$_4$-CH$_2$— | Me | 4-pyridyl | M | 88 | >300 | DMF |
| 86[g] | 3-CN-C$_6$H$_4$-CH$_2$— | Me | 4-pyridyl | M | 83 | >300 | DMF |
| 87 | 2-CH$_3$-C$_6$H$_4$-CH$_2$— | Me | 4-pyridyl | H | 78 | 297–298 | DMF |
| 88 | n-octyl | Me | 4-pyridyl | H | 39 | 185–186 | EtOAc |
| 89 | cyclopentyl-CH$_2$— | Me | 4-pyridyl | L | 82 | 253 | isopropanol |
| 90 | (CH$_3$)$_3$C | C$_6$H$_5$-CH$_2$— | 4-pyridyl | N | 54 | 237–239 | EtOH |
| 91 | norbornyl | Me | 4-pyridyl | L | 50 | 301–302 | isopropanol then CH$_3$CN |
| 92 | (CH$_3$)$_3$C | H | 4-pyridyl | N | 93 | >300 | — |

TABLE D-continued

[Reaction scheme: 4-amino pyrazolo[3,4-d]pyrimidine with NaNO₂/H⁺ converting to the 4-one]

| Example No. | R¹ | R³ | R⁶ | Method | Yield % | Melting Range °C. | Recrystallized From |
|---|---|---|---|---|---|---|---|
| 93 | (CH₃)₃C | Me | 4-pyridyl | H | 96 | 300–301 | MeOH |
| 94 | (CH₃)₃C | Et | 4-pyridyl | H | 88 | 275–276.5 | DMF |
| 95 | cyclopentyl | (CH₃)₃C | 4-pyridyl | L | 67 | 281 (dec) | isopropanol |
| 96 | cyclopentyl | CF₃ | 4-pyridyl | I | 80 | >300 | EtOH |
| 97[h] | cyclopentyl | Me | 2-methylpyridyl | L | 96 | 162–163 | isopropanol |
| 98[i] | cyclopentyl | Me | 3-pyridyl | L | 98 | 263 | isopropanol |

[a] product isolated as ¼ hydrate.
[b] product isolated as the acid [CH₂(CH₂)₇CO₂H] not the ester.
[c] product isolated as the acid [CH₂(CH₂)₅CO₂H] not the ester.
[d] product isolated as the acid [CH₂(CH₂)₄CO₂H] not the ester, and as the ¼ hydrate.
[e] product isolated as ½ hydrate.
[f] product isolated as the acid [CH₂(CH₂)₆CO₂H] not the ester.
[g] product isolated as ¹/₁₀ hydrate.
[h] product isolated as the ⅛ hydrate.
[i] product isolated as the ⅓ hydrate.

EXAMPLE 99

1-(3-Diethylaminopropyl)-3-methyl-6-(4-pyridyl) pyrazolo[3,4-d]pyrimidin-4-one.½ hydrate A solution of 1-(3-diethylaminopropyl)-3-methyl-6-(4-pyridyl)pyrazolo[3,4-d]pyrimidin-4-amine in 50% sulfuric acid (25 ml) was cooled to 0° C. and stirred for 1 hour. A solution of sodium nitrite (0.78 g, 11.4 mmol) in water (5–7 ml) was added and the reaction mixture was stirred at 0° C. for 4 hours, then at room temperature for 24 hours. The reaction mixture was poured onto ice-water, treated with ammonium hydroxide and the pH adjusted to 7 with acetic acid. The aqueous layer was extracted with chloroform (4×250 ml) and the combined organic layers were dried over MgSO₄ and concentrated in vacuo. The residue was recrystallized in tert-butylmethyl ether/chloroform to afford 0.51 g (66%) of 1-(3-diethylaminopropyl)-3-methyl-6-(4-pyridyl)pyrazolo-[3,4-d]pyrimidin-4-one-½ hydrate as an off-white powder, m.p. 164°–166° C. when dried at 80° C. for 16 hours in high vacuum.

EXAMPLE 100

1-Cyclopentyl-3-cyano-6-(4-pyridyl)-pyrazolo-[3,4-d]pyrimidin-4-one

To a solution of 1-cyclopentyl-3-cyano-6-(4-pyridyl)pyrazolo(3,4-d)pyrimidin-4-amine (0.61 g, 2.0 mmol) in 50% acetic acid (70 ml) at −5 to 0° C. was added 50% trifluoroacetic acid (10 ml) followed by sodium nitrite (2.8 g, 40.6 mmol) in water (15 ml). The reaction mixture was stirred at −5 to 0° C. for 1 hour, then at room temperature for 3 hours. The reaction mixture was cooled back to −5 to 0°

C. and sodium nitrite (1.4 g, 20.3 mmol) in water (5 ml) was added. The reaction mixture was warmed to room temperature and stirred for 3 hours. The mixture was poured onto ice-water, concentrated ammonium hydroxide was added, followed by acetic acid to adjust the pH to 5. The product was collected by filtration, washed with water and recrystallized from ethanol to afford 0.48 g (79%) of 1-cyclopentyl-3-cyano-6-(4-pyridyl) pyrazolo[3,4-d]pyrimidin-4-one as a white fluffy powder, m.p. >300° C. when dried at 110° C. for 96 hours in high vacuum.

EXAMPLE 101

1-(3-Tetrahydrofuranyl)-3-methyl-6-(4-pyridyl)-pyrazolo-[3,4-d]pyrimidin-4-one-¼ hydrate To a solution of 1-(3-tetrahydrofuranyl)-3-methyl-6-(4-pyridyl)-pyrazolo[3,4-d]pyrimidin-4-amine (1.08 g, 3.6 mmol) in 60% sulfuric acid (30 ml) at −10° C. was added sodium nitrite (5.6 g, 81.2 mmol) in water (8 ml). The reaction mixture was stirred at −5° C. for 2 hours, then at room temperature for 24 hours. The mixture was poured onto ice-water, neutralized with $K_2CO_3$ and the salts were collected by filtration. The aqueous filtrate was extracted with chloroform (6×100 ml) and the combined organic layers were concentrated in vacuo. The residue was dissolved in isopropanol, treated with Darco and concentrated in vacuo to afford 0.5 g (46%) of 1-(3-tetrahydrofuranyl)-3-methyl-6-(4-pyridyl)pyrazolo[3,4-d]pyrimidin-4-one.¼ hydrate as an off-white fluffy powder, m.p. 251° C. when dried at 90° C. for 24 hours in high vacuum.

EXAMPLE 102

1-Cyclobutyl-3-methyl-6-(4-pyridyl)-pyrazolo-[3,4-d]pyrimidin-4-one

To a solution of 1-cyclobutyl-3-methyl-6-(4-pyridyl)pyrazolo[3,4-d]pyrimidin-4-amine (1.5 g, 5.3 mmol) in 75% aqueous sulfuric acid (25 ml) cooled in an ice-bath was added sodium nitrite (4.0 g, 58.0 mmol) in water (3 ml). The reaction mixture was warmed to room temperature, stirred for 24 hours and then warmed to 50° C. for 2 hours. The mixture was cooled in an ice-bath and sodium nitrite (4.2 g, 61.0 mmol) in water (5 ml) was added. The reaction mixture was warmed to room temperature and stirred for 24 hours. The mixture was poured onto ice-water and neutralized with $K_2CO_3$. The product was collected by filtration and recrystallized from isopropanol to afford 1.2 g (81%) of 1-cyclobutyl-3-methyl-6-(4-pyridyl)-pyrazolo[3,4-d]pyrimidin-4-one as an off-white powder, m.p. 289°–90° C. when dried at 45° C. in high vacuum.

EXAMPLE 103

1,3-Dimethyl-6-(4-pyridyl)-pyrazolo-[3,4-d]pyrimidin-4-one

A solution of 1,3-dimethyl-6-(4-pyridyl)-pyrazolo[3,4-d]-pyrimidin-4-amine (1.99 g, 8.3 mmol) in 50% aqueous sulfuric acid (50 ml) at 0° C. was stirred for 20 minutes and sodium nitrite (5.7 g, 83.0 mmol) in water (25 ml) was added dropwise over 1 hour. The reaction mixture was allowed to warm to room temperature and was stirred for 24 hours. The mixture was poured into ice-water (500 ml) and a white solid was collected by filtration and washed with water, ethanol and finally ether. The solid residue was stirred in 15% $KHCO_3$ (150 ml) for 20 minutes and the product was collected by filtration and washed with water, then ethanol and finally ether. The product was recrystallized from DMF to afford 1.5 g (76%) of 1,3-dimethyl-6-(4-pyridyl)-pyrazolo [3,4-d]-pyrimidin-4-one as a white solid, m.p. >301° C. when dried for 18 hours at 115° C. in high vacuum.

EXAMPLE 104

1-(2-Tetrahydrofuranyl)-3-methyl-6-(4-pyridyl) pyrazolo[3,4-d]pyrimidin-4-one A solution of 3-methyl-6-(4-pyridyl)-pyrazolo[3,4-d]-pyrimidin-4-one (2.3 g, 0.01 mol), DMF (50 ml) and 2,3-dihydrofuran (14.0 g, 0.20 mol) was stirred at 0° C. for 10 minutes and $BF_3.Et_2O$ (1.5 ml, 0.012 mol) was added dropwise. The reaction mixture was warmed to room temperature and stirred for 108 hours. The reaction was quenched with concentrated ammonium hydroxide until pH of 7.5 and the resulting precipitate was collected by filtration. The solid residue was taken up in isopropanol (200 ml), heated to reflux and filtered to remove insoluble material. Concentration of the filtrate to 75 ml and cooling caused precipitation of the product. The product was collected by filtration and washed with ether to afford 1.1 g (37%) of 1-(2-tetrahydrofuranyl)-3-methyl-6-(4-pyridyl)-pyrazolo-[3,4-d]pyrimidin-4-one as a white powder, m.p. 268°–9° C. when dried at 70° C. in high vacuum.

EXAMPLE 105

1-(4-Nitrophenylmethyl)-3-methyl-6-(4-pyridyl) pyrazolo[3,4-d]pyrimidin-4-one To a solution of 90% nitric acid (30 ml) at −12°–0° C. was added in small portions 1-phenylmethyl-3-methyl-6-(4-pyridyl)pyrazolo[3,4-d]pyrimidin-4-one (2.99 g, 9.4 mmol). The reaction mixture was stirred at 0° C. for 2.5 hours and then poured slowly into ice-water. The solution was neutralized with concentrated ammonium hydroxide to afford a yellow solid which was collected by filtration and washed with water, ethanol and finally ether. The product was recrystallized from ethyl acetate/ethanol (3×) to afford 3.2 g (91%) of 1-(4-nitrophenylmethyl)-3-methyl-6-(4-pyridyl)pyrazolo(3,4-d)pyrimidin-4-one as a white powder which is contaminated with a small amount of the meta isomer (ratio para/meta is 93/7). The mixture had a melting point of 275°–281° C. when dried at 125° C. for 24 hours in high vacuum.

EXAMPLE 106

1-(2-Chloro-5-nitrophenylmethyl)-3-methyl-6-(4-pyridyl)pyrazolo[3,4-d]pyrimidin-4-one To a solution of 90% nitric acid (30 ml) at −10° C. was added in portions over 4 hours 1-(2-chlorophenylmethyl)-3-methyl-6-(4-pyridyl)pyrazolo[3,4-d]pyrimidin-4-one (4.9 g, 0.014 mol). The mixture was stirred at −10° C. for 30 minutes and poured into ice-water. The product was collected by filtration and washed with water. The solid residue was dissolved in methanol/DMF (3/1), treated with charcoal and the solvent was concentrated in vacuo. Ether was added to the residue and the product was collected by filtration and washed with ether to afford 5.5 g (99%) of 1-(2-chloro-5-nitrophenylmethyl)-3-methyl-6-(4-pyridyl)pyrazolo[3,4-d] pyrimidin-4-one as an off-white powder, m.p. 290°–1° C. when dried at 80° C. in high vacuum.

EXAMPLE 107

1-(2-Chloro-5-aminophenylmethyl)-3-methyl-6-(4-pyridyl)pyrazolo[3,4-d]pyrimidin-4-one dihydrochloride salt To a solution of 1-(2-chloro-4-nitrophenylmethyl)-3-methyl-6-(4-pyridyl)-pyrazolo[3,4-d]pyrimidin-4-one (4.4 g, 0.01 mol), ethanol (67 ml), water (27 ml) and $SnCl_2.H_2O$ (7.4 g, 0.03 mol) at room temperature was added concentrated HCl (40.2 ml) over 10 minutes. The reaction mixture was heated to reflux for 2 hours, cooled to room temperature and stirred for 24 hours. The product was collected by filtration and washed with ethanol, then ether to afford 4.2 (87%) of 1-(2-chloro-5-aminophenylmethyl)-3-methyl-6-(4-pyridyl)-pyrazolo[3,4-d]pyrimidin-4-one dihydrochloride salt as pale yellow crystals, m.p. 292° C. (dec.).

EXAMPLE 108

1-[2-Chloro-5-((8-quinolinylsulfonyl)amino)phenylmethyl]-3-methyl-6-(4-pyridyl)-pyrazolo[3,4-d]pyrimidin-4-one A solution of 1-(2-chloro-5-aminophenylmethyl)-3-methyl-6-(4-pyridyl)-pyrazolo[3,4-d]pyrimidin-4-one dihydrochloride salt (0.55 g, 1.4 mmol), pyridine (10 ml) and triethylamine (0.18 ml, 1.36 mmol) was stirred at 0° C. under argon for 20 minutes and dimethylaminopyridine (0.016 g, 0.14 mmol) and 8-quinoline sulfonyl chloride (0.37 g, 1.6 mmol) were added. The mixture was stirred at 0° C. for 2.5 hours and poured into ice-water with stirring. The product was collected by filtration to afford 0.66 g (88%) of 1-[2-chloro-5-((8-quinolinylsulfonyl)amino)phenylmethyl]-3-methyl-6-(4-pyridyl)-pyrazolo[3,4-d]pyrimidin-4-one as a tan powder, m.p. 325° C. (dec.) when dried at 100° C. for 24 hours in high vacuum.

EXAMPLE 109

1-Cyclopentyl-3-methyl-6-(4-piperidinyl)-pyrazolo[3,4-d]-pyrimidin-4-one monohydrochloride.½ hydrate A mixture of 1-cyclopentyl-3-methyl-6-(4-pyridyl)pyrazolo[3,4-d]pyrimidin-4-one (1.0 g, 3.3 mmol), acetic acid (50 ml) and platinum oxide (0.2 g) was hydrogenated at 45 psi on a parr hydrogenator with external heating at about 70° C. for 2 hours. The mixture was cooled and the catalyst was removed by filtration. Concentrated HCl (15 ml) was added to the filtrate and the solvent was removed in vacuo. The solid residue was recrystallized from ethanol to afford 0.72 g (73%) of 1-cyclopentyl-3-methyl-6-(4-piperidinyl)-pyrazolo[3,4-d]pyrimidin-4-one monohydrochloride.½ hydrate as an off-white powder, m.p. >300° C. when dried at 85° C. in high vacuum.

EXAMPLE 110

1-(4-Carbamoylphenylmethyl)-3-methyl-6-(4-pyridyl)pyrazolo[3,4-d]pyrimidin-4-one A solution of potassium hydroxide (0.24 g, 3.7 mmol) in water (10 ml) was stirred in an ice-bath for 30 minutes and 1-(4-cyanophenylmethyl)-3-methyl-6-(4-pyridyl)-pyrazolo[3,4-d]-pyrimidin-4-one (0.42 g, 1.2 mmol) was added, followed by 30% hydrogen peroxide (0.6 ml, 6.1 mmol). The reaction mixture was stirred for 4 hours, warmed to room temperature and stirred for 24 hours. The reaction mixture was filtered, and the filtrate was neutralized with acetic acid to afford a white precipitate. The product was collected by filtration and washed with water, ethanol and ether. The product was recrystallized in DMF to afford 0.2 g (46%) of 1-(4-carbamoylphenylmethyl)-3-methyl-6-(4-pyridyl)-pyrazolo[3,4-d]pyrimidin-4-one as a fluffy white powder, m.p. >300° C. when dried at 120° C. for 24 hours in high vacuum.

EXAMPLE 111

1-(4-Carboxylphenylmethyl)-3-methyl-6-(4-pyridyl)-pyrazolo[3,4-d]pyrimidin-4-one A mixture of 1-(4-cyanophenylmethyl)-3-methyl-6-(4-pyridyl)-pyrazolo[3,4-d]pyrimidin-4-one (1.6 g, 4.5 mmol), 10M NaOH (50 ml) and ethanol (50 ml) was refluxed for 4 hours. The mixture was filtered while hot, the filtrate was cooled and acidified with acetic acid (pH 6). The product was collected by filtration and washed with ethanol and ether. The product was recrystallized from DMF to afford 0.26 g (16%) of 1-(4-carboxyphenylmethyl)-3-methyl-6-(4-pyridyl)-pyrazolo[3,4-d]pyrimidin-4-one as an off-white powder, m.p. >300° C. when dried at 120° C. for 18 hours in high vacuum.

EXAMPLE 112

1-(3-Carboxyphenylmethyl)-3-methyl-6-(4-pyridyl)-pyrazolo[3,4-d]pyrimidin-4-one A mixture of 1-(3-cyanophenylmethyl)-3-methyl-6-(4-pyridyl)-pyrazolo[3,4-d]pyrimidin-4-one (3.4 g, 10.2 mmol), 10 M NaOH (100 ml) and ethanol (100 ml) was refluxed for 7 hours. The mixture was filtered hot, the filtrate was cooled in an ice-bath for 30 minutes and neutralized with acetic acid. The product was collected by filtration and washed with water, ethanol and ether. The solid residue was digested in methanol and the product was collected by filtration and washed with ether. The product was recrystallized from DMF to afford 0.91 g (25%) of 1-(3-carboxyphenylmethyl)3-methyl-6-(4-pyridyl)-pyrazolo[3,4-d]pyrimidin-4-one as an off-white powder, m.p. >300° C. when dried at 125° C. for 18 hours in high vacuum.

EXAMPLE 113

1-(3-Carbamoylphenylmethyl)-3-methyl-6-(4-pyridyl)pyrazolo[3,4-d]pyrimidin-4-one A mixture of potassium hydroxide (0.7 g, 9.9 mmol) in water (75 ml) was stirred in an ice-bath for 30 minutes and 1-(3-cyanophenylmethyl)-3-methyl-6-(4-pyridyl)-pyrazolo[3,4-d]-pyrimidin-4-one (1.1 g, 3.3 mmol), followed by 30% hydrogen peroxide (1.7 ml, 16.5 mmol) were added. The mixture was slowly warmed to room temperature and stirred for 24 hours. The mixture was chilled in an ice-bath and neutralized with acetic acid. The product was collected by filtration and washed with water, ethanol and ether. The product was recrystallized from DMF to afford 0.87 g (73%) of 1-(3-carbamoylphenylmethyl)-3-methyl-6-(4-pyridyl)-pyrazolo[3,4-d]pyrimidin-4-one as an off-white powder, m.p. >300° C. when dried at 120° C. for 24 hours in high vacuum.

EXAMPLE 114

Following a procedure substantially similar to that described in Example 16, parts a to c, but substituting 2-amino-3-pyridinecarboxylic acid for 2-amino-5-pyridine carboxylic acid there was obtained the following:

(a)

2-Amino-3-pyridinecarboxylic acid ethyl ester as a yellow solid in 84% yield.

(b)

8-Carboethoxyimidazo[1,2-a]pyridine as a white solid in 97% yield, m.p. 59°–61° C.

(c)

1-Cyclopentyl-3-ethyl-6-(8-imidazo[1,2-a]pyridyl)pyrazolo[3,4-d]pyrimidin-4-one as white crystals in 35% yield when recrystallized from tert-butylmethyl ether/hexanes. This derivative was then converted into the methanesulfonate by treatment with methanesulfonic acid, dilution with methanol and filtration of the product to afford 1-cyclopentyl-3-ethyl-6-(8-imidazo[1,2-a]pyridine)pyrazolo[3,4-d]pyrimidin-4-one methanesulfonate as a white powder, m.p. 271°–272° C.

EXAMPLE 115

1-Cyclopentyl-3-methyl-6-(1-acetyl-4-piperidinyl)pyrazolo[3,4-d]pyrimidin-4-one

To a mixture of 1-cyclopentyl-3-methyl-6-(4-piperidinyl)pyrazolo[3,4-d]pyrimidin-4-one (0.79 g, 2.6 mmol), triethylamine (2.0 ml), and chloroform (25 ml) was added acetic anhydride (2.0 ml 0.02 mol) The mixture was stirred for 3 hours and the solvent was removed in vacuo. The residue was treated with water and the product was collected by filtration to afford 0.8 g (90%) of 1-cyclopentyl-3-methyl-6-(1-acetyl-4-piperidinyl)pyrazolo[3,4-d]pyrimidin-4-one as white needles, m.p. 176°–178° C. when recrystallized from cyclohexane.

EXAMPLE 116

1-Cyclopentyl-3-methyl-6-(1-trifluoroacetyl-4-piperidinyl)pyrazolo[3,4-d]pyrimidin-4-one Following a procedure substantially similar to that described in Example 15 but substituting trifluoroacetic anhydride for acetic anhydride there was obtained 1-cyclopentyl-3-methyl-6-(1-trifluoroacetyl-4-piperidinyl)pyrazolo[3,4-d]-pyrimidin-4-one as a white solid, m.p. 219°–221° C.

EXAMPLE 117

1-Cyclopentyl-3-ethyl-6-(2-chloro-6-methyl-4-pyridyl)pyrazolo[3,4-d]pyrimidin-4-one Following a procedure substantially similar to that described in Example 16, part c, but substituting ethyl 2-chloro-6-methyl-4-pyridinecarboxylate for 6-carboethoxy-imidazo[1,2-a]pyridine there was obtained 1-cyclopentyl-3-ethyl-6-(2-chloro-6-methyl-4-pyridyl)pyrazolo[3,4-d]pyrimidin-4-one as a white solid in 73% yield, m.p. 277°–278° C. when recrystallized from DMF.

Example 118

1-Cyclopentyl-3-ethyl-6-(2-methyl-4-pyridyl)pyrazolo[3,4-d]pyrimidin-4-one

A mixture of 1-cyclopentyl-3-ethyl-6-(2-chloro-6-methyl-4-pyridyl)pyrazolo[3,4-d]pyrimidin-4-one (1.3 g, 3.6 mmol), DMF (75 ml), triethylamine (1.0 ml, 7.2 mmol) and 10% palladium on carbon (0.13 g) was placed on a parr hydrogenator at 50 psi and heated via an external heating jacket to 60° C. for 2 hours, then at 70° C. for 6.5 hours. Additional catalyst was added and the mixture was placed back on the parr hydrogenator for 4 hours at 70° C. The mixture was filtered through a celite plug while hot, and the filtrate was concentrated in vacuo. Water was added to the residue and a white solid was collected by filtration to afford 0.96 g (82%) of 1-cyclopentyl-3-ethyl-6-(2-methyl-4-pyridyl)pyrazolo[3,4-d]pyrimidin-4-one as a white powder, m.p. 258°–259° C. when recrystallized from DMF/acetonitrile.

EXAMPLE 119

(a)

2-Chloro-4-cyanopyridine and 3-chloro-4-cyanopyridine

A mixture of 4-cyanopyridine N-oxide (30 g, 0.25 mol), phosphorous oxychloride (96 ml, 0.35 mol) and phosphorous pentachloride (72 g, 0.38 mol) was refluxed at 120°–130° C. for 6 hours and then stirred at room temperature for 12 hours. The reaction mixture was slowly poured into a mixture of ice/Na$_2$CO$_3$/K$_2$CO$_3$ and was extracted with chloroform (4×250 ml). The solvent was removed in vacuo and the residue was purified by column chromatography on silica eluting with 50% ether/hexanes to afford 8.4 g (24%) of 2-chloro-4-cyanopyridine, m.p. 69.5°–70.5° C. and 10.5 g (30%) of 3-chloro-4-cyanopyridine, m.p. 71.5°–72° C.

(b)

3-Ethoxy-4-cyanopyridine

A mixture of sodium metal (1.4 g, 0.06 mol) and ethanol (10 ml) was stirred until all of the sodium metal had dissolved and the solvent was removed in vacuo. The residue was placed under argon, and DMF (50 ml), followed by 3-chloro-4-cyanopyridine (6.95 g, 0.05 mol) were added at 5° C. The mixture was warmed to room temperature and stirred for 24 hours. The solvent was removed in vacuo and the residue was treated with dichloromethane and filtered. The filtrate was removed in vacuo, the residue was treated with water and a solid was collected by filtration to afford 4.6 g (62%) of 3-ethoxy-4-cyanopyridine as a tan solid, m.p. 56°–57° C.

(c)

1-Cyclopentyl-3-ethyl-6-(3-ethoxy-4-pyridyl)pyrazolo[3,4-d]pyrimidin-4-amine

To a mixture of 1-cyclopentyl-3-ethyl-5-amino-1H-pyrazole-4-carboxamide (2.0 g, 9.0 mmol), DMF (30 ml), and 3-ethoxy-4-cyanopyridine (1.47 g, 9.9 mmol) under argon was added sodium hydride (0.43 g, 10.8 mmol). The mixture was stirred at room temperature for 24 hours and the solvent was removed in vacuo. The residue was treated with water, acidified with acetic acid and a precipitate formed which was collected by filtration. The residue was purified by column chromatography on silica eluting with ether (100%) to acetone (100%) to afford 1.4 g (44%) of 1-cyclopentyl-3-ethyl-6-(3-ethoxy-4-pyridyl)pyrazolo[3,4-d]-pyrimidin-4-amine.

(d)

1-Cyclopentyl-3-ethyl-6-(3-ethoxy-4-pyridyl)pyrazolo[3,4-d]pyrimidin-4-one

Following a procedure substantially similar to that described in general Method I but using 1-cyclopentyl-3-ethyl-6-(3-ethoxy-4-pyridyl)pyrazolo[3,4-d]pyrimidin-4-amine there was obtained 1-cyclopentyl-3-ethyl-6-(3-ethoxy-4-pyridyl)pyrazolo[3,4-d]pyrimidin-4-one as yellow fibers in a 70% yield, m.p. 179°–180° C. when recrystallized from ether/hexanes (1/6).

EXAMPLE 120

1-Cyclopentyl-3-ethyl-6-[2-(1-imidazolyl)-6-methyl-4-pyridyl]pyrazolo[3,4-d]pyrimidin-4-one-¼ hydrate A mixture of 1-cyclopentyl-3-ethyl-6-(2-chloro-6-methyl-4-pyridyl)pyrazolo[3,4-d]pyrimidin-4-one (0.30 g, 0.84 mmol), imidazole (0.06 g, 0.9 mmol) and N-methyl-2-pyrrolidinone (10 ml) was refluxed for 60 hours. The mixture was cooled to room temperature, filtered through a plug of celite and the plug was rinsed with methanol. The solvent was removed in vacuo and the residue was washed with ethanol and the solution was filtered. The filtrate was treated with charcoal, filtered, and the solvent was removed in vacuo. The residue was triturated with ether and a dark solid was collected by filtration. The product was recrystallized from ether/methanol to afford 0.018 g (10%) of 1-cyclopentyl- 3-ethyl-6-[2-(1-imidazolyl)-6-methyl-4-pyridyl]pyrazolo[3,4-d]pyrimidin-4-one.¼ hydrate as a beige powder, m.p. 277°–278° C.

EXAMPLE 121

(a)

2-(1-Imidazolyl)-4-cyanopyridine

A mixture of 2-chloro-4-cyanopyridine (4.0 g, 28.9 mmol), imidazole (7.9 g, 115 mmol) and N-methyl-2-pyrrolidinone (50 ml) was heated at 150° C. for 58 hours. The solvent was removed by distillation and the residue was partitioned between chloroform and water. The organic layer was separated and the aqueous layer was extracted with chloroform (2×100 ml). The organic layers were combined and the solvent was removed in vacuo. The residue was triturated with ether and a solid was collected by filtration. The solid residue was purified by column chromatography eluting with hexanes/acetone (1/1) to afford 1.2 g (24%) of 2-(1-imidazolyl)-4-cyanopyridine as a tan solid, m.p. 146°–147° C.

Following a procedure substantially similar to that described in Example 19, parts c and d, but substituting 2-(1-imidazolyl)-4-cyanopyridine for 3-ethoxy-4-cyanopyridine in part c there was obtained the following:

(b)

1-Cyclopentyl-3-ethyl-6-[2-(1-imidazolyl)-4-pyridyl]pyrazolo[3,4-d]pyrimidin-4-amine as cream colored crystals in a 56% yield, m.p. 175°–177° C. when recrystallized from acetonitrile.

(c)

1-Cyclopentyl-3-ethyl-6-[2-(1-imidazolyl)-4-pyridyl]pyrazolo[3,4-d]pyrimidin-4-one as grey needles in a 77% yield, m.p. 295°–296° C. when recrystallized from DMF/isopropanol.

EXAMPLE 122

(a)

1-Cyclopentyl-3-ethyl-6-thioxopyrazolo[3,4-d]pyrimidin-4-one

A mixture of 1-cyclopentyl-3-ethyl-5-amino-1H-pyrazole-4-carboxamide (1.4 g, 6.3 mmol) o-ethylxanthic acid potassium salt (2.0 g, 14 mmol) and N-methyl-2-pyrrolidinone (5 ml) was heated to 145°–155° C. for 5 hours, cooled to room temperature and stirred for 24 hours. The mixture was poured into water (25 ml), acidified and the resulting precipitate was collected by filtration and washed with water. The product was recrystallized from cyclohexane/isopropanol, and was then dissolved in 10% aqueous $K_2CO_3$(25 ml). The solution was treated with charcoal and the colorless filtrate was acidified with acetic acid. A white precipitate was obtained which was collected by filtration, washed with water and dried 95°–100° C. in high vacuum to afford 1.2 g (72%) of 1-cyclopentyl-3-ethyl-6-thioxopyrazolo[3,4-d]-pyrimidin-4-one as a white powder, m.p. 248°–250° C.

(b)

1-Cyclopentyl-3-ethyl-6-methylthiopyrazolo[3,4-d]pyrimidin-4-one

A mixture of 1-cyclopentyl-3-ethyl-6-thioxopyrazolo[3,4-d]pyrimidin-4-one (5.2 g, 19.6 mmol), DMF (50 ml) and $K_2CO_3$ (2.8 g, 20 mmol) was stirred at ambient temperature for 25 minutes. The mixture was then treated with dimethylsulfate (3.8 ml, 40 mmol) and was stirred for 2 hours. The reaction mixture was poured into water and the resulting white precipitate was collected by filtration and washed with water. The product was recrystallized from cyclohexane/ether and dried in high vacuum at 70°–75° C. to afford 4.6 g (85%) of 1-cyclopentyl-3-ethyl-6-methylthiopyrazolo[3,4-d]pyrimidin-4-one as cream colored needles, m.p. 200°–202° C.

(c)

1-Cyclopentyl-3-ethyl-6-methylsulfonylpyrazolo[3,4-d]pyrimidin-4-one

A mixture of 1-cyclopentyl-3-ethyl-6-methylthiopyrazolo[3,4-d]pyrimidin-4-one (4.0 g, 14 mmol), chloroform (100 ml) and 85% m-chloroperoxybenzoic acid (10.3 g, 70 mmol) was stirred for 24 hours. The mixture was extracted with saturated $NaHCO_3$(100 ml) and the organic phase was separated and dried over anhydrous $MgSO_4$. The solvent was removed in vacuo and the solid residue was recrystallized from cyclohexane to afford 1.2 g (27%) of 1-cyclopentyl-3-ethyl-6-methylsulfonylpyrazolo[3,4-d]pyrimidin-4-one as yellow crystals, m.p. >300° C.

(d)

1-Cyclopentyl-3-ethyl-6-(1-imidazolyl)pyrazolo [3,4-d]pyrimidin-4-one

A mixture of -1-cyclopentyl-3-ethyl-6-methylsulfonylpyrazolo[3,4-d]pyrimidin-4-one (3.1 g, 0.01 mol) and imidazole (2.1 g, 0.03 mol) was heated at 165°–175° C. for 3.5 hours. The mixture was cooled to room temperature and water (25 ml), followed by acetic acid (3 ml) were added. A precipitate was obtained which was collected by filtration and washed with water. The product was recrystallized from ethanol/ether to afford 2.4 g (81%) of 1-cyclopentyl-3-ethyl-6-(1-imidazolyl)pyrazolo[3,4-d]-pyrimidin-4-one as white crystals, m.p. 228°–230° C.

EXAMPLE 123

(a)

Ethyl 2-(2,2-dicyano-1-methylthioethenyl)-4-pyridylacetate

To a mixture of ethyl 4-pyridylacetate (46.7 g, 0.28 mol), 3,3-bis(methylthio)-2-cyanoacrylonitrile (47.6 g, 0.28 mol) and p-dioxane (300 ml) cooled in an ice bath was added 60% NaH (11.2 g, 0.28 mol) over 30 minutes. The mixture was slowly warmed to room temperature over 2 hours and was stirred at ambient temperature for 4 hours. The mixture was poured into ice-water, acidified with acetic acid and the resulting precipitate was collected by filtration and washed with water. The product was recrystallized from cyclohexane and dried at 70°–75° C. in high vacuum to afford 40.3 g (50%) of ethyl 2-(2,2-dicyano-1-methylthioethenyl)-4-pyridylacetate as orange crystals, m.p. 148°–152° C.

(b)

Ethyl 2-(5-amino-1-tert-butyl-4-cyano-1H-pyrazol-3-yl)-4-pyridylacetate

Following a procedure substantially similar to that described in Example 4, part c, but substituting ethyl 2-(2, 2-dicyano-1-methylthioethenyl)-4-pyridylacetate for (1-methoxy-(3,4-dimethoxyphenylethylidene))malononitrile there was obtained ethyl 2-(5-amino-1-tert-butyl-4-cyano-1H-pyrazol-3-yl)-4-pyridylacetate as white flakes, m.p.141°–143° C.

(c)

1-tert-Butyl-3-(4-pyridylmethyl)-5-amino-1H-pyrazole-4-carboxamide

A mixture of ethyl 2-(5-amino-1-tert-butyl-4-cyano-1H-pyrazol-3-yl)-4-pyridylacetate (3.3. g, 10 mmol), sodium hydroxide (1.2 g, 30 mmol), ethanol (20 ml) and water (25 ml) was refluxed for 24 hours. The reaction mixture was quenched with acetic acid and the solvent was removed in vacuo. The residue was partitioned between water and chloroform, the organic layer was separated and the solvent was removed in vacuo. The residue was recrystallized from ether/isopropanol to afford 1.1 g (40%) of 1-tert-butyl-3-(4-pyridylmethyl)-5-amino-1H-pyrazole-4-carboxamide as a white solid, m.p. 125°–127° C.

(d)

1-tert-Butyl-3-pyridylmethyl-6-(4-pyridyl)pyrazolo [3,4-d]pyrimidin-4-one

Following a procedure substantially similar to that described in Example 16, part c, but substituting ethyl isonicotinate for 6-carboethoxyimidazo[1,2-a]pyridine and 1-tertbutyl-3-(4-pyridylmethyl)-5-amino-1H-pyrazole-4-carboxamide for 1-cyclopentyl-3-ethyl-5-amino-1H-pyrazole-4-carboxamide there was obtained 1-tert-butyl-3-(4-pyridylmethyl)-6-(4-pyridyl)-pyrazolo[3,4-d]pyrimidin-4-one in 84% yield as a white powder, m.p. 233°–235° C.

EXAMPLE 124

Following a procedure substantially similar to that described in Example 19, parts b and c, but substituting 4-(2-hydroxyethyl)morpholine for ethanol and 2-chloro-4-cyanopyridine for 3-chloro-4-cyanopyridine there was obtained:

(a)

2-[2-(4-morpholinyl) ethoxy]-4-cyanopyridine as a red oil in a 68% yield when purified by column chromatography on silica eluting with hexanes/ether (50/50).

(b)

1-Cyclopentyl-3-ethyl-6-[2-(4-morpholinyl) ethoxy-4-pyridyl]-pyrazolo[3,4-d]pyrimidin-4-amine in a 85% yield, m.p. 134°–135° C. when purified by column chromatography on silica eluting with ether to ether/acetone (50/50) and recrystallized from acetonitrile.

Following a procedure substantially similar to that described in Example 100, but substituting 1-cyclopentyl-3-ethyl-6-[2-(4-morpholinyl)ethoxy-4-pyridyl]pyrazolo[3,4-d]pyrimidin-4-amine for 1-cyclopentyl-3-cyano-6-(4-pyridyl)-pyrazolo[3,4-d]pyrimidin-4-amine there was obtained:

(c)

1-Cyclopentyl-3-ethyl-6-[2-(4-morpholinyl) ethoxy-4-pyridyl]pyrazolo[3,4-d]pyrimidin-4-one.¼ hydrate as yellow needles in a 37% yield, m.p. 195°–196.5° C. when recrystalized from isopropanol/water (3/5).

EXAMPLE 125

Following a procedure substantially similar to that described in Example 19, parts c and d, but substituting 2-chloro-4-cyanopyridine for 3-ethoxy-4-cyanopyridine there was obtained:

(a)

1-Cyclopentyl-3-ethyl-6-(2-chloro-4-pyridyl)pyrazolo[3, 4-d]pyrimidin-4-amine as a yellow solid in a 88% yield, m.p. 204°–206° C.

(b)

1-Cyclopentyl-3-ethyl-6-(2-chloro-4-pyridyl)pyrazolo[3, 4-d]pyrimidin-4-one as yellow needles in a 76% yield, m.p. 276.5°–277.5° C. when recrystallized from DMF/isopropanol (1/1).

EXAMPLE 126

(a)

1-Cyclopentyl-3-methyl-6-(4-pyridyl)pyrazolo[3,4-]pyrimidin-4-one 1'-oxide

A mixture of 1-cyclopentyl-3-methyl-6-(4-pyridyl)pyrazolo[3,4-d]pyrimidin-4-one (2.5 g, 8.4 mmol) 81% m-chloroperoxybenzoic acid (2.6 g, 12 mmol) and chloroform (200 ml) was stirred at room temperature for 72 hours. During this time, a precipitate formed which was collected by filtration and recrystallized from isopropanol to afford 2.1 g (81%) of 1-cyclopentyl-3-methyl-6-(4-pyridyl)pyrazolo[3,4-d]pyrimidin-4-one 1'-oxide as a yellow powder, m.p. >300° C.

(b)

1-Cyclopentyl-3-methyl-6-(2-oxo-4-pyridyl)pyrazolo[3,4-d]pyrimidin-4-one

A mixture of 1-cyclopentyl-3-methyl-6-(4-pyridyl)pyrazolo[3,4-d]pyrimidin-4-one 1'-oxide (1.5 g, 4.8 mmol) and acetic anhydride (200 ml) was refluxed for 48 hours and then stirred at room temperature for 2 days. The solvent was removed in vacuo and the residue was digested with water and a solid was collected by filtration. The solid residue was recrystallized from chloroform/methanol (1/1) to afford 0.52 g (25%) of 1-cyclopentyl-3-methyl-6-(2-oxo-4-pyridyl)pyrazolo[3,4-d]pyrimidin-4-one as an off-white powder, m.p. >300° C.

EXAMPLE 127

Following a procedure substantially similar to that described in Example 1, part d, but substituting 1-cyclopentyl-3-trifluoromethyl-5-amino-1H-pyrazole-4-carbonitrile for 1-(2-methylcyclopentyl)-3-methyl-5-amino-1H-pyrazole-4-carbonitrile there was obtained:

(a)

1-Cyclopentyl-3-trifluoromethyl-5-amino-1H-pyrazole-4-carboxamide in an 81% yield.

Following a procedure substantially similar to that described in Example 19, parts c and d, but substituting 1-cyclopentyl-3-trifluoromethyl-5-amino-1H-pyrazole-4-carboxamide for 1-cyclopentyl-3-ethyl-5-amino-1H-pyrazole-4-carboxamide there was obtained:

(b)

1-Cyclopentyl-3-trifluoromethyl-6-(3-ethoxy-4-pyridyl)pyrazolo[3,4-d]pyrimidin-4-amine as a yellow solid in a 39% yield when purified by column chromatography on silica eluting with ethyl acetate/hexanes (1/1).

(c)

1-Cyclopentyl-3-trifluoromethyl-6-(3-ethoxy-4-pyridyl)pyrazolo[3,4-d]pyrimidin-4-one as an off-white powder in a 52% yield, m.p. 200°–201° C. when recrystallized from ether.

EXAMPLE 128

(a)

3-Methoxy-4-cyanopyridine

A mixture of 3-chloro-4-cyanopyridine (2.69 g, 19.4 mmol) and DMF (35 ml) was cooled in an ice bath and 95% sodium methoxide (1.1 g, 19.4 mmol) was added. The solution was stirred for 2.5 hours and the solvent was removed in vacuo. Water was added to the residue and the resulting solid was collected by filtration to afford 1.1 g of product. Additional product was obtained by extraction of the aqueous layer with chloroform (3×100 ml), concentration of the solvent in vacuo and purification of the residue by column chromatography on silica eluting with ether to afford an additional 1.1 g of 3-methoxy-4-cyanopyridine (total yield 85%) as white needles, m.p. 66°–67° C.

Following a procedure substantially similar to that described in Example 19, parts c and d, but substituting 3-methoxy-4-cyanopyridine for 3-ethoxy-4-cyanopyridine there was obtained:

(b)

1-Cyclopentyl-3-ethyl-6-(3-methoxy-4-pyridyl)pyrazolo[3,4-d]pyrimidin-4-amine as cream colored crystals in a 77% yield, m.p. 174°–175° C. when recrystallized from isopropanol.

(c)

1-Cyclopentyl-3-ethyl-6-(3-methoxy-4-pyridyl)pyrazolo[3,4-d]pyrimidin-4-one as yellow needles in a 45% yield, m.p. 167°–168° C. when recrystallized from hexanes.

EXAMPLE 129

(a)

2-(4-Morpholinyl)-4-cyanopyridine

A mixture of 2-chloro-4-cyanopyridine (2.5 g, 18 mmol) and morpholine (6.29 g, 72 mmol) was heated at 110°–120° C. for 4 hours. The reaction mixture was cooled, poured into ice-water (15 ml) and stirred for 30 minutes. A yellow solid was obtained, which was collected by filtration, washed with water and dried in vacuo at 70° C. in the presence of $P_2O_5$ to afford 1.8 g (53%) of 2-(4-morpholinyl)-4-cyanopyridine, m.p. 135°–136.5° C.

Following a procedure substantially similar to that described in Example 19, parts c and d, but substituting 2-(4-morpholinyl)-4-cyanopyridine for 3-ethoxy-4-cyanopyridine there was obtained:

(b)

1-Cyclopentyl-3-ethyl-6-(2-(4-morpholinyl)-4-pyridyl)pyrazolo[3,4-d]pyrimidin-4-amine as a tan solid in a 85% yield, which also contains a small amount of the corresponding 4-one derivative.

(c)

1-Cyclopentyl-3-ethyl-6-(2-(4-morpholinyl)-4-pyridyl)pyrazolo[3,4-d]pyrimidin-4-one as yellow needles in an 46% yield, m.p. 254°–255° C. when recrystallized from isopropanol.

EXAMPLE 130

(a)

3-Cyclobutyloxy-4-cyanopyridine

A mixture of mineral oil free NaH (0.86 g, 21.4 mmol) and DMF (15 ml) was cooled in an ice-bath and cyclobutanol (1.6 ml, 20.5 mmol) was added in one portion. The mixture was slowly warmed to room temperature and was stirred for 45 minutes. The mixture was once again cooled in an ice-bath and 3-chloro-4-cyanopyridine (2.6 g, 18.6 mmol) was added in one portion. The mixture was warmed to room temperature and was stirred for 3 hours. Water (10 ml) was added and the solvent was removed in vacuo. Water (225 ml) was added to the residue and the mixture was extracted with ether (3×100 mL). The combined organic layers were dried over anhydrous $MgSO_4$, treated with charcoal and removed in vacuo to afford 3.0 g (95%) of 3-cyclobutyloxy-4-cyanopyridine as a white solid.

Following a procedure substantially similar to that described in Example 119, part c, but substituting 3-cyclobutyloxy-4-cyanopyridine for 3-ethoxy-4-cyanopyridine there was obtained directly:

(b)

1-Cyclopentyl-3-ethyl-6-(3-cyclobutyloxy-4-pyridyl)pyrazolo[3,4-d]pyrimidin-4-one as a white powder in a 15% yield, m.p. 160°–161° C.

Following a procedure substantially similar to that described in Example 130, parts a and b, but substituting the appropriate alcohol for cyclobutanol in part a there was obtained the following compounds illustrated in Examples 131–132:

EXAMPLE 131

(a) 3-(2-Methoxyethoxy)-4-cyanopyridine as a yellow oil in a yield when purified by column chromatography on silica eluting with 20% ether/hexanes.

(b)

1-Cyclopentyl-3-ethyl-6-(3-(2-methoxyethoxy)-4-pyridyl)pyrazolo[3,4-d]pyrimidin-4-one as white crystals in a 28% yield, m.p. 146°–149° C. when recrystallized from tert-butylmethyl ether.

EXAMPLE 132

(a)

3-Sec-butoxy-4-cyanopyridine as a gold oil in a 49% yield when purified by column chromatography oh silica eluting with ether/hexanes (60/40).

(b)

1-Cyclopentyl-3-ethyl-6-(3-sec-butoxy-4-pyridyl)pyrazolo[3,4-d]pyrimidin-4-one as a beige solid in a 43% yield, m.p. 89°–90° C. when purified by column chromatography on silica eluting with ether.

Following a procedure substantially similar to that described in Example 119, parts b, c and d, but substituting the appropriate alcohol for ethanol in part b there was obtained:

EXAMPLE 133

(a)

3-Propoxy-4-cyanopyridine as a yellow oil in a 57% yield when purified by column chromatography on silica eluting with tert-butylmethyl ether.

(b)

1-Cyclopentyl-3-ethyl-6-(3-propoxy-4-pyridyl)pyrazolo[3,4-d]pyrimidin-4-amine as brown crystals in a 71% yield, m.p. 162°–163° C., when purified by column chromatography on silica eluting with then acetone.

(c)

1-Cyclopentyl-3-ethyl-6-(3-propoxy-4-pyridyl)pyrazolo[3,4-d]pyrimidin-4-one as a brown solid in a 57% yield, m.p. 137°–138° C., when purified by column chromatography on silica eluting with ether.

Following a procedure substantially similar to that described in Example 119, part c, but substituting 1-tert-butyl-3-pyridylmethyl-5-amino-1H-pyrazole-4-carboxamide and 3-methoxy-4-cyanopyridine there was obtained:

EXAMPLE 134

(a)

1-tert-Butyl-3-pyridylmethyl-6-(3-methoxy-4-pyridyl)pyrazolo[3,4-d]pyrimidin-4-amine as a yellow foam in a 53% yield when purified by column chromatography on silica eluting with ether then acetone. The product, as isolated, contains a small amount of the corresponding 4-one derivative.

Following a procedure substantially similar to that described in Example 100 but substituting 1-tert-butyl-3-pyridylmethyl-6-(3-methoxy-4-pyridyl)pyrazolo[3,4-d]pyrimidin-4-amine for 1-cyclopentyl-3-cyano-6-(4-pyridyl)pyrazolo[3,4-d]pyrimidin-4-amine there was obtained:

(b)

1-tert-Butyl-3-(4-pyridylmethyl)-6-(3-methoxy-4-pyridyl)pyrazolo[3,4-d]pyrimidin-4-one as a grey powder in a 41% yield, m.p. 196°–197° C. when recrystallized from tert-butylmethyl ether.

Following a procedure substantially similar to that described in Example 119, part c, but substituting 3-methoxy-4-cyanopyridine for 3-ethoxy-4-cyanopyridine and the appropriate 1H-pyrazole-4-carboxamide for 1-cyclopentyl-3-ethyl-5-amino-1H-pyrazole-4-carboxamide there was obtained directly the compounds illustrated in Examples 135 and 136:

EXAMPLE 135

1-Cyclopentyl-3-trifluoromethyl-6-(3-methoxy-4-pyridyl)pyrazolo[3,4-d]pyrimidin-4-one as a white powder in a 7% yield, m.p. 226°–227° C. when purified by column chromatography on silica eluting with hexanes/ethyl acetate (1/1) and recrystallized from ether. 1-Cyclopentyl-3-trifluoromethyl-6-(3-hydroxy-4-pyridyl)pyrazolo[3,4-d]pyrimidin-4-amine was also isolated from the reaction mixture in a 23% yield, m.p. 187°–190° C. when recrystallized from ether.

EXAMPLE 136

1-tert-Butyl-3-ethyl-6-(3-methoxy-4-pyridyl)pyrazolo[3,4-d]pyrimidin-4-one as a white solid in 47% yield, m.p. 145°–146° C. when recrystallized from tert-butylmethyl ether.

Following a procedure substantially similar to that described in Example 1, part e, but substituting 3-pyridinecarboxaldehyde for 4-pyridinecarboxaldehyde and the appropriate 1H-pyrazole-4-carboxamide for 1-(2-methylcyclopentyl)-3-methyl-5-amino-1H-pyrazole-4-carboxamide there was obtained:

EXAMPLE 137

1-Cyclopentyl-3-ethyl-6-(3-pyridyl)pyrazolo[3,4-d]pyrimidin-4-one as white crystals in a 45% yield, m.p. 226°–228° C.

EXAMPLE 138

1-Cyclopentyl-3-trifluoromethyl-6-(3-hydroxy-4-pyridyl)pyrazolo[3,4-d]pyrimidin-4-one.

Following a procedure substantially similar to that described in Example 19, part d, 1-cyclopentyl-3-trifluoromethyl-6-(3-hydroxy-4-pyridyl)pyrazolo[3,4-d]pyrimidin-4-amine of Example 135 was converted into 1-cyclopentyl-3-trifluoromethyl-6-(3-hydroxy-4-pyridyl)pyrazolo[3,4-d]pyrimidin-4-one. The product was isolated as a white solid in a 27% yield, m.p. 205°–206° C. when recrystallized from chloroform.

Biological Test Results

In standard biological test procedures, the compounds of Formula I have been found to possess c-GMP-PDE I inhibitory activity and are thus useful in the treatment of heart failure and hypertension. The compounds of Formula I, in combination with nitrates, have also been found to be useful in reversing or reducing nitrate-induced tolerance and thus would be useful in the treatment of angina pectoris and congestive heart disease.

Multiple isozymic forms of cyclic nucleotide phosphodiesterase (PDE) have been identified in mammalian cells. These isozymes hydrolyze cyclic adenosine monophosphate (cAMP) and/or cyclic guanosine monophosphate (cGMP) to the presumably biologically inactive 5'-nucleotide phosphates. Elevation of intracellular cGMP in vascular smooth muscle triggers a cascade of events that leads to a reduction in muscle tone while elevations in renal tubule cell cGMP stimulates natriuresis and diuresis. Vascular smooth muscle and renal cells contain a phosphodiesterase isozyme that has a low Km (1 μM) for the hydrolysis of cGMP. This isozyme has been referred to as the cGMP-PDE or cGMP-PDE I since it elutes from an anion-exchange sepharose resin in the first-peak of PDE activity at a sodium acetate concentration between 150–200 mM. Thus inhibition of the cGMP-PDE isozyme is a viable subcellular mechanism by which increases in cGMP can produce a reduction in total peripheral resistance and a stimulation of natriuresis and diuresis. The development of cGMP-PDE inhibitors represents an approach for the discovery of agents useful for treating heart failure and hypertension. For example, compounds having high inhibitory potency for the cGMP-PDE are expected to lower blood pressure and induce natriuresis and diuresis.

The c-GMP-PDE I inhibitory activity of representative compounds of the invention was demonstrated by the following procedure.

The cGMP-PDE and other PDE isozymes were isolated from cardiovascular tissues (heart and aorta) of various animal species and man by anion-exchange and affinity chromatography as described by Silver et al., Sec. Messeng. Phos. 13:13–25, 1991; PDE activity, in the presence and absence of test compounds was determined essentially as described by Thompson et al., Adv. Cyclic Nucleotide Res. 10:69–92. To determine the potency and selectivity of compounds as PDE inhibitors, compounds are screened for their effect on cyclic nucleotide hydrolysis at 10 μM. If ≧50% inhibition of PDE activity is observed, an $IC_{50}$ value (concentration of compound causing 50% reduction in PDE activity) and corresponding 95% confidence intervals are generated. The $IC_{50}$ values are calculated from concentration-response curves as described by Tallarida and Murray, Manual of Pharmacologic Calculations with Computer Programs, Procedure 8, Graded Dose-response, pp. 14–19, Springer-Verlag, N.Y., 1981.

The following table summarizes the results obtained from the testing of representative compounds of the invention.

| Example No. | Percent Inhibition at Given μM or $IC_{50}$ (nM) cGMP-PDE I |
|---|---|
| 1e | 59% (1 μM) or 23% (0.1 μM) |
| 2f | 53% (10 μM) or 7% (1 μM) |
| 3e | 460/560* |
| 4e | 6 or 69% (0.01 μM) |
| 5e | 260 |
| 6e | 620 |
| 7c | 190 |
| 8 | 67% (10 μM) or 31% (1 μM) |
| 9 | 280 |
| 10a | 42% (10 μM) or 43% (1 μM) |
| 10b | 62% (1 μM) or 24% (0.1 μM) |
| 12c | 690 |
| 13b | 97 |
| 14c | 780 |
| 15e | 43% (10 μM) or 38% (1 μM) |
| 16c | 69% (1 μM) or 35% (0.1 μM) or 780 nM |
| 17e | 2300 |
| 18c | 45% (10 μM) or 0% (1 μM) |
| 19c | 74% (10 μM) or 32% (1 μM) |
| 20c | 70% (10 μM) or 36% (1 μM) |
| 71 | 3700 |
| 72 | 1150 |
| 73 | 1800 |
| 74 | 32% (10 μM) or 0% (1 μM) |
| 75 | 450/370* |
| 76 | 24% (10 μM) or 0% (1 μM) |
| 77 | 80% (10 μM) or 13% (1 μM) |
| 78 | 54% (1 μM) |
| 79 | 4700 |
| 80 | 2700 |
| 81 | 200 |
| 82 | 550 |
| 83 | 370 |
| 84 | 610 |
| 85 | 42% (10 μM) |
| 86 | 41% (10 μM) |
| 87 | 2700/3600* |
| 88 | 32% (1 μM) |
| 89 | 77% (10 μM) or 17% (1 μM) |
| 90 | 15/45* |
| 91 | 850 |
| 92 | 680 |
| 93 | 380 |
| 94 | 480 |
| 95 | 32% (10 μM) or 9% (1 μM) |
| 96 | 670 |
| 97 | 2400 |
| 98 | 560 |
| 99 | 12% (10 μM) or 0% (1 μM) |
| 100 | 35% (10 μM) or 9% (1 μM) |

-continued

| Example No. | Percent Inhibition at Given μM or IC$_{50}$ (nM) cGMP-PDE I |
|---|---|
| 101 | 1780 |
| 102 | 1900 |
| 103 | 19% (10 μM) or 0% (1 μM) |
| 104 | 12,400 |
| 105 | 6700 |
| 106 | 63% (10 μM) or 24% (1 μM) |
| 108 | 86% (10 μM) or 38% (1 μM) |
| 109 | 13% (10 μM) or 7% (1 μM) |
| 110 | 74% (10 μM) or 23% (1 μM) |
| 111 | 24% (10 μM) or 0% (1 μM) |
| 112 | 52% (10 μM) or 4% (1 μM) |
| 113 | 48% (10 μM) or 0% (1 μM) |
| 114c | 52% (10 μM) or 5% (1 μM) |
| 115 | 51% (10 μM) or 6% (1 μM) |
| 116 | 34% (1 μM) |
| 117 | 22% (10 μM) or 11% (1 μM) |
| 118 | 61% (1 μM) or 22% (0.1 μM) or 660 nM |
| 119d | 90% (0.1 μM) or 1.6 nM |
| 120 | 60% (1 μM) or 16% (0.1 μM |
| 121c | 68% (1 μM) or 11% (0.1 μM) or 240 nM |
| 122d | 46% (10 μM) or 16% (1 μM) |
| 123d | 90% (1 μM) or 55% (0.1 μM) or 120 nM |
| 124c | 86% (1 μM) or 50% (0.1 μM) or 19% (0.01 μM) or 150 nM |
| 125b | 59% (1 μM) or 27% (0.1 μM) or 580 nM |
| 126b | 32% (1 μM) or 0% (0.1 μM) |
| 127c | 93% (0.1 μM) or 79% (0.01 μM) or 1.8/2.5 nM* |
| 128c | 71% (0.1 μM) or 54% (0.01 μM) or 36 nM |
| 129c | 64% (1 μM) or 35% (0.1 μM) |
| 130B | 91% (0.01 μM) |
| 131b | 86% (1.0 μM) or 61% (0.1 μM) or 22% (0.01 μM) |
| 132b | 90% (0.01 μM) |
| 133c | 82% (0.01 μM) |
| 134b | 55% (0.1 μM) or 35% (0.01 μM) |
| 135 | 88% (1.0 μM) or 68% (0.1 μM) or 36% (0.01 μM) |
| 136 | 73% (1 μM) or 39% (0.1 μM) or 28% (0.01 μM) |
| 137 | 64% (1 μM) or 27% (0.1 μM) |

*The numbers represent IC$_{50}$ (nM) values for two separate experimental runs.

The antihypertensive activity of representative compounds of the invention was demonstrated by the following procedure.

Spontaneously hypertensive rats (SHR) were anesthetized with sodium pentobarbital (50 mg/kg, ip) and instrumented with catheters positioned in the inferior vena cava and abdominal aorta for administration of drug and recording of arterial pressure and heart rate, respectively. After a 2 day recovery from surgery, three baseline blood pressure measurements were made at 5 min intervals in conscious SHR. Compounds to be tested or vehicle were then administered intravenously in a dose-dependent manner (0.3–10 mg base/kg) while arterial pressure was recorded continuously on a polygraph. The mean arterial pressure response was measured 5 minutes after the administration of each dose of the test compound and the next dose given in a cumulative dose fashion. The response to each dose of the test compound was calculated as the difference from the mean of the three baseline measurements.

The following table summarizes the results obtained from the testing of representative compounds of the invention.

| Example No. | SHR iv % change in mean arterial pressure at Given mg/kg or ED$_{25}$ (mg/kg) |
|---|---|
| 4e | −2% (10 mg/kg) |
| 13b | −17% (1 mg/kg) or −14% (3 mg/kg) or −18% (18 mg/kg) |
| 14c | 7.8 |
| 75 | 1.7 |
| 83 | 1.0 |
| 90 | −6% (1 mg/kg) |
| 93 | 6.5 |
| 98 | 4.1 |
| 119d | 4.8 or −36% (10 mg/kg) or −24% (3 mg/kg) |
| 123d | −7% (10 mg/kg) |
| 124c | 10.1 or −24% (10 mg/kg) or −14% (3 mg/kg) |
| 127c | −14% (10 mg/kg) |
| 128c | 0.23 or −48% (10 mg/kg) |
| 132b | −12% (10 mg/kg) or −8% (3 mg/kg) or −9% (1 mg/kg) |

The activity of the compound of Example 83 in reversing or reducing nitrate-induced tolerance was demonstrated by the following procedures:

Procedure 1: in vitro activity

Male Sprague-Dawley rats (250–350 g body weight) were deeply anesthetized with pentobarbital (50 mg/kg) and then euthanized by exsanguination. The thoracic and abdominal cavities were immediately opened and the aorta was removed. In order to remove the influence of endogenous endothelial relaxing factor (EDRF), the entire length of the aorta was functionally denuded of the endothelial layer by gently scraping the luminal surface with a solid polyethylene catheter. The effectiveness of this procedure was tested in each preparation at the end of the experiment by measuring the vasorelaxant response to 1 μM carbachol, a stimulator of EDRF release. Aortic rings (2–3 mm) were prepared from segments of aorta and attached to stainless steel ring holders immersed in 10 ml glass jacketed tissue baths containing a modified Krebs solution (in mM: NaCl, 118; KCl, 4.7; MgCl$_2$, 1.2; KH$_2$PO$_4$, 1.2; CaCl$_2$, 1.6; NaHCO$_3$, 21.4; dextrose, 11.1; ethylenediaminetetraacetic acid; 0.026;), pH 7.4 at 37° C. The aortic rings were exposed to 550 μM nitroglycerin or vehicle (1.6% polyethylene glycol 400) for 1 hour, removed from the tissue baths, briefly rinsed with Krebs solution, then transferred to naive tissue baths and secured to tension transducers; aortic rings were rinsed with 70 ml of Krebs solution prior to the evaluation of nitroglycerin. The aortic rings were stretched with a preload of two grams, equilibrated for 75 minutes, then contracted to about 1.8 to 2.2 grams of active tension with 1 μM phenylephrine. Nitroglycerin- and vehicle-pretreated aortic rings were incubated with 0.1 μM of the compound of Example 83 or with vehicle (125 μM NaOH) for ten minutes followed by exposure to cumulative concentrations of nitroglycerin. Maximal change in contractile tension over a series of nine consecutive 10 minute intervals was recorded and expressed as percent relaxation relative to post pre-treatment, phenylephrine-induced tension. Mean EC$_{50}$ values were calculated from percent relaxation of individual tissues using a statistical program according to Tallarida and Murray, (Manual of Pharmacologic Calculations with Computer Programs, Springer-Verlag, N.Y. 1987) and are expressed as mean ±S.E.M.

Exposing aortic smooth muscle strips to 550 μM nitroglycerin for 60 minutes induced tolerance to nitroglycerin; the EC50 value for nitroglycerin relaxation was significantly increased (p <0.01; n=8) from 77±16 nM in vehicle treated, control strips to 1551±637 nM in strips which has been pre-exposed to nitroglycerin for 60 minutes ("tolerant aortic strips"). In nitroglycerin-tolerant strips, pretreatment with 0.1 μM of the compound of Example 83 reversed vasodilatory tolerance to nitroglycerin as shown by a significant reduction (p <0.01; n=8) in the EC50 value for nitroglycerin relaxation to 106±37 μM from a value of 1551±637 nM.

Procedure 2: in vivo activity

Spontaneously hypertensive rats (16–19 weeks of age) were made nitroglycerin tolerant by injecting 100 mlg/kg nitroglycerin s.c., 3-times/day for 3 days. While conscious and freely moving, the decrease in mean arterial pressure (MAP) in response to a challenge dose of nitroglycerin (10 μg/kg, i.v. bolus) was utilized to confirm tolerance.

Nitroglycerin injection (10 μg/kg) resulted in a −19 mmHg change in MAP in non-tolerant rats (n=6). This vasodepressor response was reduced to −11 mmHg in tolerant rats (n=11). Pretreatment of nitroglycerin tolerant rats (n=12) with a threshold dose of the compound of Example 83 (1 mg/kg, i.v., approximately 10 mmHg change in MAP) resulted in a −35 mmHg change in MAP in response to nitroglycerin injection (10 μg/kg).

The compounds of the invention can be prepared for use by conventional pharmaceutical procedures; that is, by dissolving or suspending them or their pharmaceutically acceptable salts in a pharmaceutically acceptable vehicle, e.g., water, aqueous alcohol, glycol, oil solution or oil-water emulsion, for parenteral or oral administration, or by incorporating them in unit dosage form as capsules or tablets for oral administration either alone or in combination with conventional adjuvants or excipients, e.g. calcium carbonate, starch, lactose, talc, magnesium stearate, and the like.

The percentage of active component in such compositions may be varied so that a suitable dosage is obtained. The dosage administered to a particular patient is variable depending upon the clinician's judgment using as criteria: the route of administration, the duration of treatment, the size and physical condition of the patient, the potency of the active component and the patient's response thereto. An effective dosage amount of the active component can thus readily be determined by the clinician after a consideration of all criteria and using his best judgment on the patient's behalf.

We claim:

1. A compound of the formula

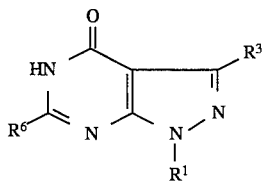

wherein:

$R^1$ is hydrogen, alkyl, cycloalkyl, cycloalkyl substituted by alkyl or hydroxyl, 2- or 3-tetrahydrofuranyl, 3-tetrahydrothienyl 1,1,-dioxide, cycloalkyl-alkyl, carboxyalkyl, carbo-lower-alkoxy-alkyl, dialkylaminoalkyl, phenyl-lower-alkyl, phenyl-lower-alkyl in which the phenyl ring is substituted in the 2, 3, or 4-position by one or two substituents, the same or different, selected from the group consisting of amino, halogen, alkyl, carboxyl, carbo-lower-alkoxy, carbamoyl, $NHSO_2$-(quinolinyl), nitro and cyano:

$R^3$ is hydrogen, lower-alkyl, phenyl-lower-alkyl, lower-alkoxyphenyl-lower-alkyl, dilower-alkoxy-phenyl-lower-alkyl, pyridyl-lower-alkyl, cycloalkyl-lower-alkyl, phenylamino, dialkylamino, halogen, trifluoromethyl, lower-alkylthio, cyano or nitro; and $R^6$ is a five or six membered heterocyclic ring containing from one to two nitrogen atoms, substituted—or unsubstituted—at any available carbon atom by one or two substituents, the same or different, selected from the group consisting of lower-alkyl, halogen, lower-alkoxy, cycloalkyloxy, 4-morpholinyl, lower-alkoxy-lower-alkoxy, hydroxy, imidazolyl, oxo and 4-morpholinyl-lower-alkoxy; or at any available nitrogen atom by lower-alkyl, lower-alkanoyl, or trifluoroacetyl; or a pharmaceutically acceptable acid-addition salt thereof.

2. A compound according to claim 1 wherein:

$R^1$ is alkyl, cycloalkyl, cycloalkyl-alkyl, carboxyalkyl, carbo-lower-alkoxy-alkyl, phenyl-lower-alkyl, phenyl-lower-alkyl in which the phenyl ring is substituted in the 2, 3 or 4-position by one or two substituents, the same or different, selected from the group consisting of amino, halogen, alkyl, carbo-lower-alkoxy, carbamoyl, $NHSO_2$-(quinolinyl), and nitro; and $R^3$ is lower-alkyl, phenyl-lower-alkyl, lower-alkoxyphenyl-lower-alkyl, dilower-alkoxy-phenyl-lower-alkyl, pyridyl-lower-alkyl, cycloalkyl-lower-alkyl, phenylamino, dialkylamino, trifluoromethyl, or lower-alkylthio.

3. A compound according to claim 2 wherein $R^6$ is selected from the group consisting of:

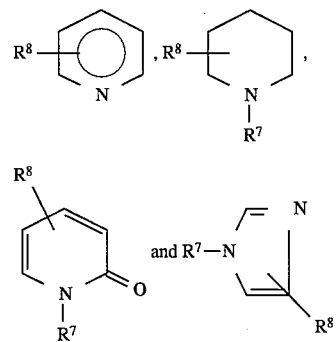

which can be attached through any available ring carbon atom for nitrogen atom to position six of the pyrazolo[3,4-d]pyrimidin-4-one;

$R^7$ is hydrogen, lower-alkyl, lower-alkanoyl or trifluoroacetyl, and $R^8$ is one or two substituents, the same or different, selected from the group consisting of hydrogen, lower-alkyl, halogen, lower-alkoxy, cycloalkyloxy, 4-morpholinyl, lower-alkoxy-lower-alkoxy, hydroxy, imidazolyl and 4-morpholinyl-lower-alkoxy which can be attached to any available ring carbon atom; or a pharmaceutically acceptable acid-addition salt thereof.

4. A compound according to claim 3 wherein $R^6$ is:

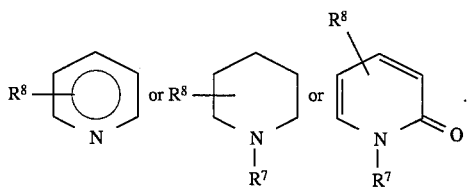

5. A compound according to claim 4 wherein $R^6$ is:

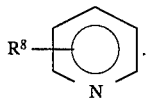

6. A compound according to claim 5 wherein $R^6$ is 4-pyridyl and $R^8$ is one or two substituents, the same or different, selected from the group consisting of hydrogen, lower-alkyl, halogen, lower-alkoxy, cycloalkyloxy, lower-alkoxy-lower-alkoxy, imidazolyl and 4-morpholinyl-lower-alkoxy.

7. A compound according to claim 6 wherein $R^1$ is alkyl, cycloalkyl or substituted phenyl-lower-alkyl; and $R^3$ is lower-alkyl, trifluoromethyl, phenyl-lower-alkyl, di-lower-alkoxy-phenyl-lower-alkyl, pyridyl-lower-alkyl, or cycloalkyl-lower-alkyl.

8. A compound according to claim 7 wherein $R^1$ is tert-butyl or cyclopentyl.

9. A compound according to claim 8 wherein $R^3$ is methyl, ethyl, trifluoromethyl, phenylmethyl, 3,4-dimethoxyphenylmethyl, 4-pyridylmethyl, or cyclohexylmethyl.

10. 1-Cyclopentyl-3-methyl-6-(4-pyridyl)pyrazolo[3,4-d]pyrimidin-4-one, according to claim 9.

11. 1-Cyclopentyl-3-ethyl-6-(3-ethoxy-4-pyridyl)pyrazolo[3,4-d]pyrimidin-4-one, according to claim 9.

12. 1-Cyclopentyl-3-ethyl-6-(3-methoxy-4-pyridyl)pyrazolo[3,4-d]pyrimidin-4-one, according to claim 9.

13. 1-Cyclopentyl-3-trifluoromethyl-6-(3-ethoxy-4-pyridyl)pyrazolo[3,4-d]pyrimidin-4-one, according to claim 9.

14. A compound according to claim 4 wherein $R^6$ is:

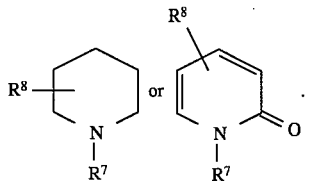

15. A compound according to claim 14 wherein $R^1$ is alkyl, cycloalkyl or substituted phenyl-lower-alkyl; $R^3$ is lower-alkyl, trifluoromethyl, phenyl-lower-alkyl, di-lower-alkoxy-lower-alkyl, pyridyl-lower-alyl, or cycloalkyl-lower-alkyl; and $R^6$ is 4-piperidinyl, 1-acetyl-4-piperidinyl, 1-trifluoromethyl-4-piperidinyl or 2-oxo-4-pyridyl.

16. A compound according to claim 15 wherein $R^1$ is cycloalkyl; and $R^3$ is lower-alkyl.

17. A compound according to claim 16 wherein $R^1$ is cyclopentyl; and $R^3$ is methyl.

18. A compound according to claim 3 wherein $R^6$ is

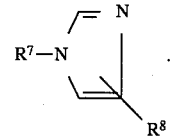

19. A compound according to claim 18 wherein $R^1$ is alkyl, cycloalkyl or substituted phenyl-lower-alkyl; $R^3$ is lower-alkyl, trifluoromethyl, phenyl-lower-alkyl, dilower-alkoxyphenyl-lower-alkyl, pyridyl-lower-alkyl, or cycloalkyl-lower-alkyl; and $R^6$ is 1-imidazolyl.

20. A compound according to claim 19 wherein $R^1$ is cycloalkyl; and $R^3$ is lower-alkyl.

21. 1-Cyclopentyl-3-ethyl-6-(2-(1-imidazolyl)-4-pyridyl)pyrazolo[3,4-d]pyrimidin-4-one, according to claim 20.

22. A pharmaceutical composition comprising an antihypertensively effective amount of a compound according to claim 1 together with a pharmaceutically acceptable carrier or diluent.

23. A pharmaceutical composition comprising an antihypertensively effective amount of a compound according to claim 4 together with a pharmaceutically acceptable carrier or diluent.

24. A pharmaceutical composition comprising an antihypertensively effective amount of a compound according to claim 5 together with a pharmaceutically acceptable carrier or diluent.

25. A pharmaceutical composition comprising an antihypertensively effective amount of a compound according to claim 9 together with a pharmaceutically acceptable carrier or diluent.

26. A method of treating hypertension in a mammalian organism which comprises administering to said organism an effective amount of a composition according to claim 22.

27. A method of treating hypertension in a mammalian organism which comprises administering to said organism an effective amount of a composition according to claim 23.

28. A method of treating hypertension in a mammalian organism which comprises administering to said organism an effective amount of a composition according to claim 24.

29. A method of treating hypertension in a mammalian organism which comprises administering to said organism an effective amount of a composition according to claim 25.

* * * * *